(12) United States Patent
Mueller et al.

(10) Patent No.: US 8,152,851 B2
(45) Date of Patent: Apr. 10, 2012

(54) EXPANDABLE CORPECTOMY DEVICE

(75) Inventors: Richard Mueller, Carlsbad, CA (US); Andrew Budd, Clinton, OH (US); Marc Silski, West Bloomfield, MI (US); Nickolas G. Kriska, North Canton, OH (US)

(73) Assignee: Theken Spine, LLC, Akron, OH (US)

( * ) Notice: Subject to any disclaimer, the term of this patent is extended or adjusted under 35 U.S.C. 154(b) by 805 days.

(21) Appl. No.: 12/202,878

(22) Filed: Sep. 2, 2008

(65) Prior Publication Data

US 2009/0118765 A1 May 7, 2009

Related U.S. Application Data

(63) Continuation-in-part of application No. 11/327,621, filed on Jan. 6, 2006, which is a continuation of application No. 10/550,329, filed as application No. PCT/US2004/008980 on Mar. 24, 2004, now Pat. No. 7,918,876.

(60) Provisional application No. 60/457,158, filed on Mar. 24, 2003.

(51) Int. Cl.
*A61F 2/44* (2006.01)
(52) U.S. Cl. ................. 623/17.15; 623/17.16; 623/17.11
(58) Field of Classification Search .... 623/17.11–17.16; 403/109.1–109.5
See application file for complete search history.

(56) References Cited

U.S. PATENT DOCUMENTS

| | | | |
|---|---|---|---|
| 1,036,204 A | 8/1912 | Farnham | |
| 1,457,825 A | 6/1923 | Devan | |
| 1,512,842 A | 10/1924 | Givens | |
| 2,620,001 A | 12/1952 | Fratz et al. | |
| 3,837,753 A | 9/1974 | Weiste et al. | |
| 4,011,602 A | 3/1977 | Rybicki et al. | |
| 4,126,057 A | 11/1978 | von Allwörden et al. | |
| 4,203,430 A | 5/1980 | Takahashi | |
| 4,309,777 A | 1/1982 | Patil | |
| 4,484,570 A | 11/1984 | Sutter et al. | |
| 4,553,273 A | 11/1985 | Wu | |
| 4,554,914 A | 11/1985 | Kapp et al. | |
| 4,611,582 A | 9/1986 | Duff | |
| 4,657,550 A | 4/1987 | Daher | |
| 4,932,975 A | 6/1990 | Main et al. | |
| 4,938,768 A | 7/1990 | Wu | |
| 4,946,378 A | 8/1990 | Hirayama et al. | |
| 5,059,193 A | 10/1991 | Kuslich | |
| 5,171,278 A | 12/1992 | Pisharodi | |
| 5,236,460 A | 8/1993 | Barber | |
| 5,290,312 A | 3/1994 | Kojimoto et al. | |
| 5,312,405 A | 5/1994 | Korotko et al. | |
| 5,330,535 A | 7/1994 | Moser et al. | |
| 5,336,223 A | 8/1994 | Rogers | |
| 5,390,683 A | 2/1995 | Pisharodi | |
| 5,413,602 A | 5/1995 | Metz-Stavenhagen | |
| 5,423,818 A | 6/1995 | Van Hoeck et al. | |
| 5,443,515 A | 8/1995 | Cohen et al. | |
| 5,458,641 A | 10/1995 | Ramirez Jimenez | |
| 5,571,190 A | 11/1996 | Ulrich et al. | |
| 5,571,192 A | 11/1996 | Schönhöffer | |
| 5,653,763 A | 8/1997 | Errico et al. | |
| 5,664,762 A | 9/1997 | Rothbauer | |
| 5,665,122 A | 9/1997 | Kambin | |

(Continued)

*Primary Examiner* — Thomas C. Barrett
*Assistant Examiner* — Andrew Yang
(74) *Attorney, Agent, or Firm* — Middleton Reutlinger; Robert H. Eichenberger; Chad Bruggeman

(57) ABSTRACT

An adjustable length corpectomy device is provided with a means for providing bidirectional length adjustment and a means for selectively fixing the length of the implant.

20 Claims, 48 Drawing Sheets

U.S. PATENT DOCUMENTS

| | | |
|---|---|---|
| 5,667,506 A | 9/1997 | Sutterlin |
| 5,669,910 A | 9/1997 | Korhonen et al. |
| 5,700,264 A | 12/1997 | Zucherman et al. |
| 5,702,453 A | 12/1997 | Rabbe et al. |
| 5,702,455 A | 12/1997 | Saggar |
| 5,707,372 A | 1/1998 | Errico et al. |
| 5,776,197 A | 7/1998 | Rabbe et al. |
| 5,776,198 A | 7/1998 | Rabbe et al. |
| 5,800,550 A | 9/1998 | Sertich |
| 5,893,889 A | 4/1999 | Harrington |
| 5,897,085 A | 4/1999 | Cronin |
| 5,947,966 A | 9/1999 | Drewry et al. |
| 5,980,523 A | 11/1999 | Jackson |
| 5,989,290 A | 11/1999 | Biedermann et al. |
| 6,015,436 A | 1/2000 | Schonhoffer |
| 6,113,600 A | 9/2000 | Drummond et al. |
| 6,126,660 A | 10/2000 | Dietz |
| 6,126,689 A | 10/2000 | Brett |
| 6,159,244 A | 12/2000 | Suddaby |
| 6,176,881 B1 | 1/2001 | Schar et al. |
| 6,190,413 B1 | 2/2001 | Sutcliffe |
| 6,190,414 B1 | 2/2001 | Young et al. |
| 6,193,755 B1 | 2/2001 | Metz-Stevenhagen et al. |
| 6,193,756 B1 | 2/2001 | Studer et al. |
| 6,200,348 B1 | 3/2001 | Biedermann et al. |
| 6,234,705 B1 | 5/2001 | Troxell |
| 6,238,396 B1 | 5/2001 | Lombardo |
| 6,283,967 B1 | 9/2001 | Troxell et al. |
| 6,296,665 B1 | 10/2001 | Strnad et al. |
| 6,306,137 B2 | 10/2001 | Troxell |
| 6,328,741 B1 | 12/2001 | Richelsoph |
| 6,344,057 B1 | 2/2002 | Rabbe et al. |
| 6,375,683 B1 | 4/2002 | Crozet et al. |
| 6,395,034 B1 | 5/2002 | Suddaby |
| 6,402,751 B1 | 6/2002 | Hoeck |
| 6,409,766 B1 | 6/2002 | Brett |
| 6,419,705 B1 | 7/2002 | Erickson |
| 6,435,048 B1 | 8/2002 | Zimmerman |
| 6,454,806 B1 | 9/2002 | Cohen et al. |
| 6,520,192 B1 | 2/2003 | Lo |
| 6,524,341 B2 | 2/2003 | Lang et al. |
| 6,554,832 B2 | 4/2003 | Shluzas |
| 6,562,074 B2 | 5/2003 | Gerbec et al. |
| 6,578,240 B2 | 6/2003 | Fortenberry |
| 6,602,253 B2 | 8/2003 | Richelsoph et al. |
| 6,616,668 B2 | 9/2003 | Altarac et al. |
| 6,616,695 B1 | 9/2003 | Crozet et al. |
| 6,660,038 B2 | 12/2003 | Boyer, II et al. |
| 6,719,796 B2 | 4/2004 | Cohen et al. |
| 6,723,126 B1 | 4/2004 | Berry |
| 6,730,068 B2 | 5/2004 | Kashiwagi et al. |
| 6,730,088 B2 | 5/2004 | Yeh |
| 6,752,832 B2 | 6/2004 | Neumann |
| 6,758,862 B2 | 7/2004 | Berry et al. |
| 6,776,798 B2 | 8/2004 | Camino et al. |
| 6,786,890 B2 | 9/2004 | Preuthun et al. |
| 6,808,538 B2 | 10/2004 | Paponneau |
| 6,866,682 B1 | 3/2005 | An et al. |
| 6,872,208 B1 | 3/2005 | McBride et al. |
| 6,902,579 B2 | 6/2005 | Harms et al. |
| 6,908,485 B2 | 6/2005 | Crozet et al. |
| 6,953,477 B2 | 10/2005 | Berry |
| 6,991,653 B2 | 1/2006 | White et al. |
| 7,014,659 B2 | 3/2006 | Boyer, II et al. |
| 7,018,415 B1 | 3/2006 | McKay |
| 7,022,138 B2 | 4/2006 | Mashburn |
| 7,056,343 B2 | 6/2006 | Schafer et al. |
| 7,094,257 B2 | 8/2006 | Mujwid et al. |
| 7,156,874 B2 | 1/2007 | Paponneau et al. |
| 7,384,431 B2 | 6/2008 | Berry |
| 7,392,151 B2 | 6/2008 | Mäkelä |
| 7,544,208 B1 | 6/2009 | Mueller et al. |
| 2002/0143330 A1 | 10/2002 | Shluzas |
| 2003/0065396 A1 | 4/2003 | Michelson |
| 2003/0093035 A1 | 5/2003 | Mohammed |
| 2003/0199980 A1 | 10/2003 | Siedler |
| 2004/0049271 A1 | 3/2004 | Biedermann et al. |
| 2004/0073314 A1 | 4/2004 | White et al. |
| 2004/0088054 A1 | 5/2004 | Berry |
| 2004/0153156 A1 | 8/2004 | Cohen et al. |
| 2004/0153160 A1 | 8/2004 | Carrasco |
| 2004/0186569 A1 | 9/2004 | Berry |
| 2004/0210312 A1 | 10/2004 | Neumann |
| 2004/0236427 A1 | 11/2004 | Berry et al. |
| 2005/0085910 A1 | 4/2005 | Sweeney |
| 2005/0090898 A1 | 4/2005 | Berry et al. |
| 2005/0107878 A1 | 5/2005 | Conchy |
| 2005/0113921 A1 | 5/2005 | An et al. |
| 2005/0159813 A1 | 7/2005 | Molz, IV |
| 2005/0209697 A1 | 9/2005 | Paponneau et al. |
| 2005/0228377 A1 | 10/2005 | Chao et al. |
| 2005/0234550 A1 | 10/2005 | Metz-Stavenhagen |
| 2006/0058877 A1 | 3/2006 | Gutlin |
| 2006/0058879 A1 | 3/2006 | Metz-Stavenhagen |
| 2006/0074490 A1 | 4/2006 | Sweeney |
| 2006/0100710 A1 | 5/2006 | Gutlin et al. |
| 2006/0116770 A1 | 6/2006 | White et al. |
| 2006/0195095 A1 | 8/2006 | Mueller et al. |
| 2006/0200244 A1 | 9/2006 | Assaker |
| 2006/0241762 A1 | 10/2006 | Kraus |
| 2007/0028710 A1 | 2/2007 | Kraus et al. |
| 2008/0243254 A1 | 10/2008 | Butler |

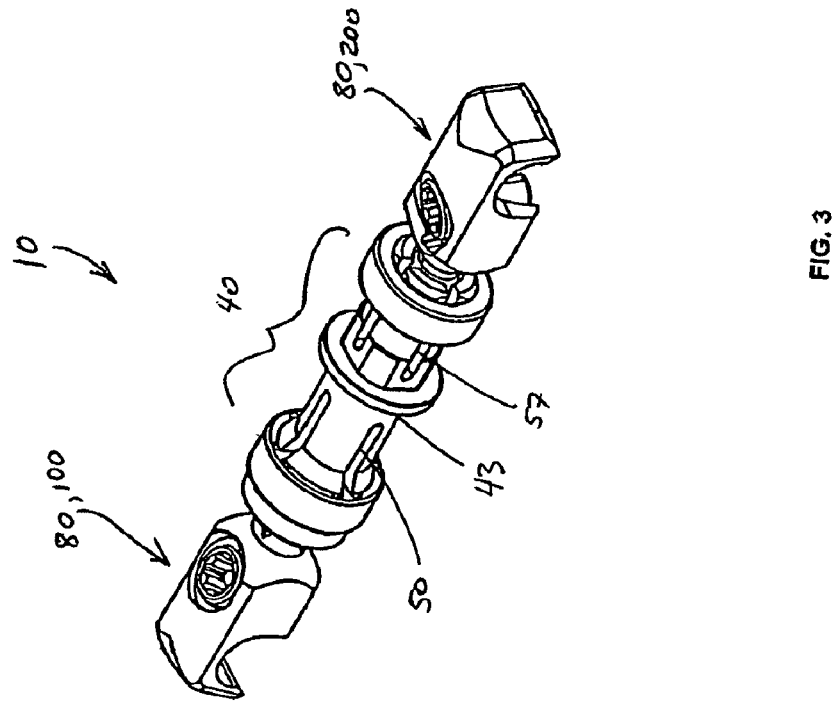
FIG. 3
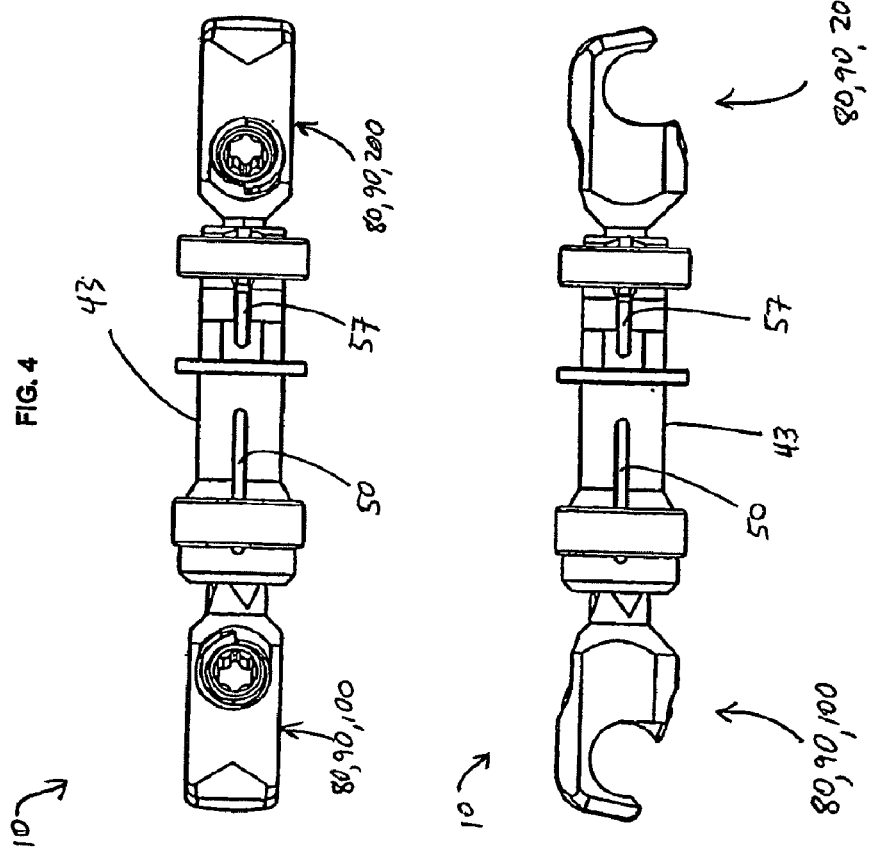
FIG. 4
FIG. 5

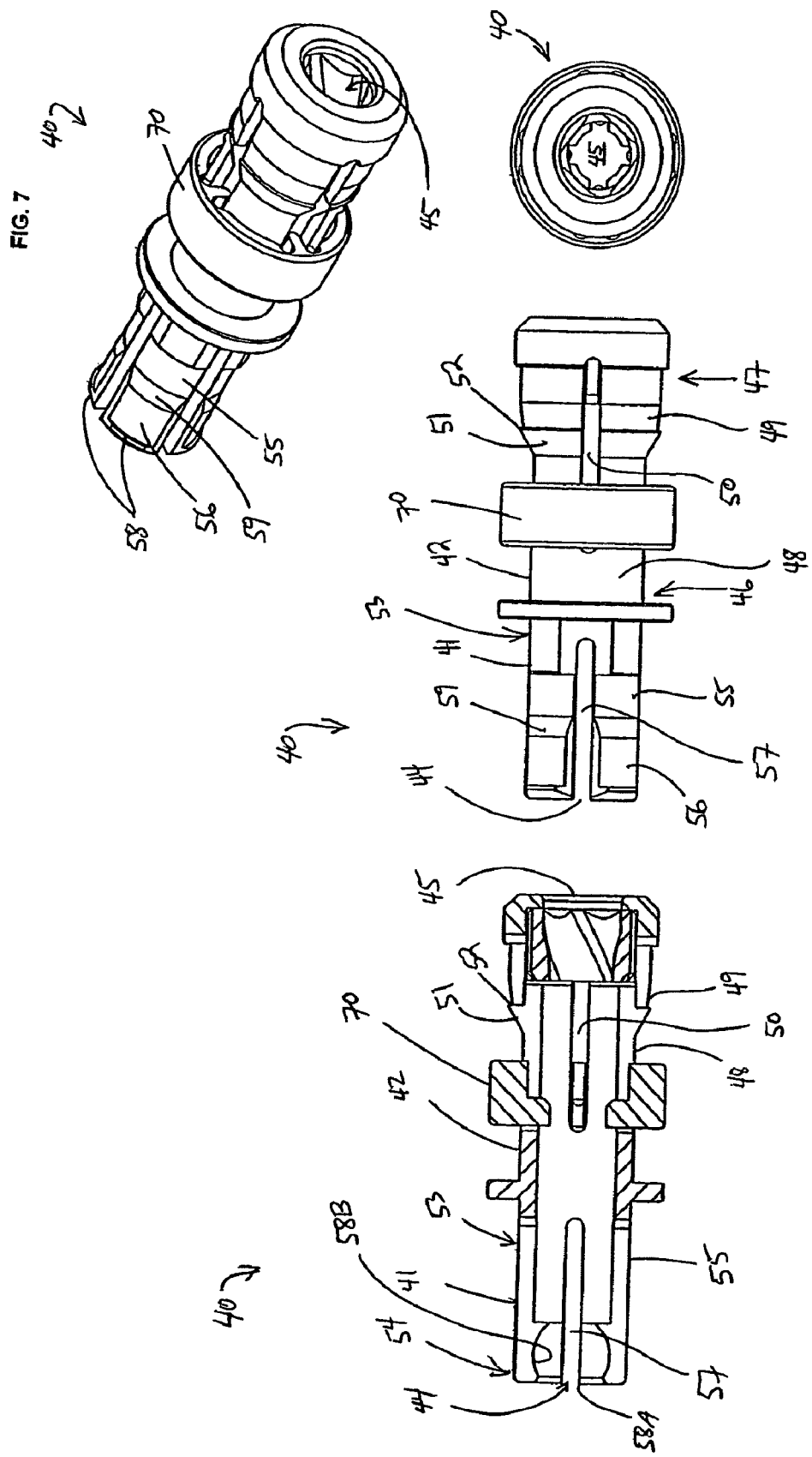

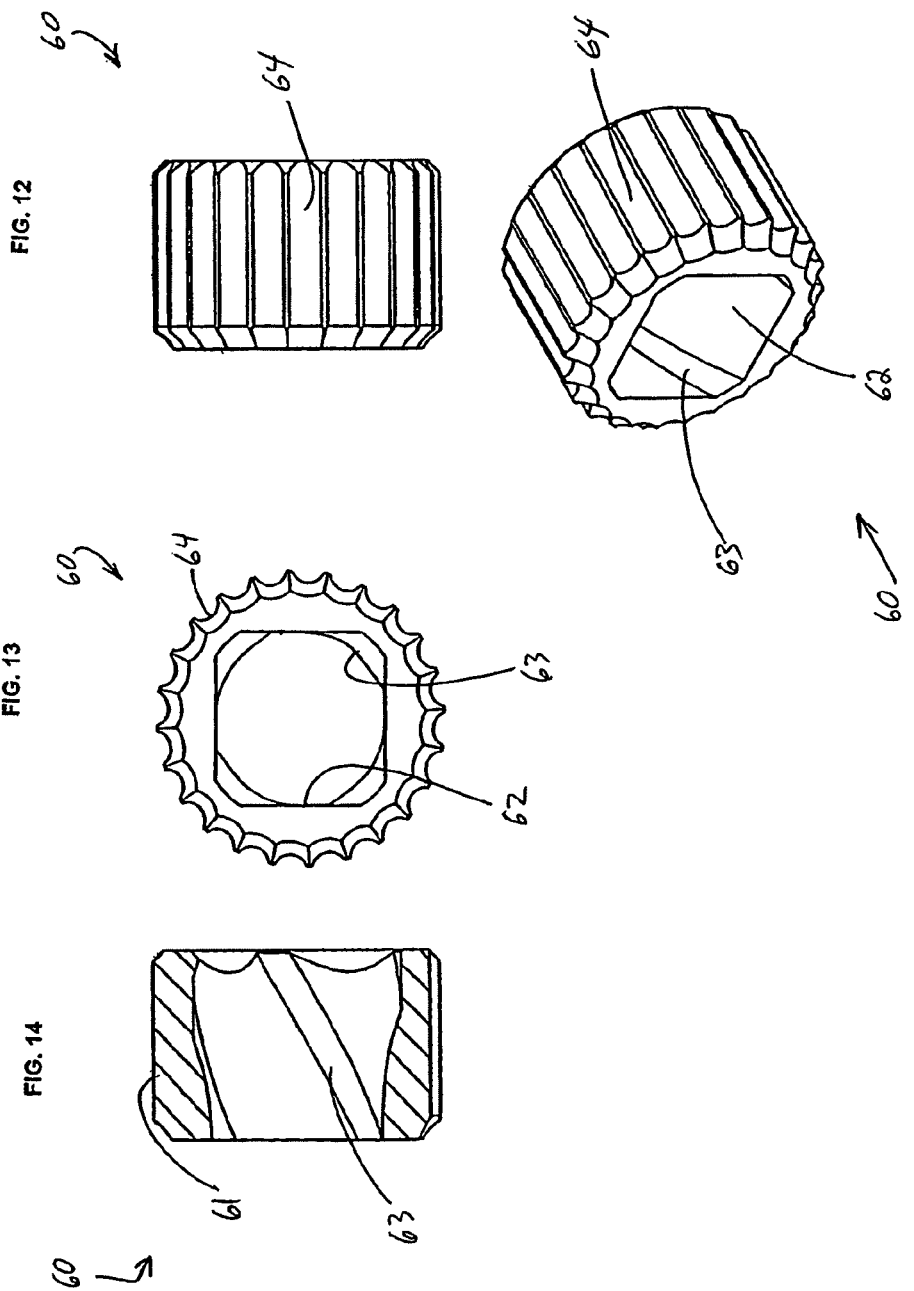

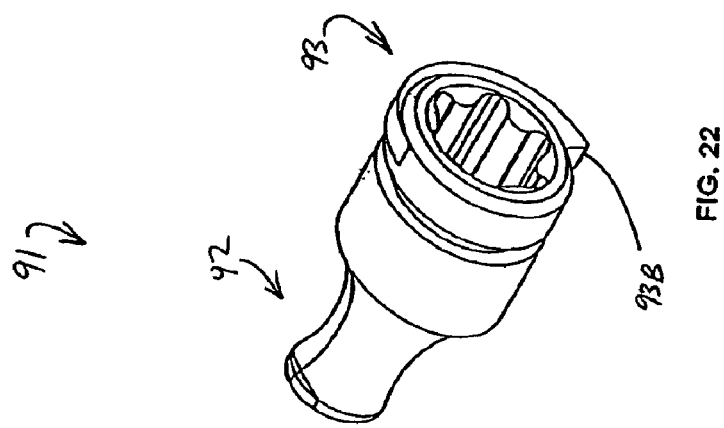
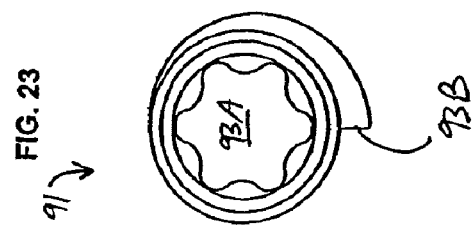
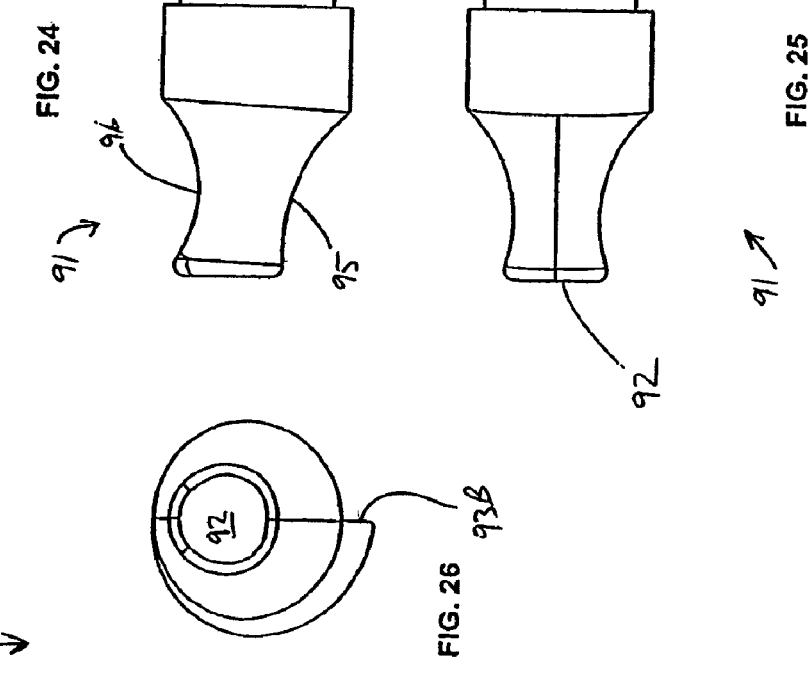
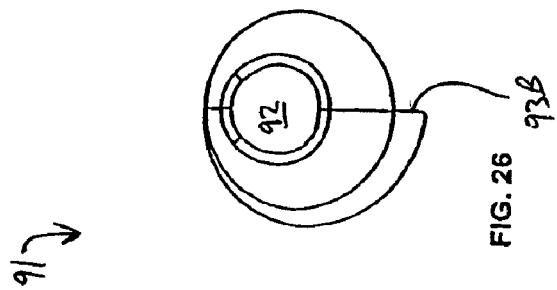

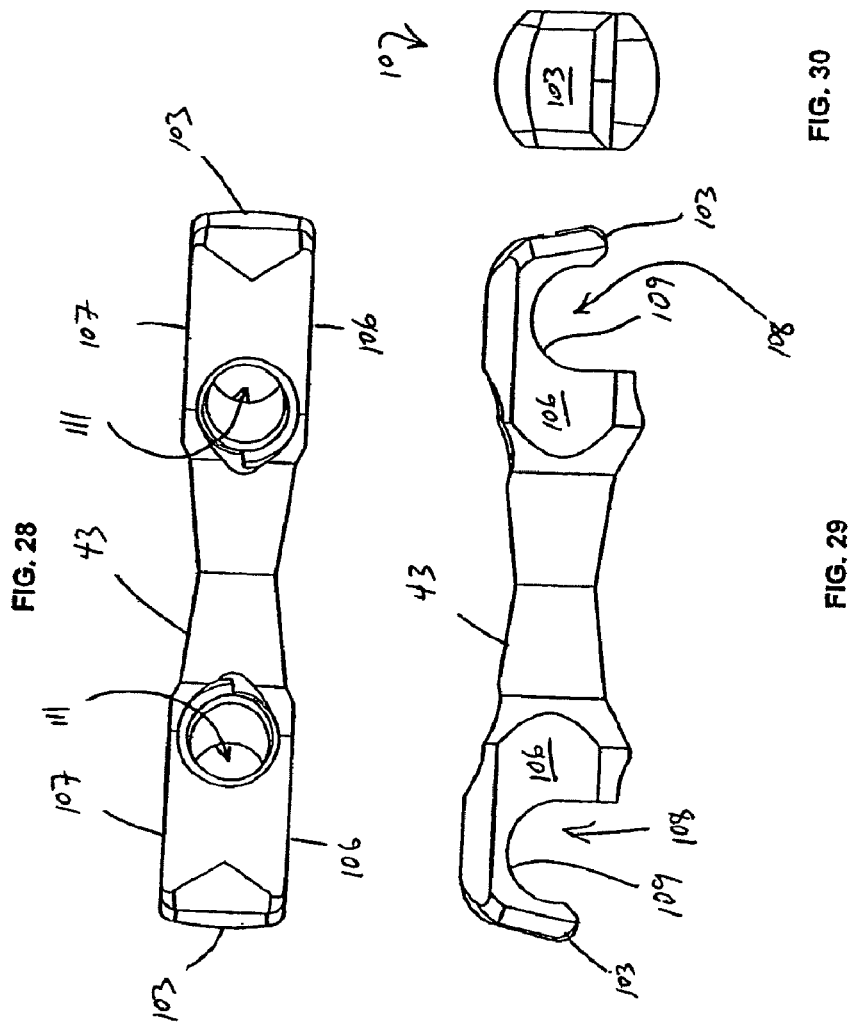
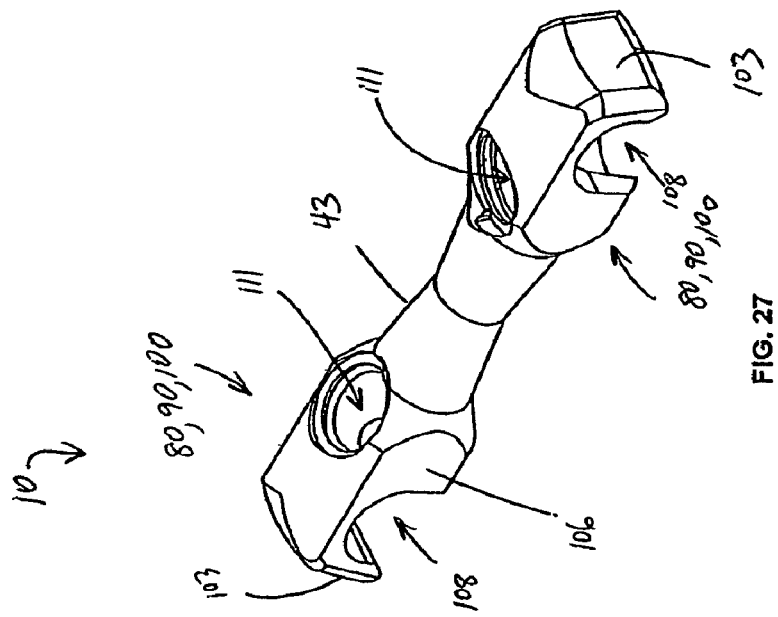

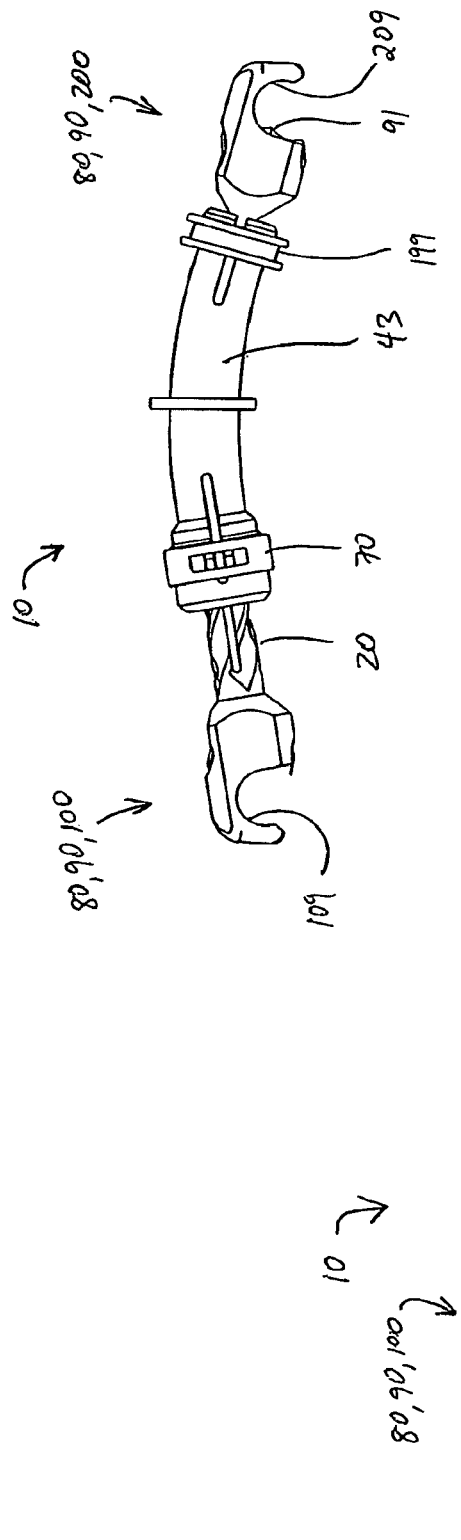
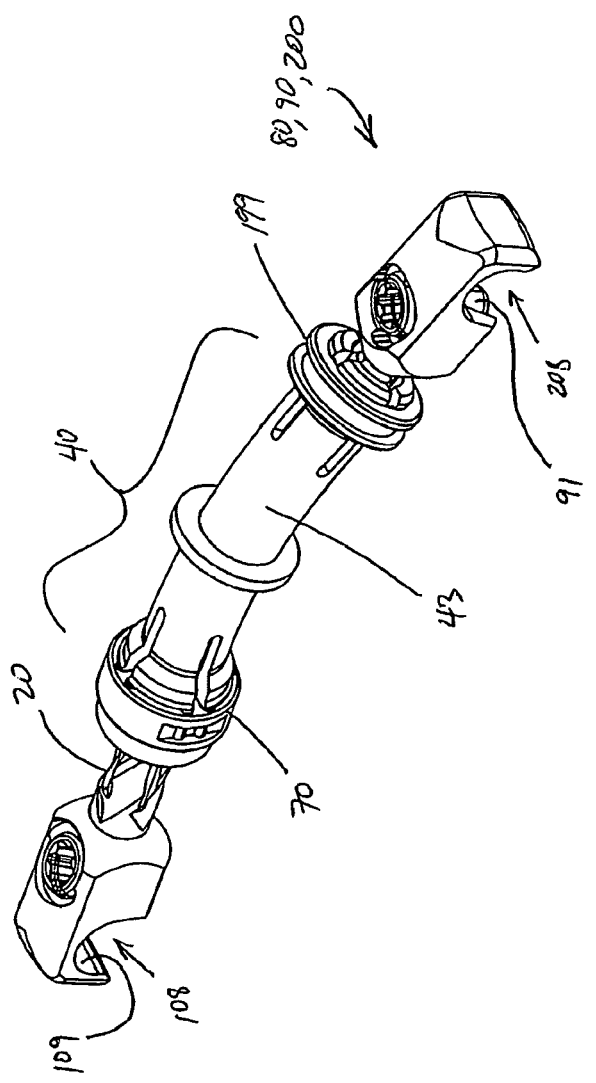
FIG. 46
FIG. 45

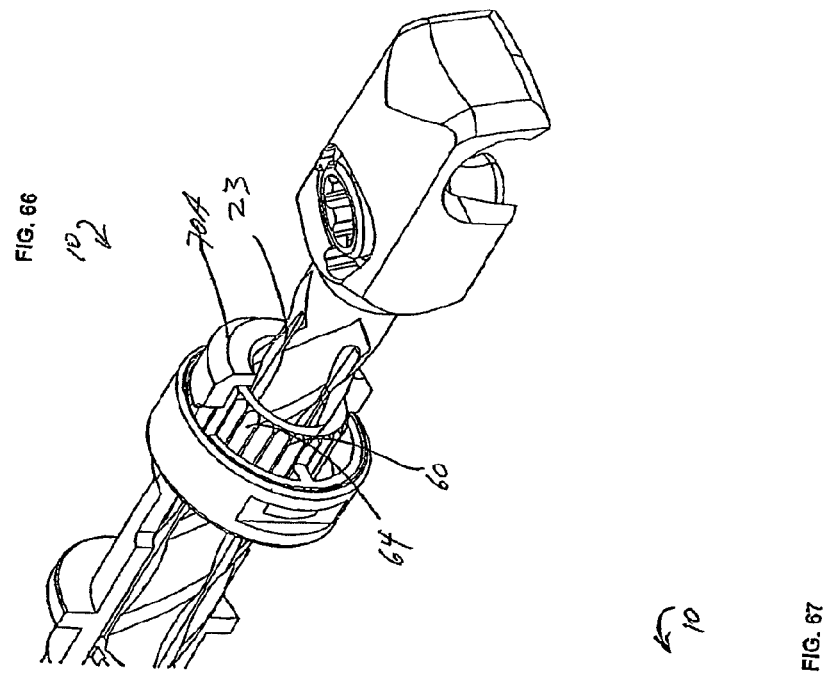
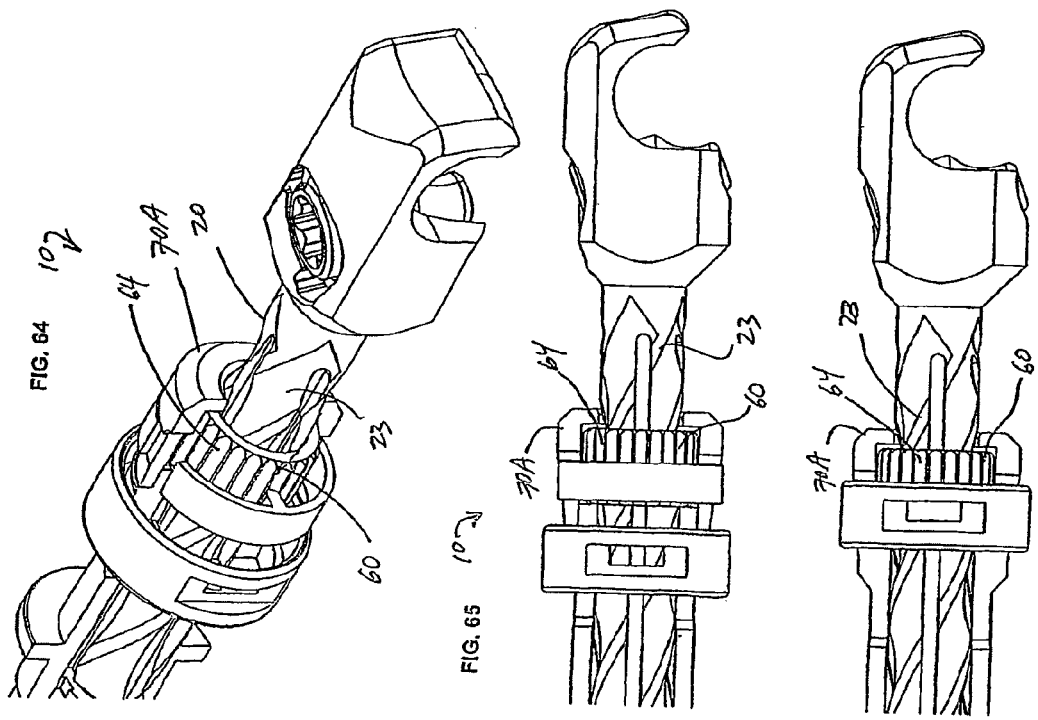

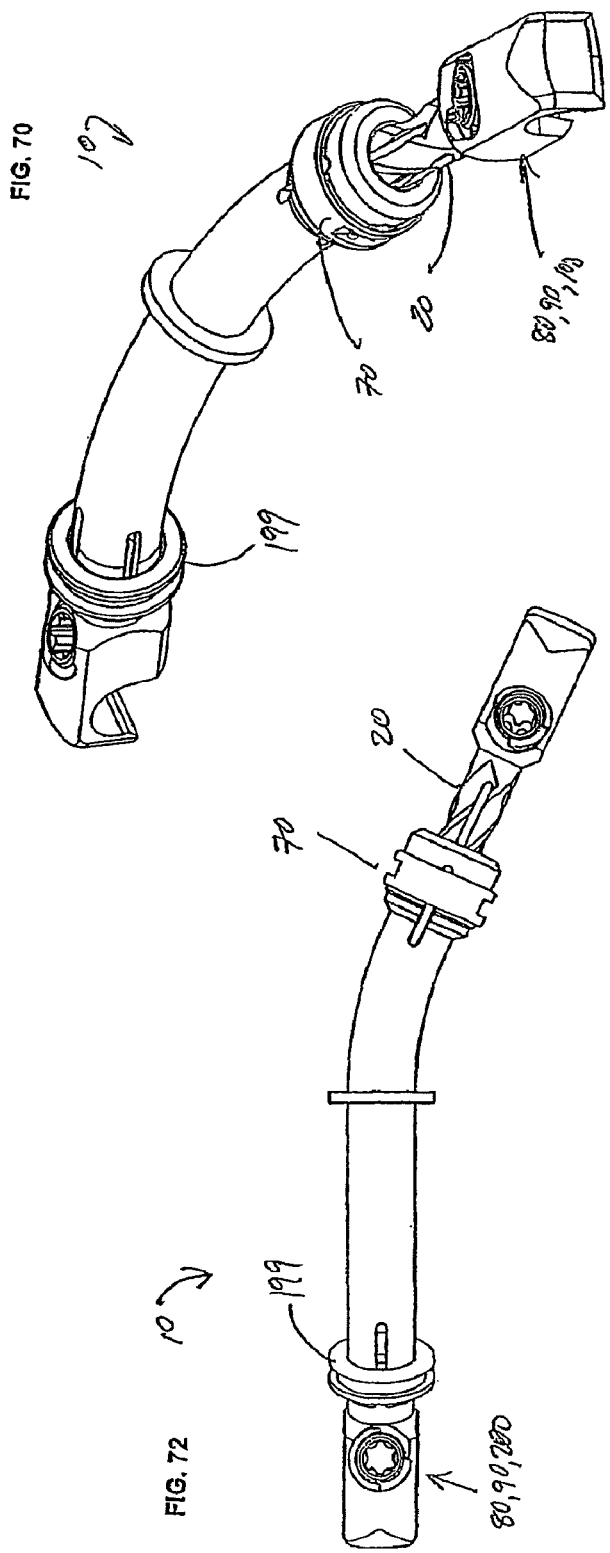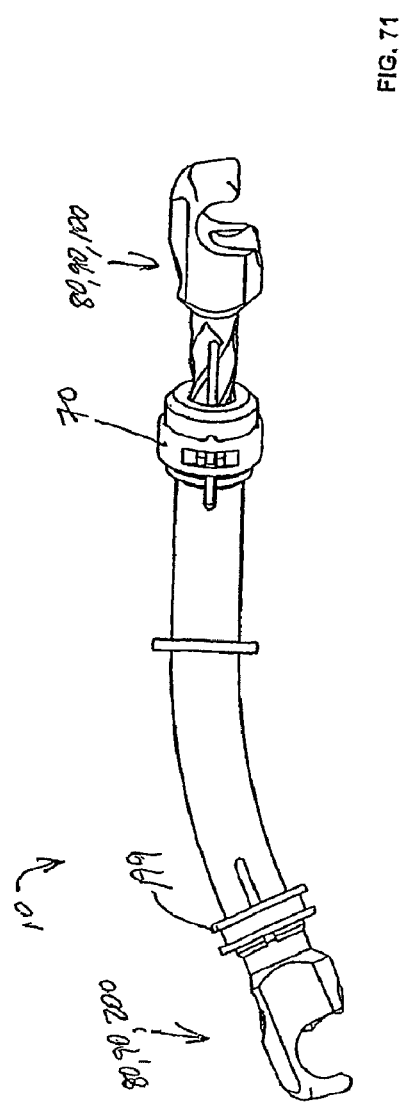

EXPANDABLE CORPECTOMY DEVICE

REFERENCE TO RELATED APPLICATIONS

This application is a continuation-in-part of, and claims priority to and benefit under 35 U.S.C. §120 to copending U.S. patent application Ser. No. 11/327,621, filed on Jan. 6, 2006, which claims, as a continuation, priority to and benefit under 35 U.S.C. §120 to U.S. patent application Ser. No. 10/550,329, filed on Sep. 22, 2005, which is a national phase Application that claims priority to and benefit under 35 U.S.C. §371 to PCT App. No. PCT/US04/008980, filed on Mar. 24, 2004, which claims priority to and benefit under 35 U.S.C. §119(e) to U.S. Provisional App. No. 60/457,158, filed on Mar. 24, 2003, the entire contents of the aforementioned applications are herein incorporated by reference.

TECHNICAL FIELD

The present invention generally relates to a device for spinal fixation.

SUMMARY

An adjustable length corpectomy device is provided with a means for providing bidirectional length adjustment and a means for selectively fixing the length of the implant.

BRIEF DESCRIPTION OF THE ILLUSTRATIONS

The teachings of the present invention can be readily understood by considering the following detailed description in conjunction with the accompanying drawings.

FIG. 3 is a perspective view of a connector according to an embodiment of the invention having one fixed jaw and one articulating jaw.

FIG. 4 is a top plan view of the connector shown in FIG. 3.

FIG. 5 is a side elevation view of the connector shown in FIG. 3.

FIG. 7 is a perspective view of the two-piece body of a connector according to an embodiment of the invention.

FIG. 8 is a section view of the connector shown in FIG. 7.

FIG. 9 is a side elevation view of the connector shown in FIG. 7.

FIG. 10 is an end view of the connector shown in FIG. 7 looking into the second axial opening.

FIG. 11 is a perspective view of a rotor according to an embodiment of the invention.

FIG. 12 is a side elevation view of the rotor shown in FIG. 11.

FIG. 13 is an end view of the rotor shown in FIG. 11.

FIG. 14 is a side elevation view in section of the rotor shown in FIG. 11.

FIG. 22 is a perspective view of a locking cam according to an embodiment of the invention.

FIG. 23 is a driving end axial view of the locking cam of FIG. 22.

FIG. 24 is a side elevation view of the locking cam of FIG. 22.

FIG. 25 is a bottom elevation view of the locking cam of FIG. 22.

FIG. 26 is an engaging end axial view of the locking cam of FIG. 22.

FIG. 27 is a perspective view of a connector according to an alternative embodiment of the invention.

FIG. 28 is a top plan view of the connector shown in FIG. 27.

FIG. 29 is a side elevation view of the connector shown in FIG. 27.

FIG. 30 is an end elevation view of the connector shown in FIG. 27.

FIG. 45 is a perspective view of a connector according to an alternative embodiment wherein the housing and the extending shaft are bent.

FIG. 46 is a front elevation view of the connector shown in FIG. 45.

FIG. 64 is a partial perspective view of an alternative embodiment of the invention utilizing a helical ratcheting extending shaft, shown in an unlocked position.

FIG. 65 is a side elevation view of the connector shown in FIG. 64.

FIG. 66 is a partial perspective view of the connector shown in FIG. 64, but shown in a locked position.

FIG. 67 is a side elevation view of the connector shown in FIG. 66.

FIG. 70 is a perspective view of an alternative embodiment of the invention employing a housing bent in multiple planes.

FIG. 71 is a side elevation view of the connector shown in FIG. 70.

FIG. 72 is a top view of the connector shown in FIG. 70.

Figure 74A:
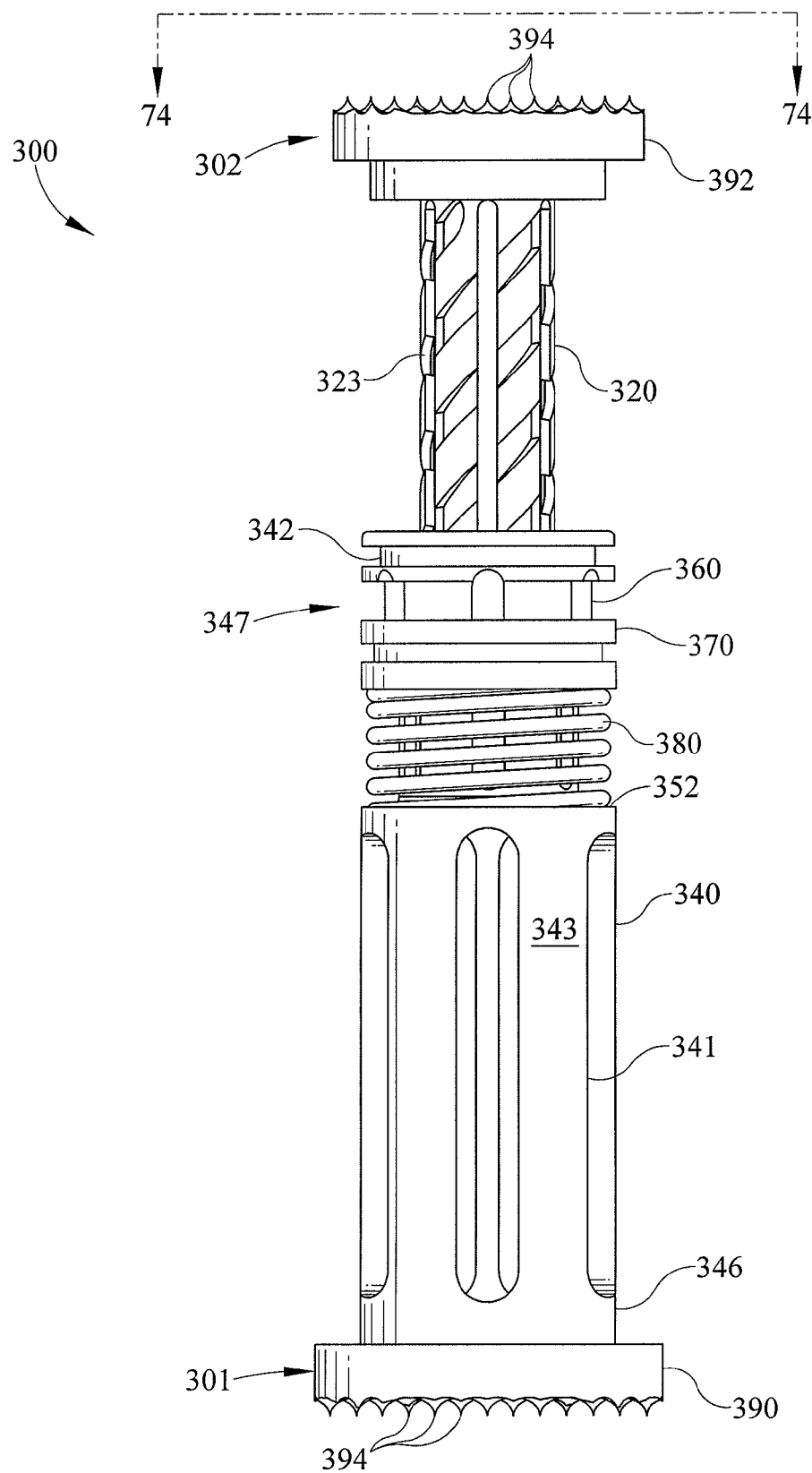
Figure 74B:
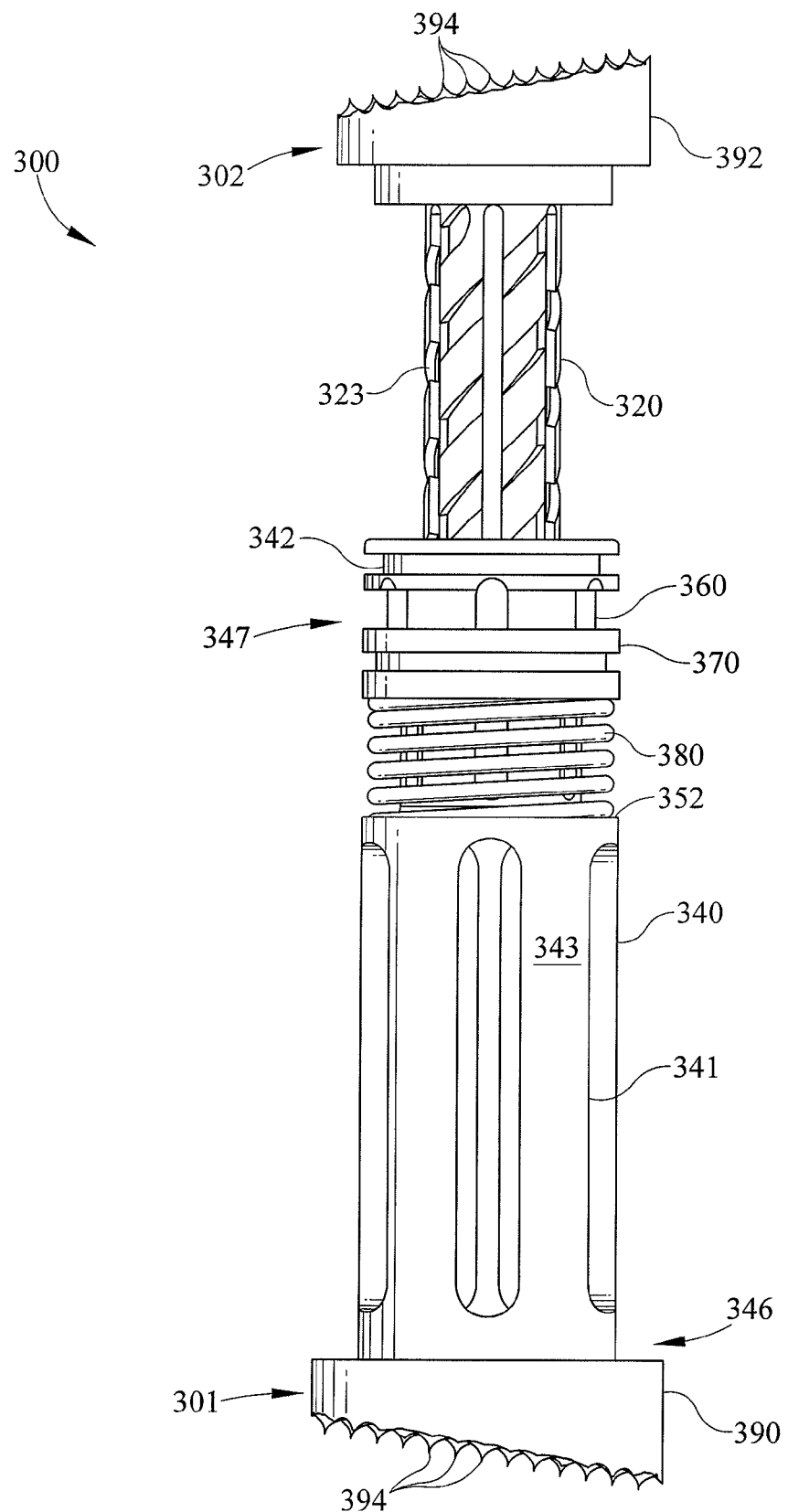
Figure 75:
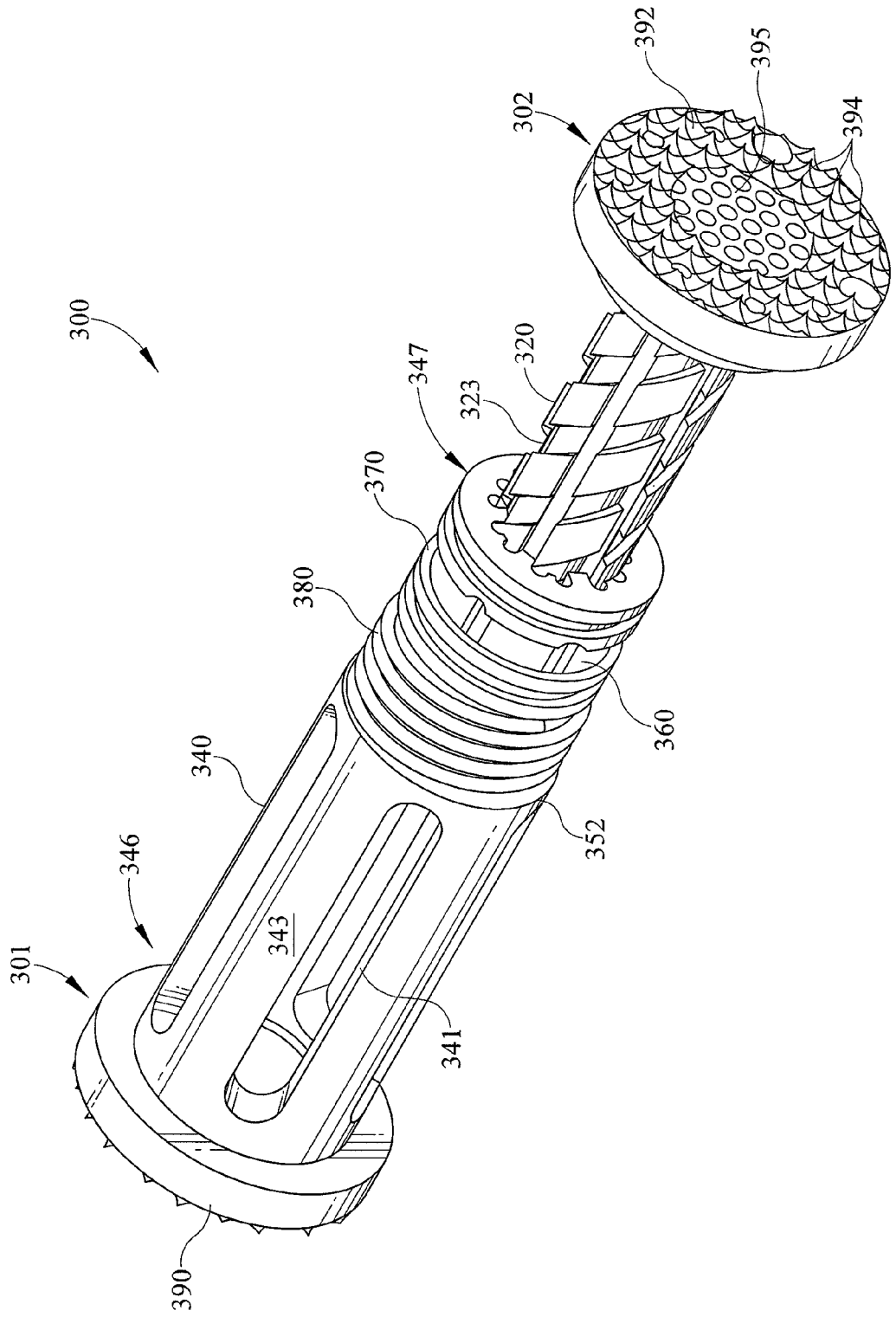

FIGS. 74a, 74b, and 75 are views of an embodiment of an adjustable corpectomy device in a second position.

Figure 76:
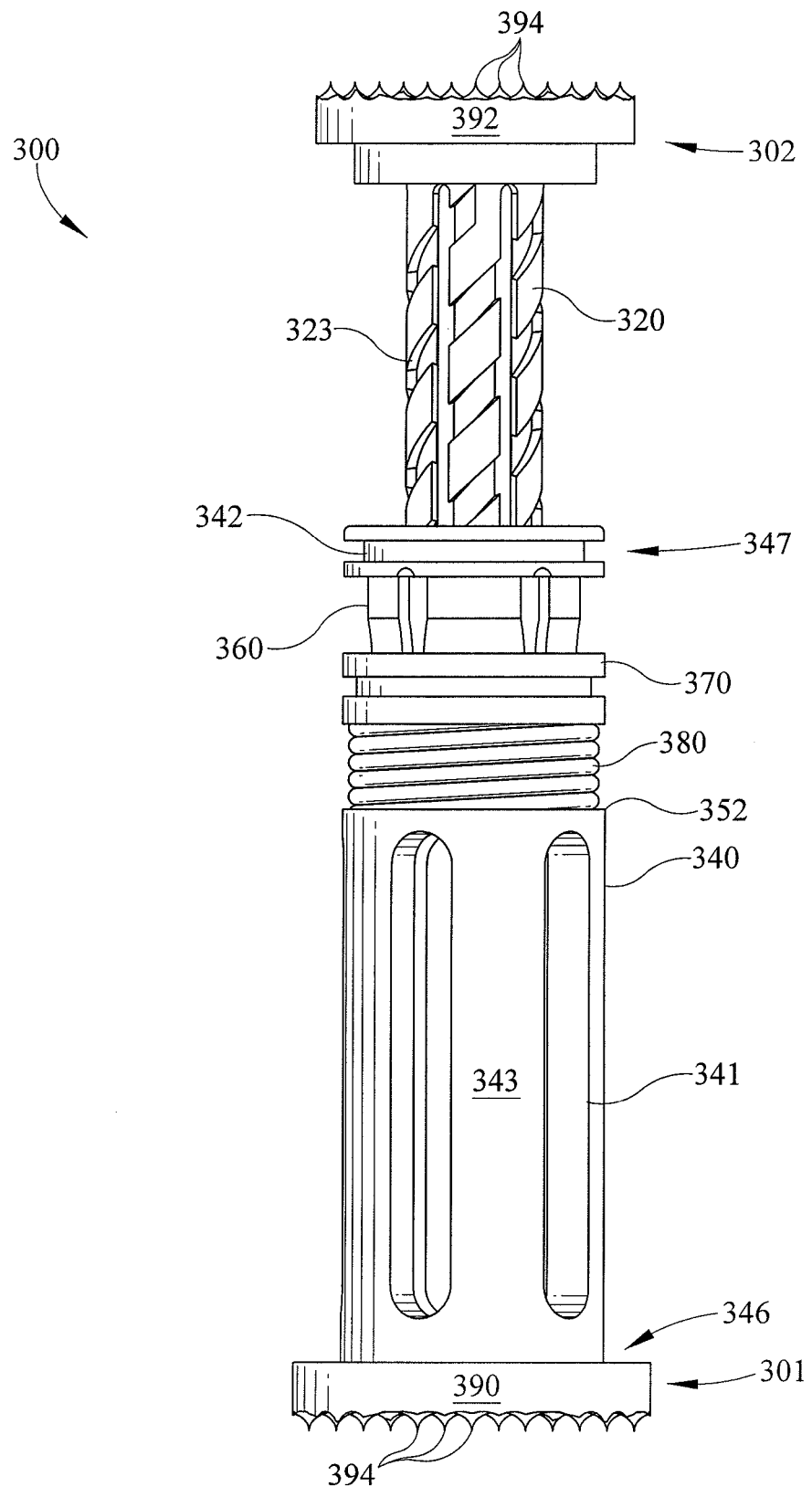

FIG. 76 is a side view of an embodiment of an adjustable corpectomy device in a first position.

Figure 73:
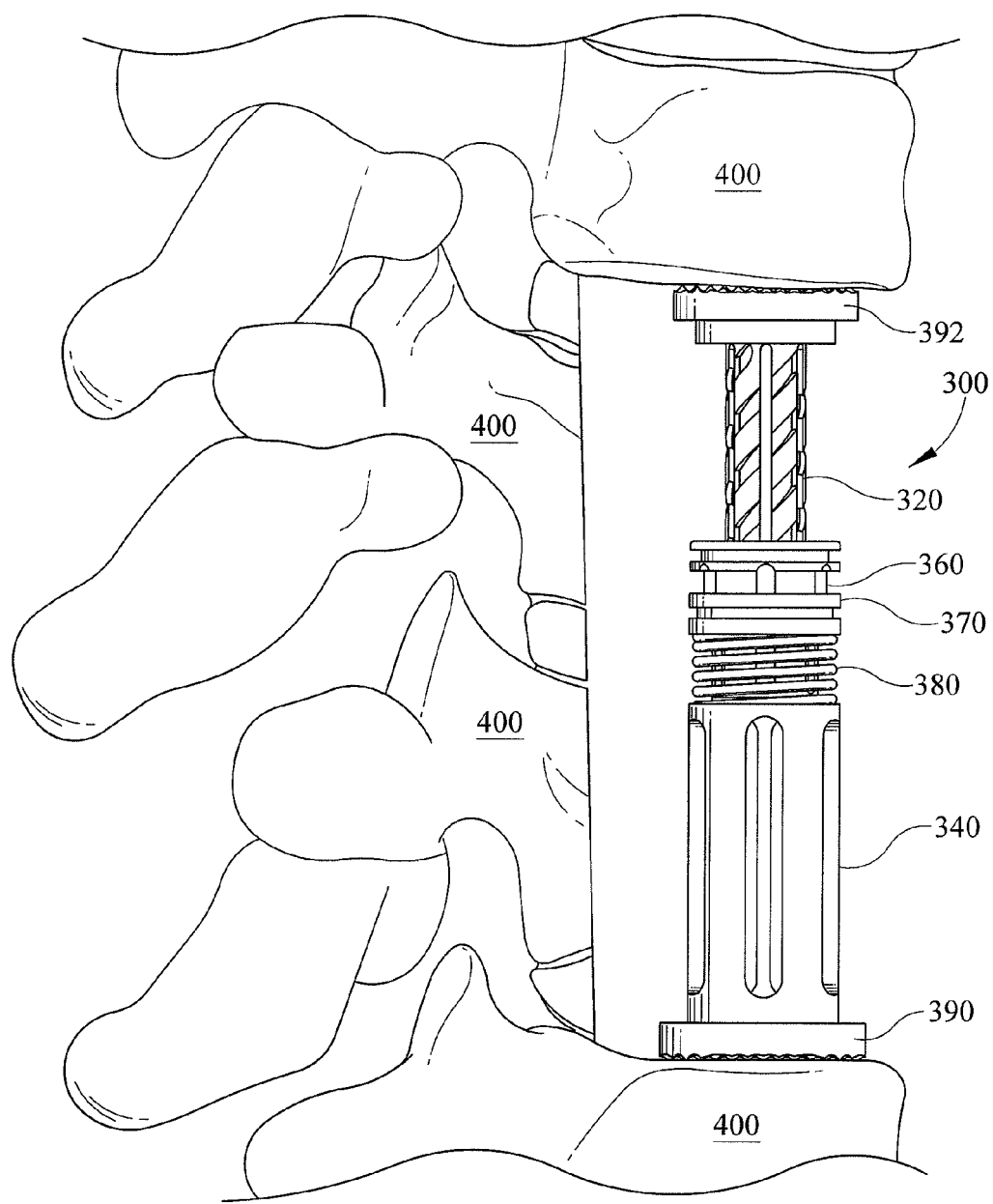
FIG. 73 is a side view of an embodiment of an adjustable corpectomy device implanted in a patient.
Figure 77:
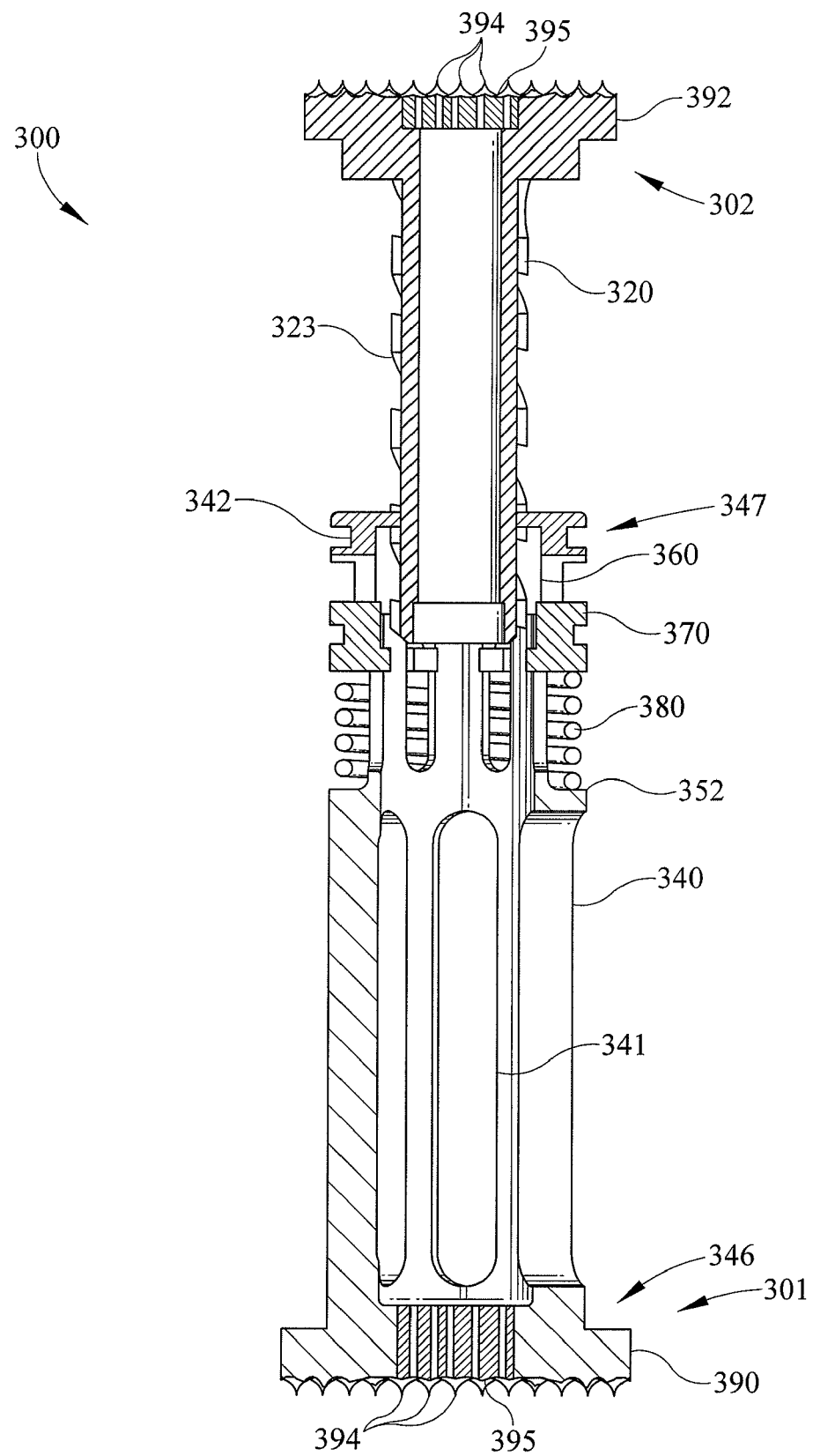

FIG. 77 is a cross-sectional view of the embodiment of FIG. 73, shown along line 74-74.

Figure 78:
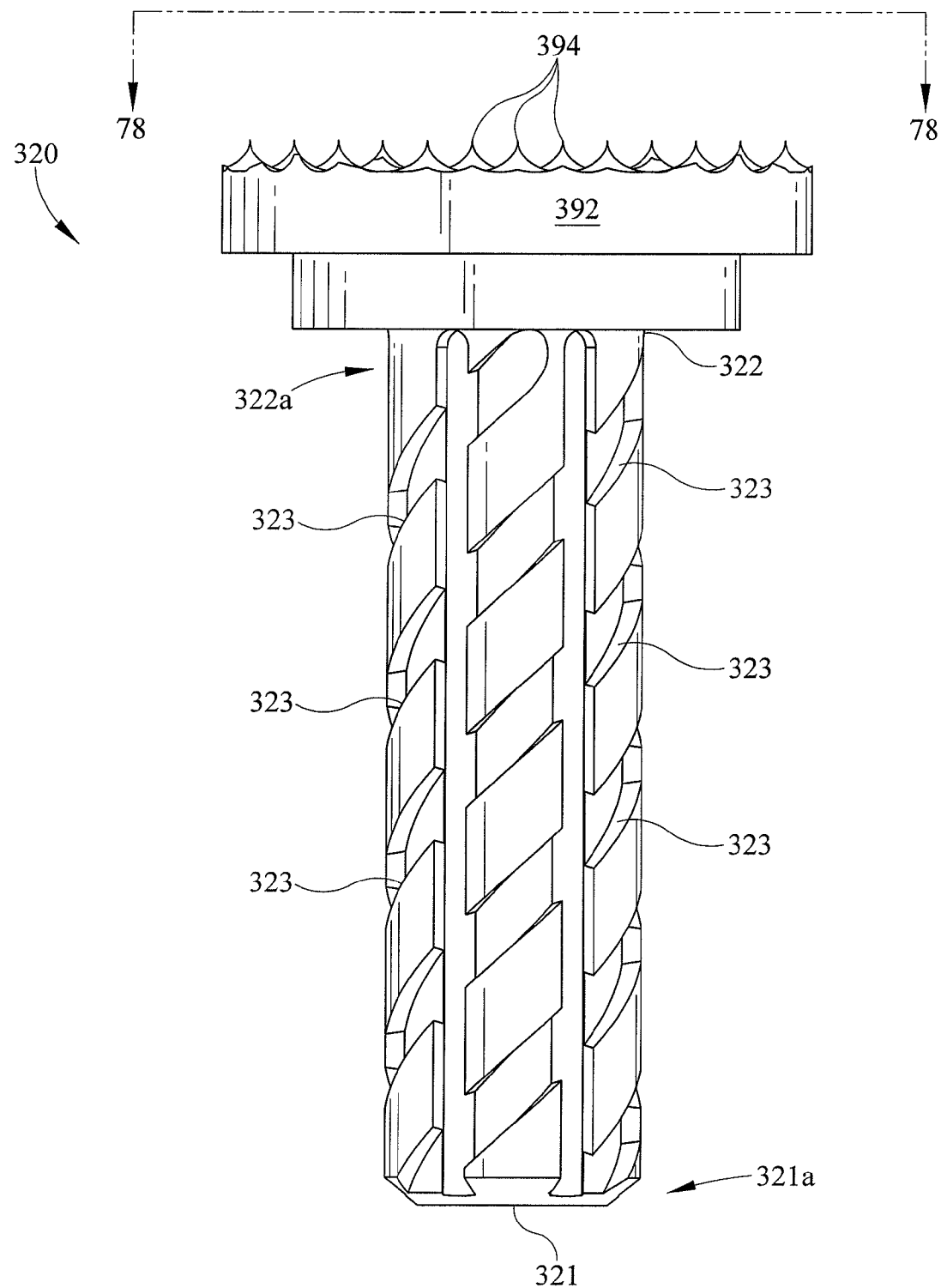
Figure 79:
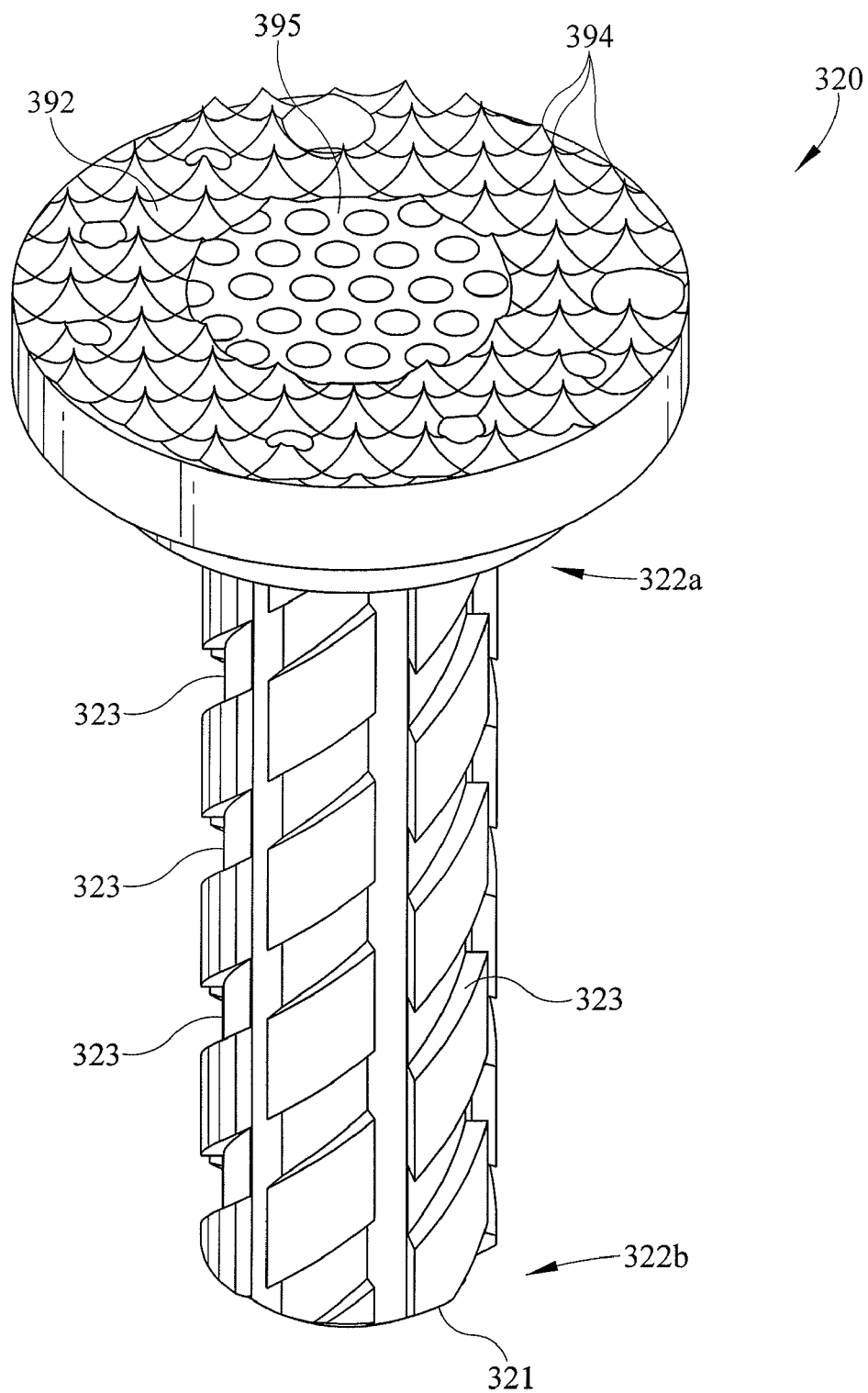

FIGS. 78 and 79 are views of an embodiment of a first cage, as shown in FIGS. 73-77.

Figure 80:
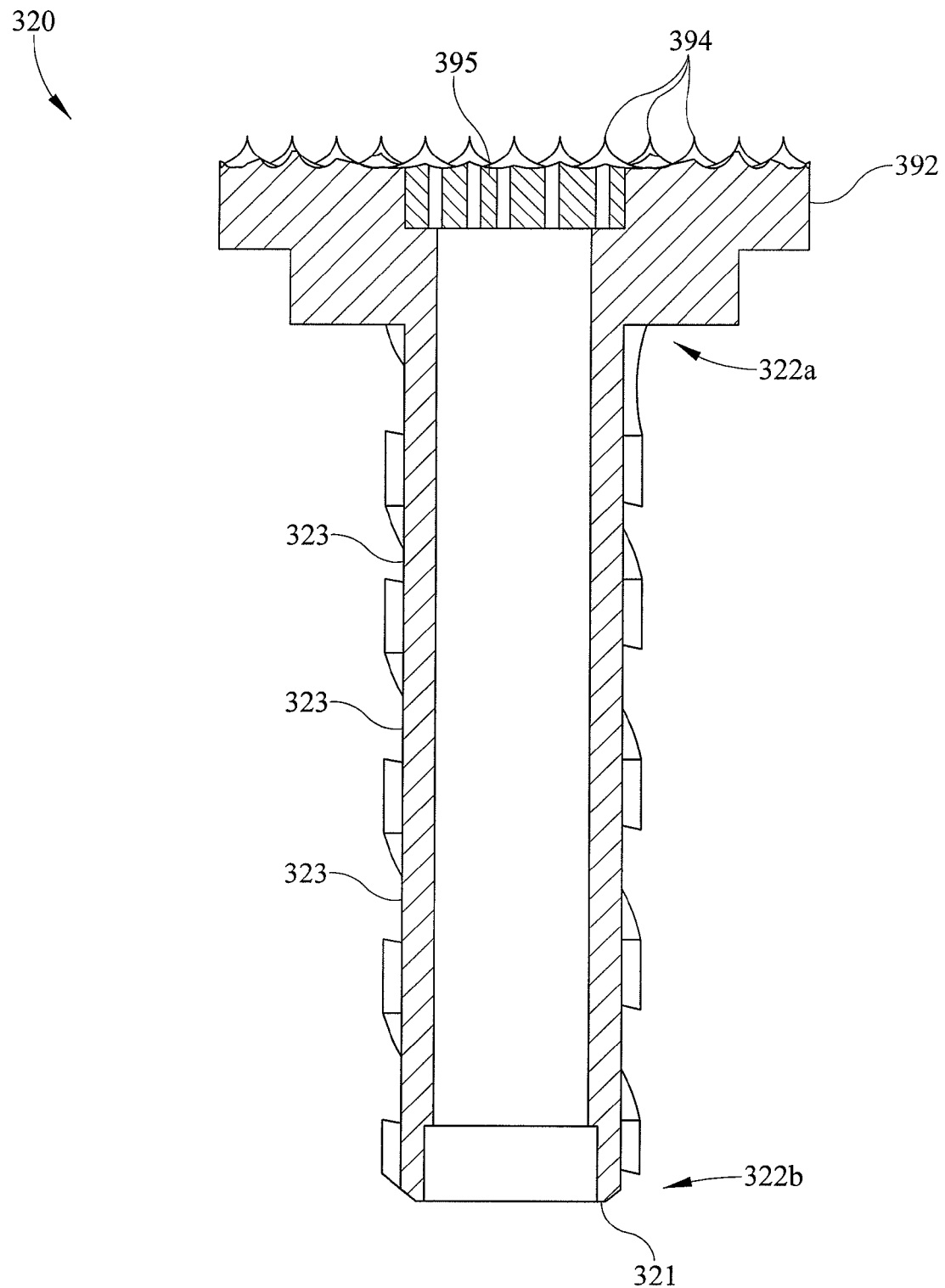

FIG. 80 is a cross-sectional view of the embodiment of the first cage of FIG. 78, shown along line 78-78.

Figure 81:
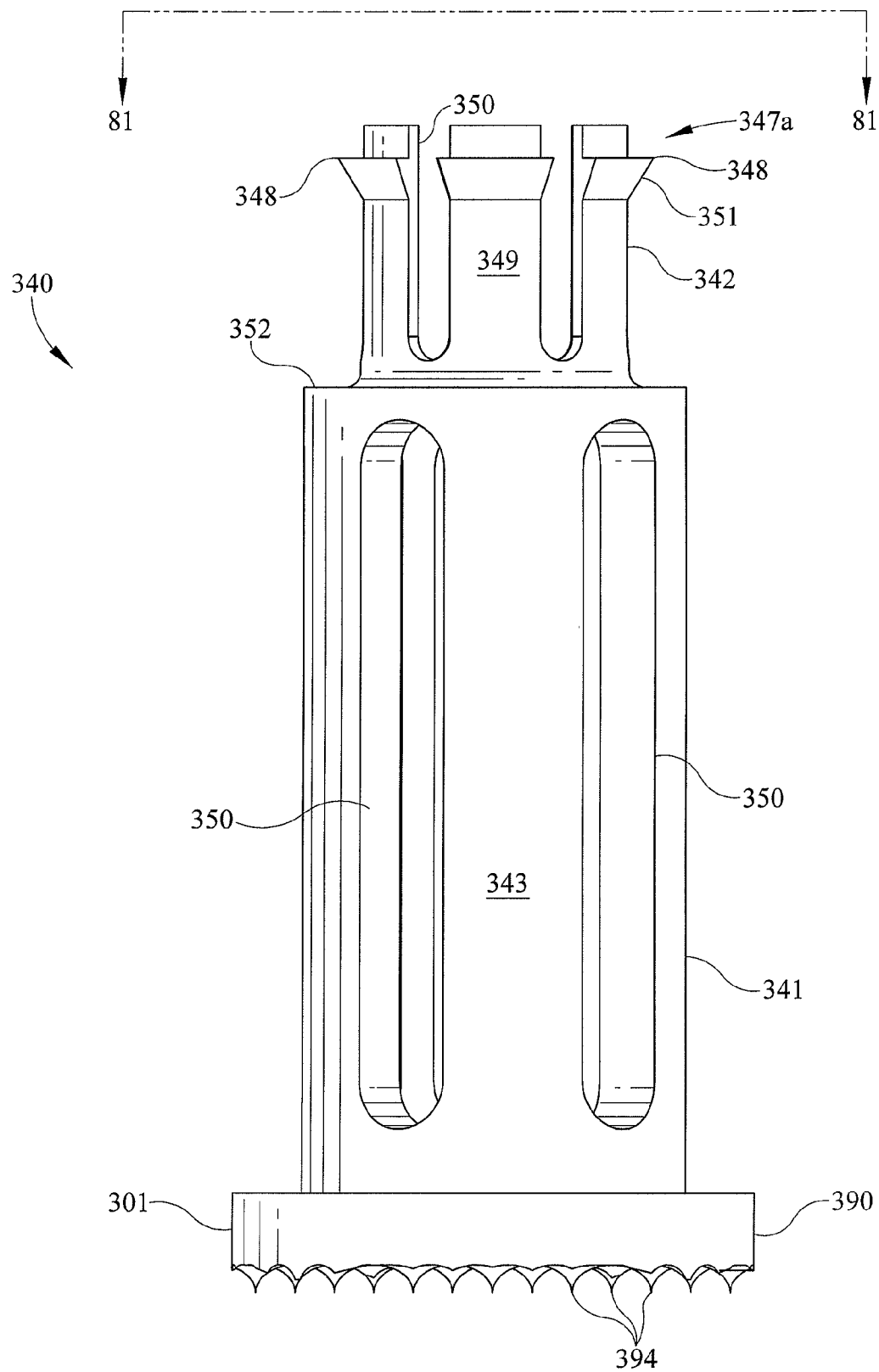
Figure 82:
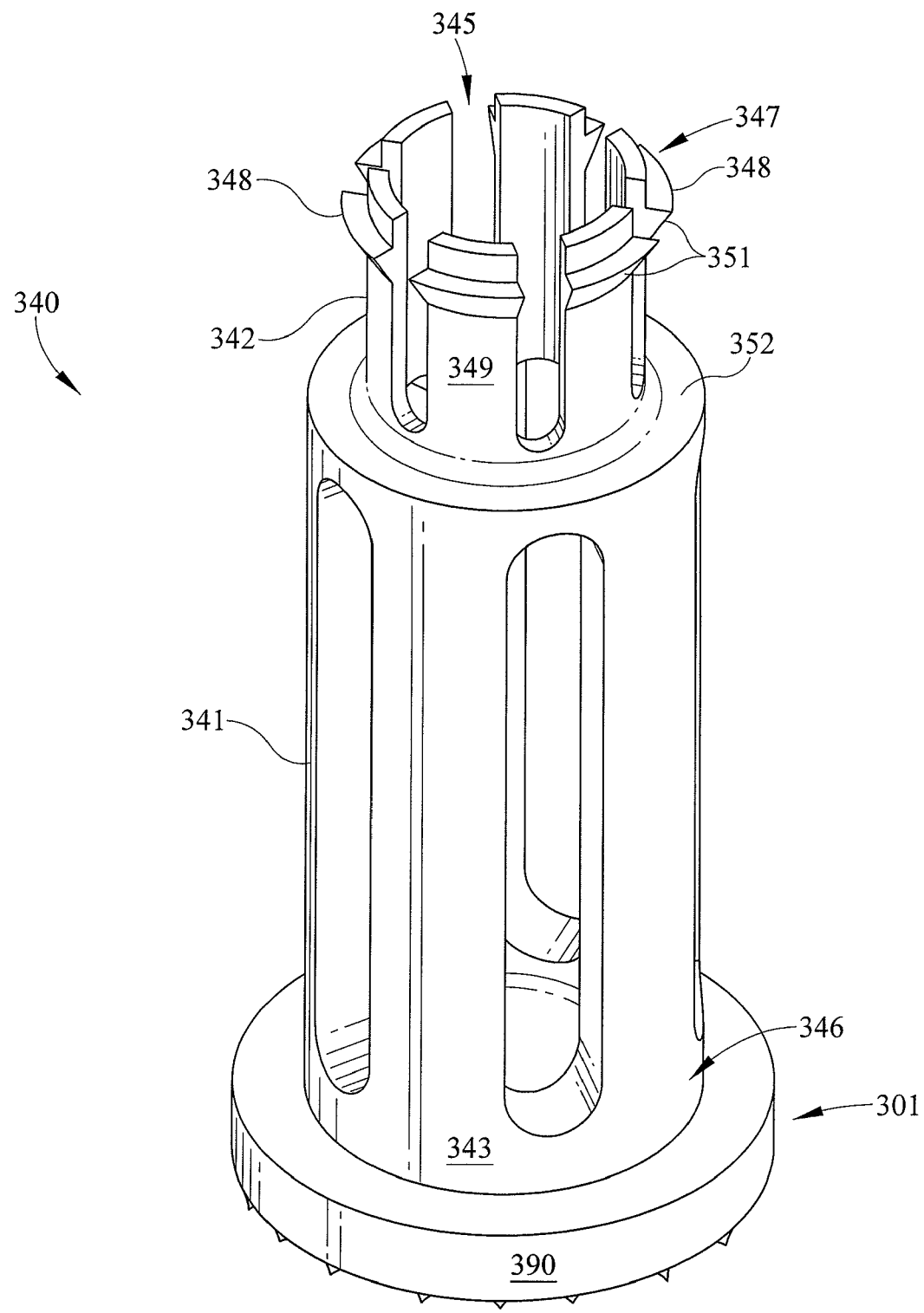

FIGS. 81 and 82 are views of an embodiment of a second cage, as shown in FIGS. 73-77.

Figure 83:
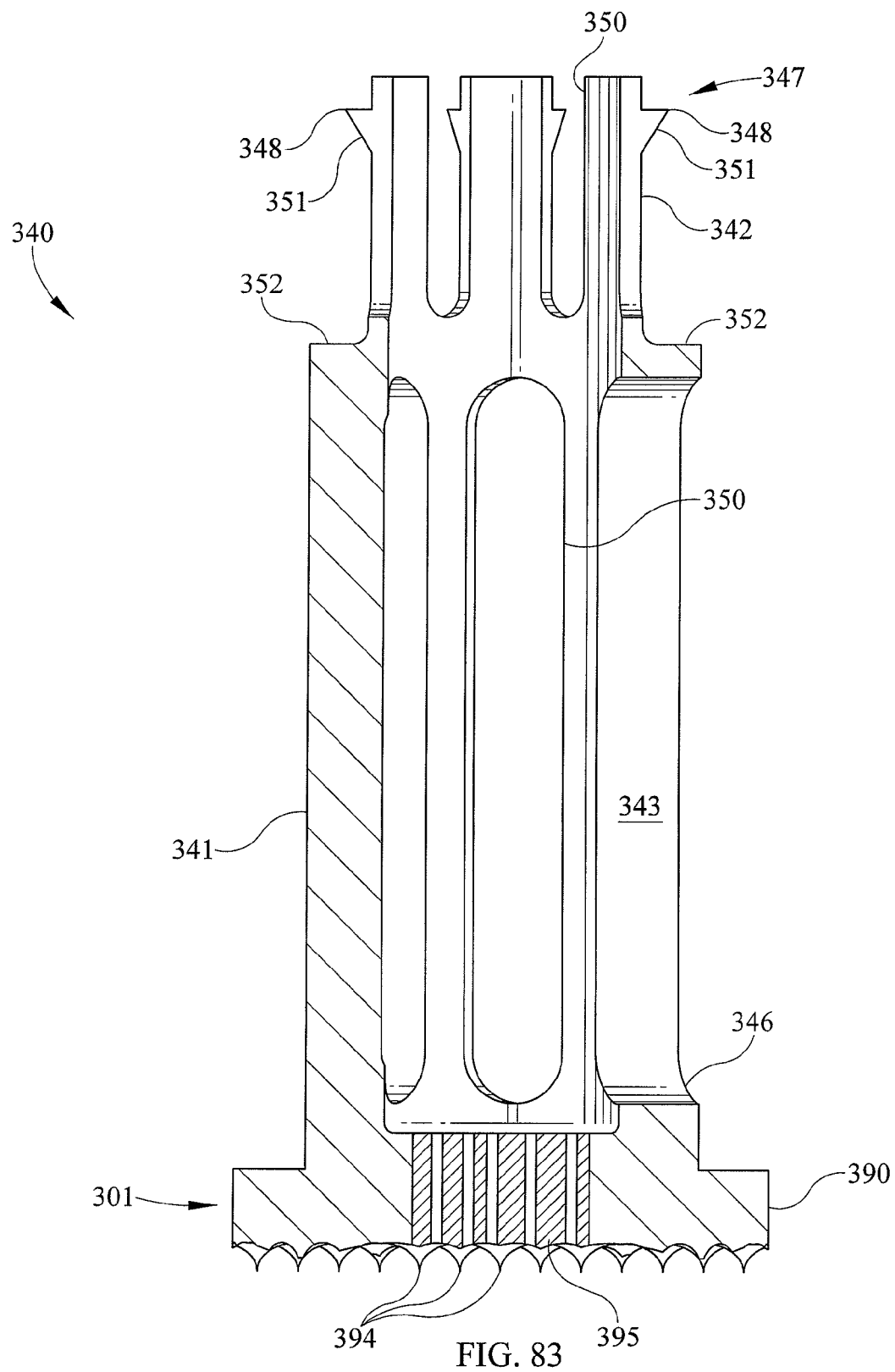

FIG. 83 is a cross-sectional view of the embodiment of the second cage of FIG. 81, shown along line 81-81.

Figure 84:
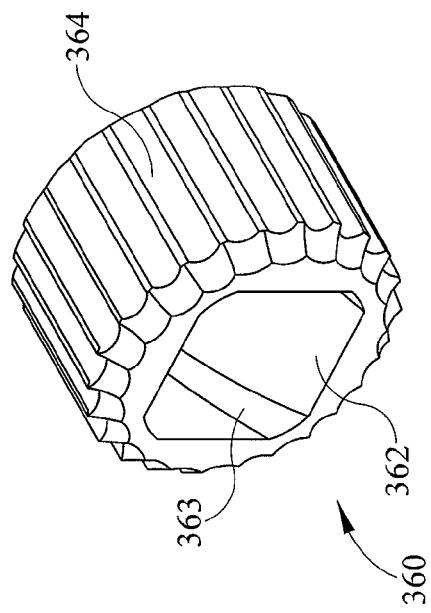

FIG. 84 is a perspective view of a rotor according to an embodiment of the invention.

Figure 85:
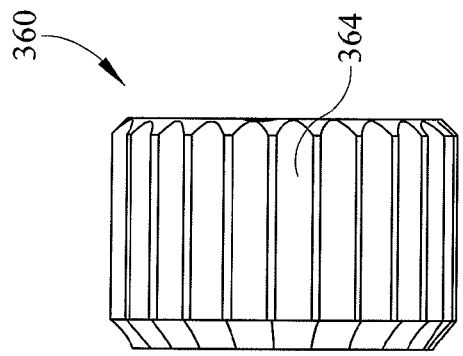

FIG. 85 is a side elevation view of the rotor shown in FIG. 84.

Figure 86:
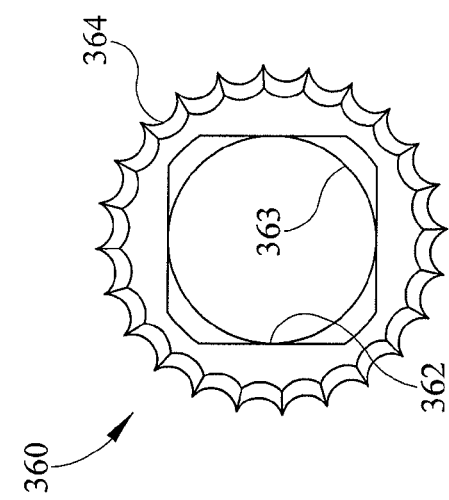

FIG. 86 is an end view of the rotor shown in FIG. 84.

Figure 87:
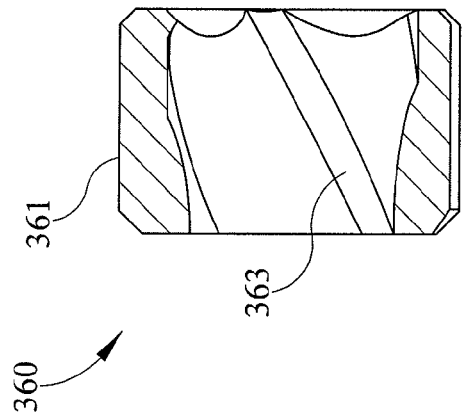

FIG. 87 is a side elevation view in section of the rotor shown in FIG. 84.

Figure 88:
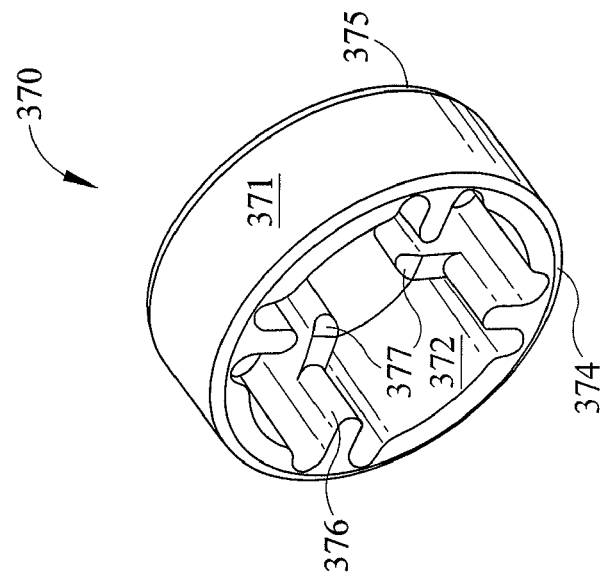

FIG. 88 is a perspective view of a locking collar according to an embodiment of the invention.

Figure 89:
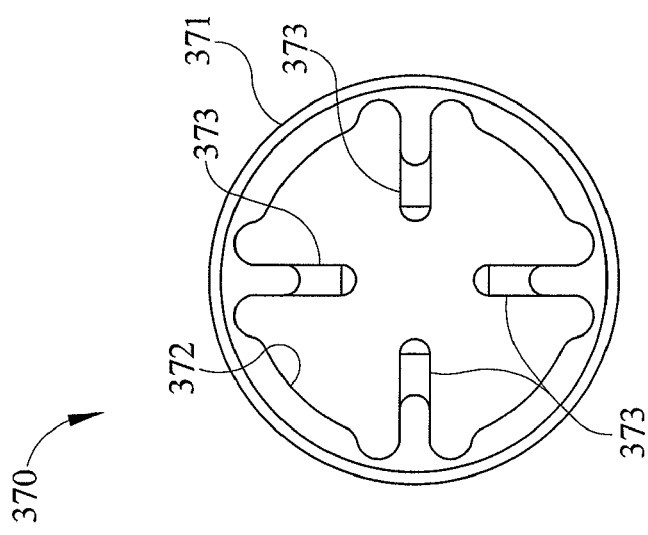

FIG. 89 is an end view of the locking collar shown in FIG. 88.

Figure 90:
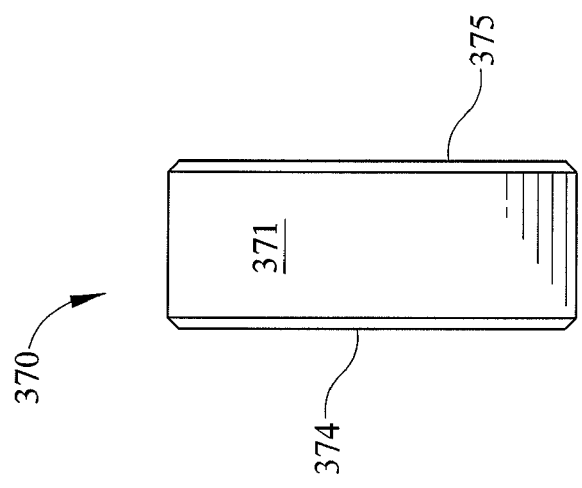

FIG. 90 is a side elevation view of the locking collar shown in FIG. 88.

Figure 91:
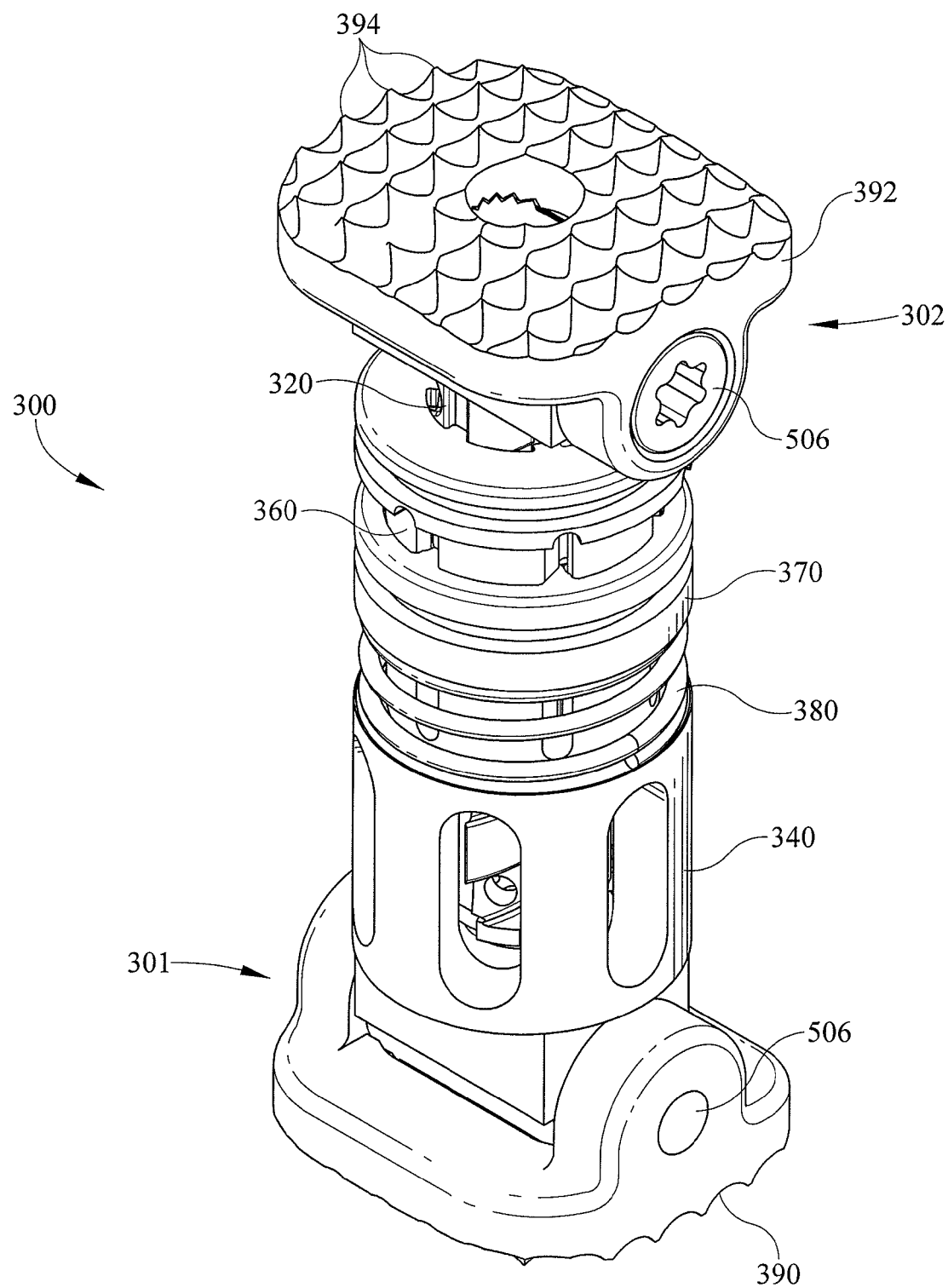

FIG. 91 is a perspective view of an embodiment of the invention.

Figure 92:
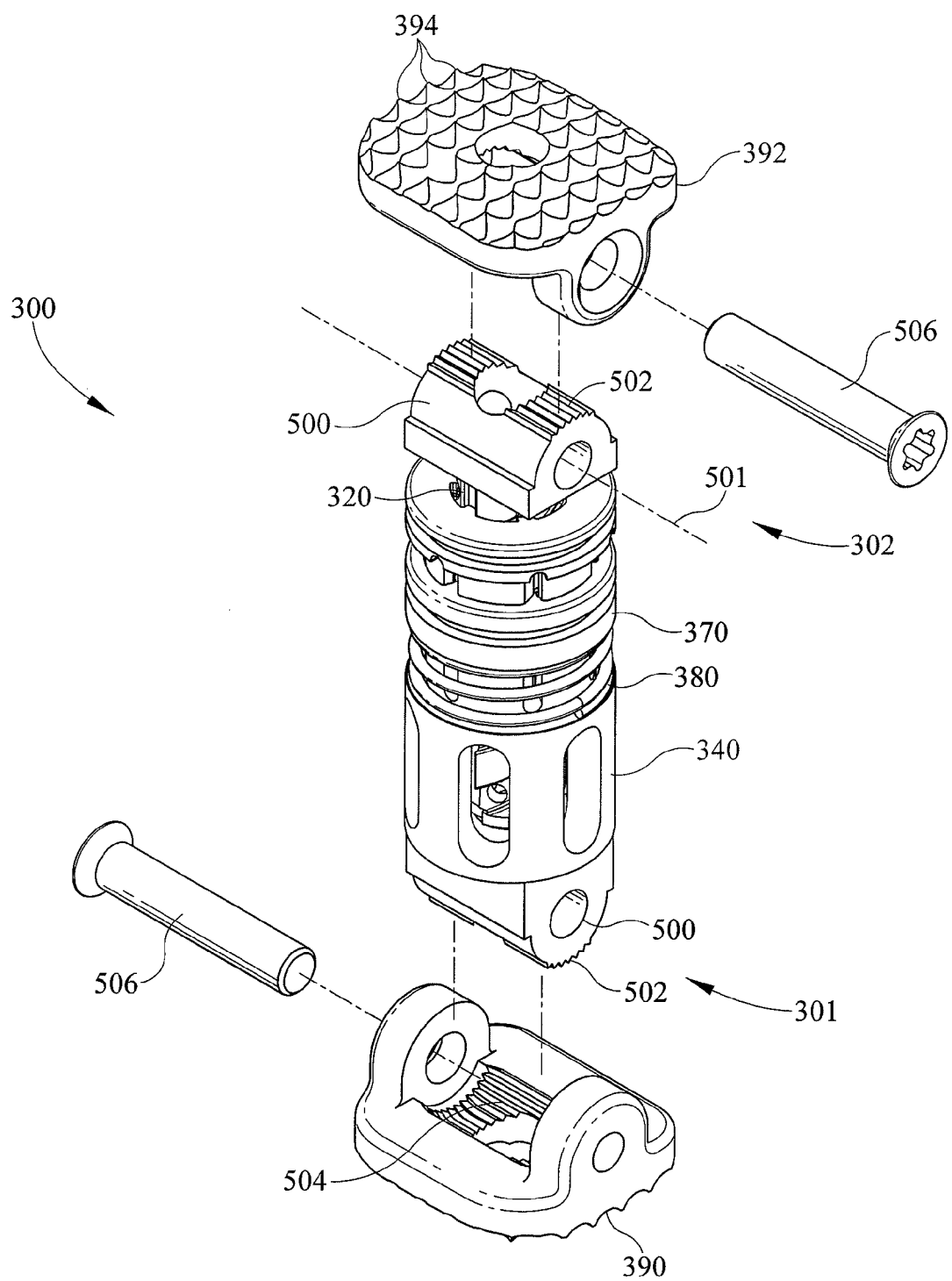

FIG. 92 is an exploded assembly view of the embodiment shown in FIG. 91.

Figure 93:
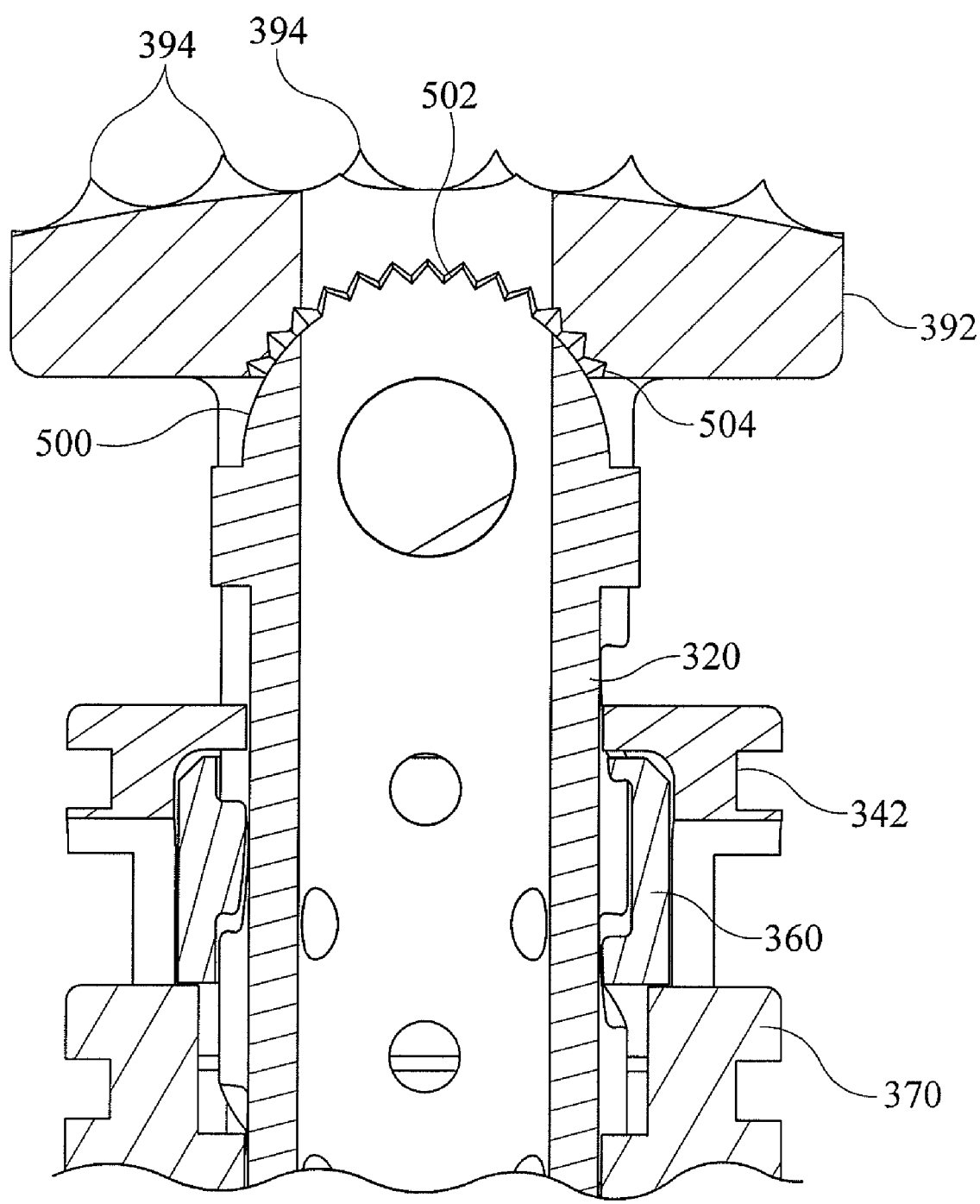

FIG. 93 is a cross-sectional view of the embodiment shown in FIG. 91.

Figure 94:
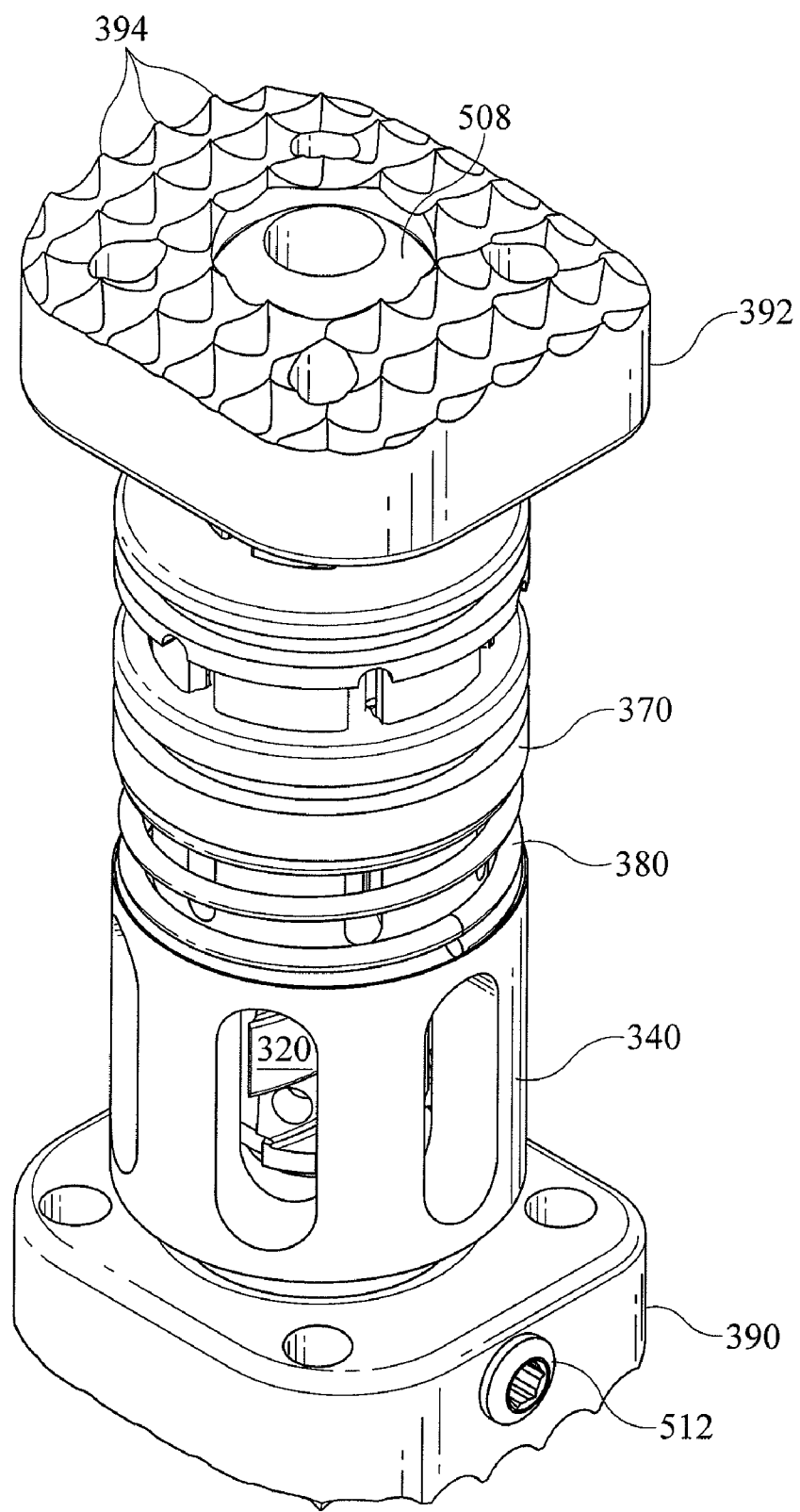

FIG. 94 is a perspective view of an embodiment of the invention.

Figure 95:
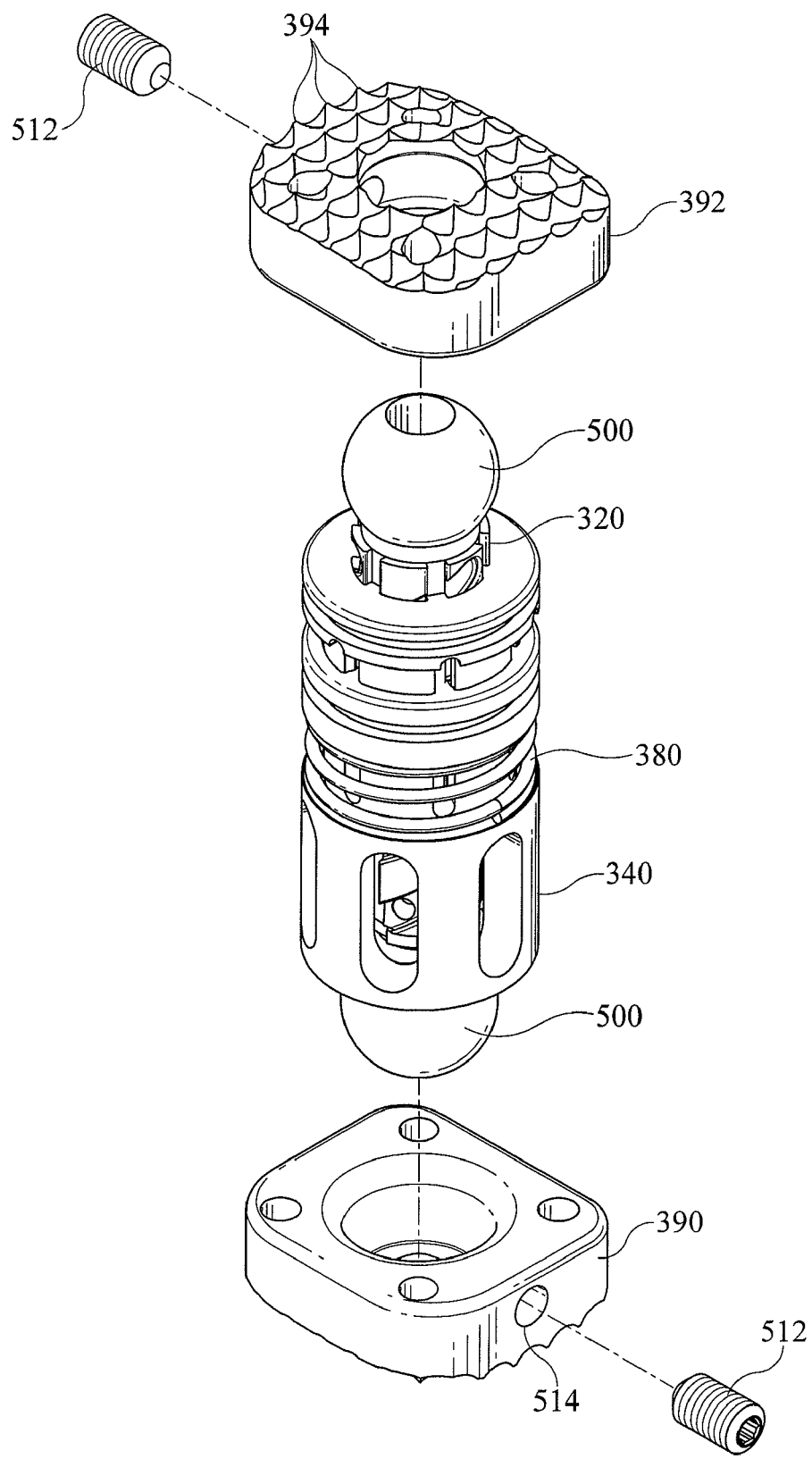

FIG. 95 is an exploded assembly view of the embodiment shown in FIG. 94.

Figure 96:
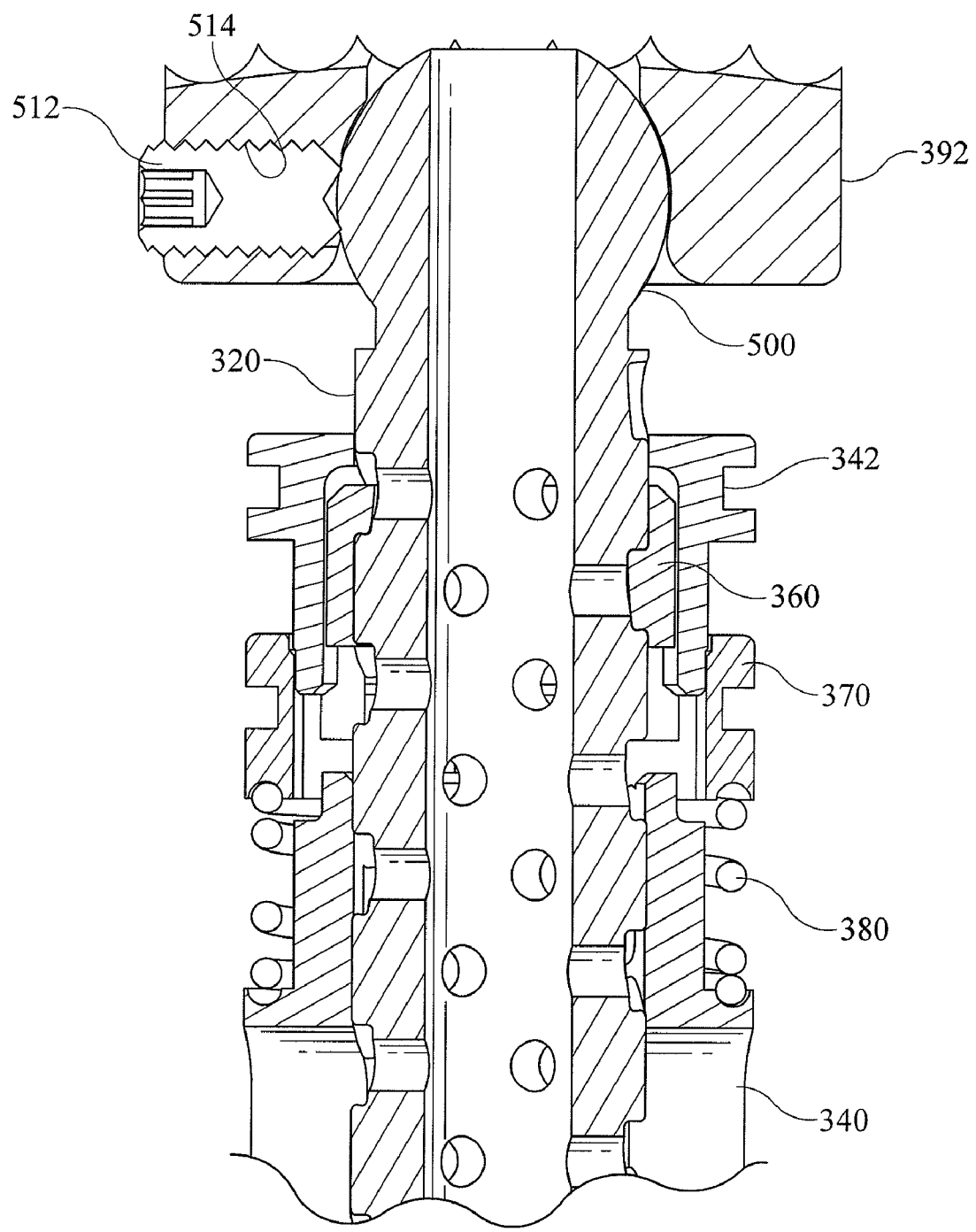

FIG. 96 is a cross-sectional view of the embodiment shown in FIG. 94.

Figure 97:
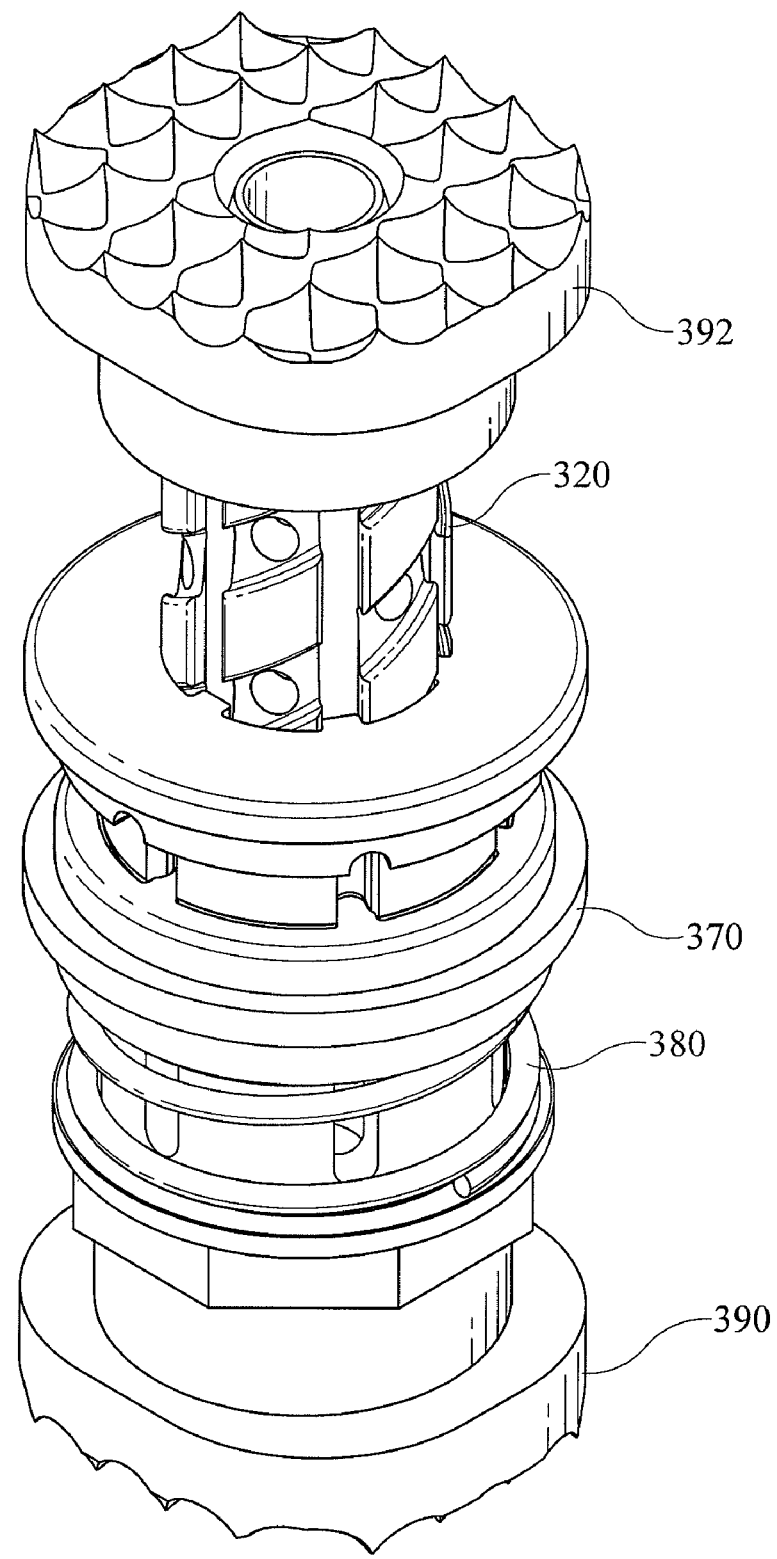

FIG. 97 is a perspective view of an embodiment of the invention.

Figure 98:
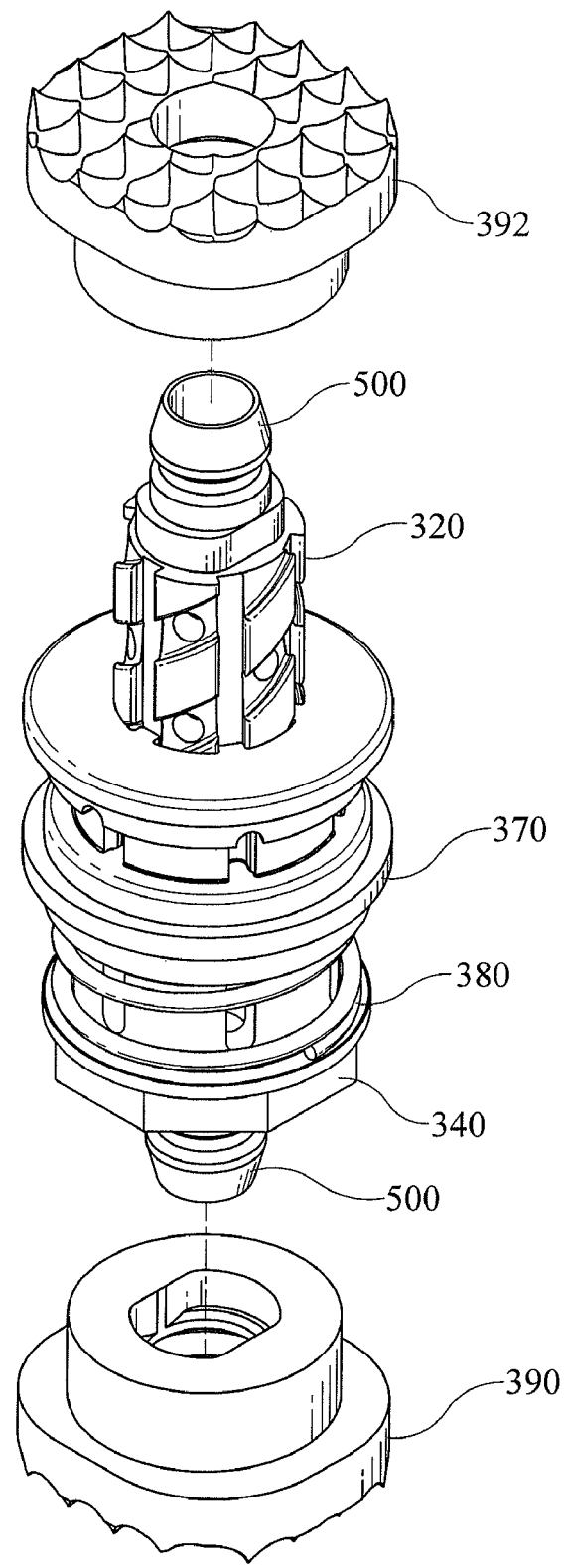

FIG. 98 is an exploded assembly view of the embodiment shown in FIG. 97.

Figure 99:
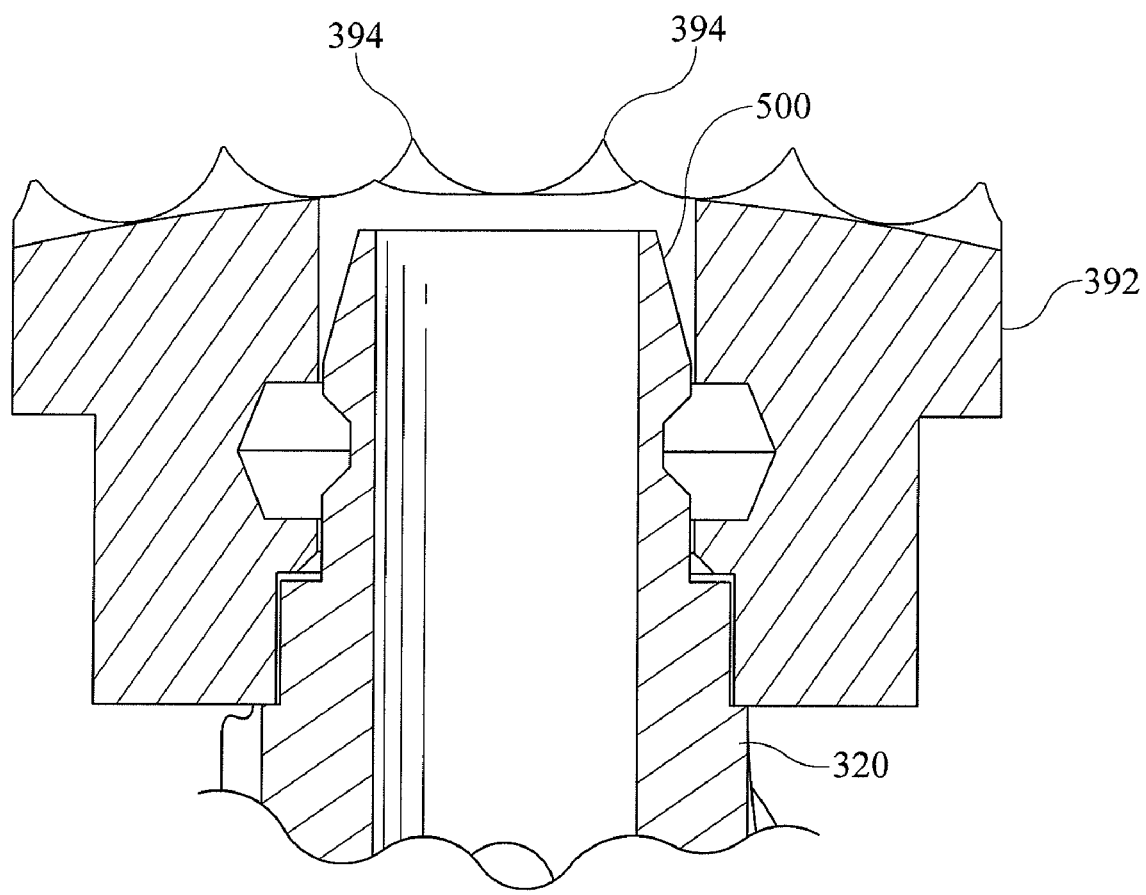

FIG. 99 is a cross-sectional view of the embodiment shown in FIG. 97.

DETAILED DESCRIPTION

While the present invention will be described more fully hereinafter with reference to the accompanying drawings, in which particular embodiments and methods are shown, it is to be understood from the outset that persons of ordinary skill in the art may modify the invention herein described while achieving the functions and results of this invention. Accordingly, the description that follows is to be understood as illustrative and exemplary of specific embodiments within the broad scope of the present invention and not as limiting the scope of the invention. In the following descriptions, like numbers refer to similar features or like elements throughout. As stated before, the invention is usable in a variety of medical applications and indeed is not limited to spinal applications. The invention will be denoted as connector 10, it being understood that a variety of implant locations are possible. For ease of understanding, however, since spinal applications currently see great benefit from the invention, the following description is made with reference to spinal applications.

Figure 1:
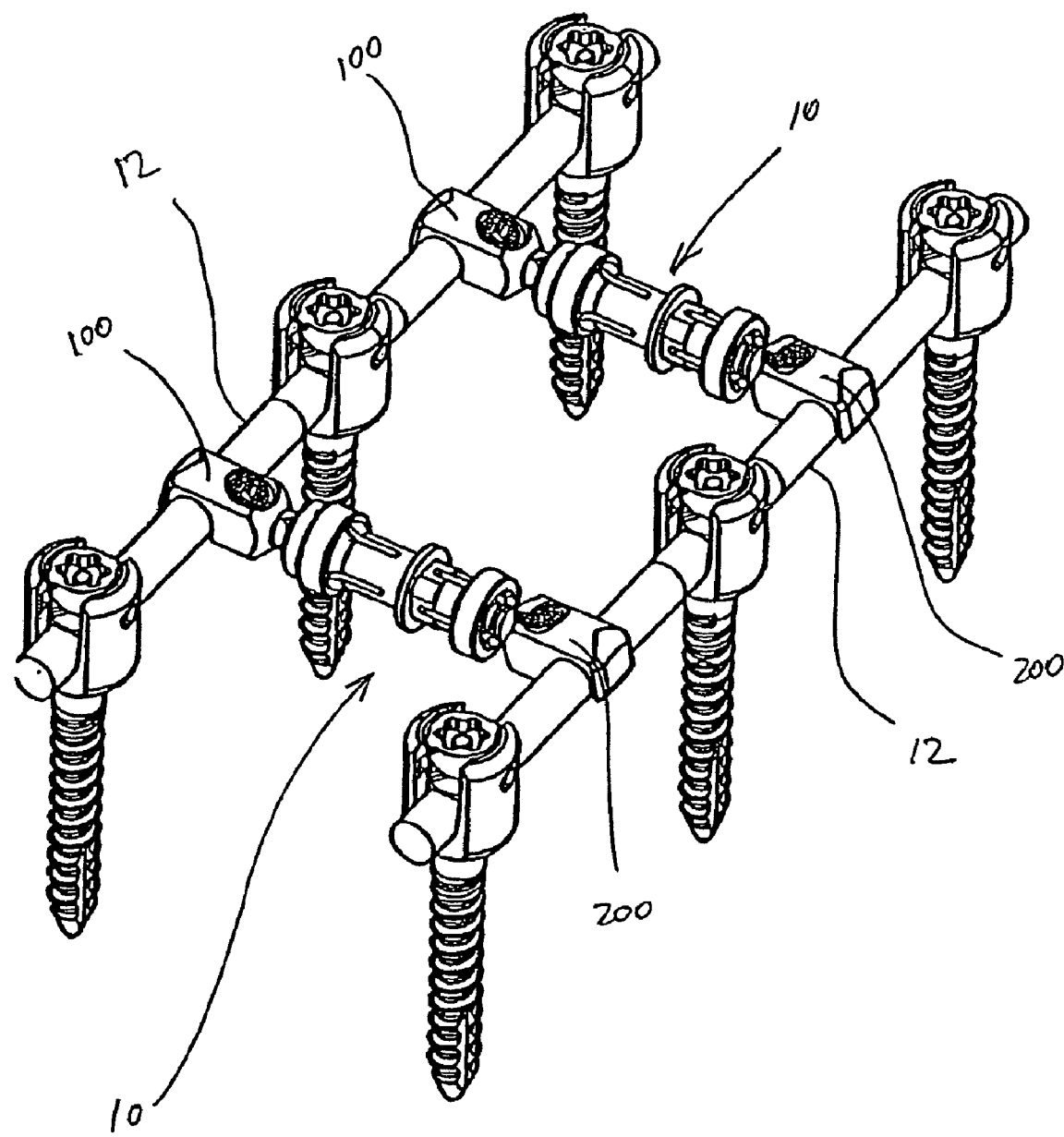
FIG. 1 is a perspective view of the apparatus according to one embodiment showing two connectors of the invention being used to connect two surgical rods secured to multiple bone anchors.
Figure 2:
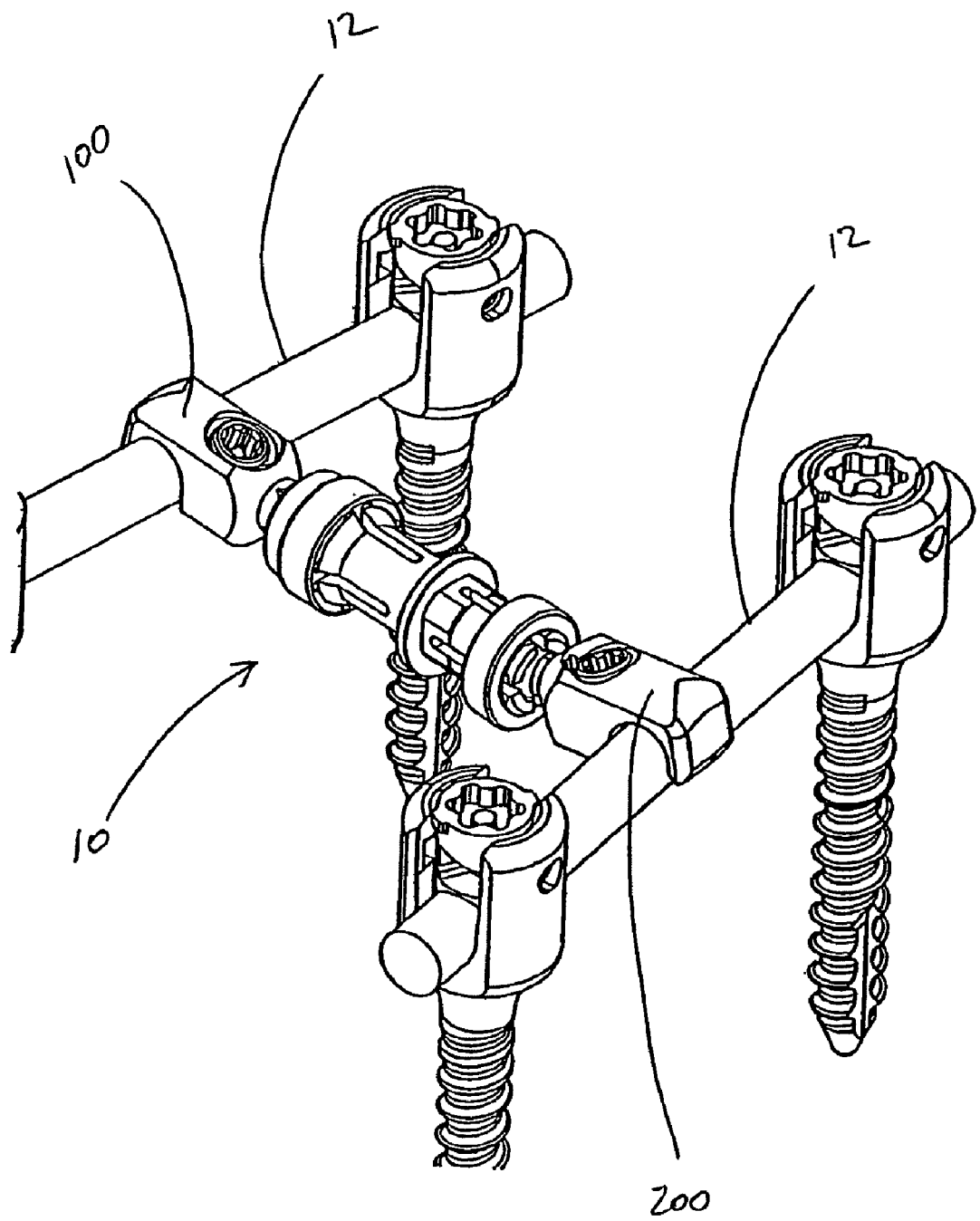
FIG. 2 is a close-up perspective of a connector according to one embodiment wherein the connector further comprises an articulating jaw that is securing two non-parallel surgical rods.
Figure 6:
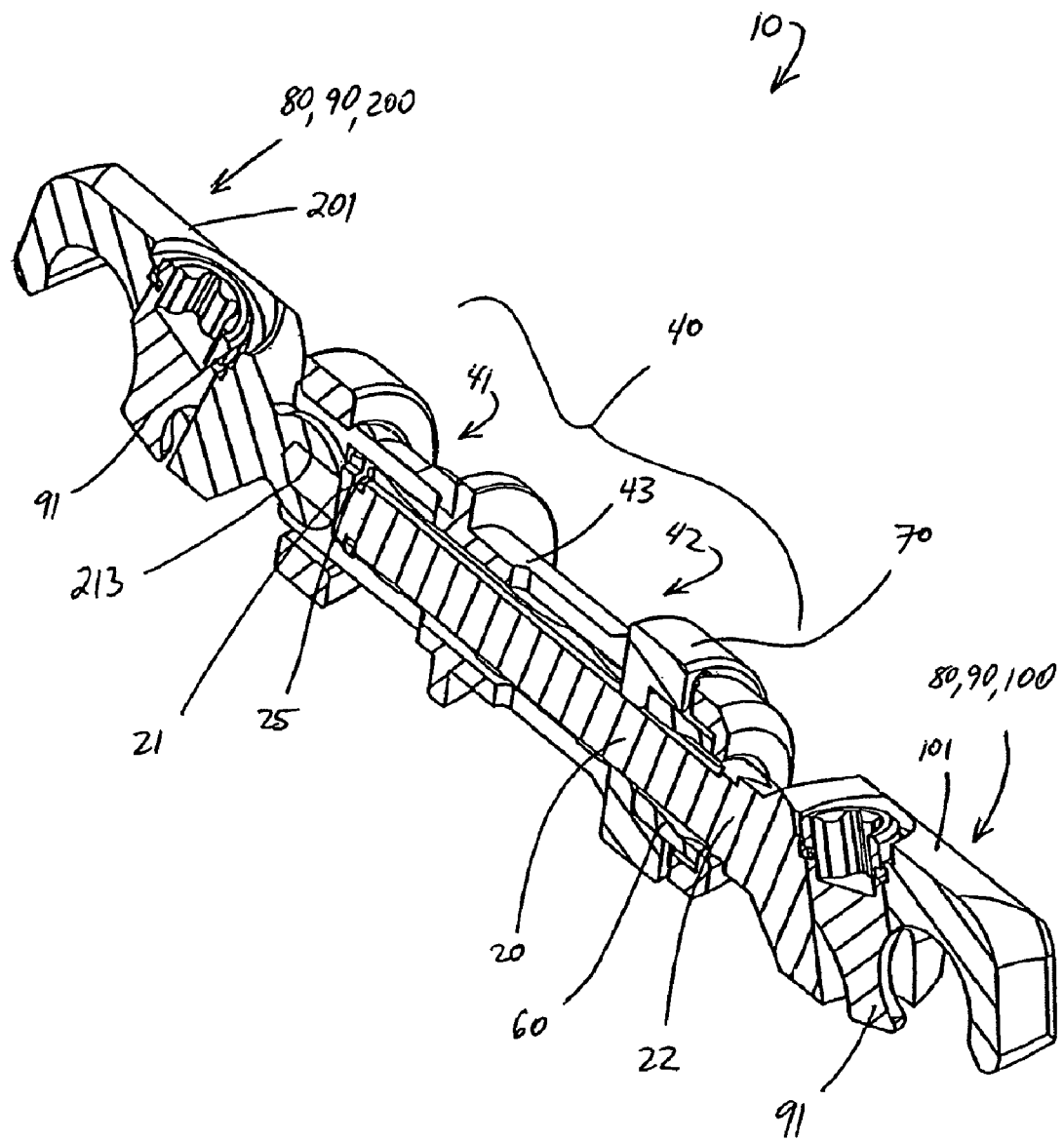
FIG. 6 is a section view in perspective of the connector according to an embodiment of the invention having a fixed jaw and an articulating jaw.
Figure 15:
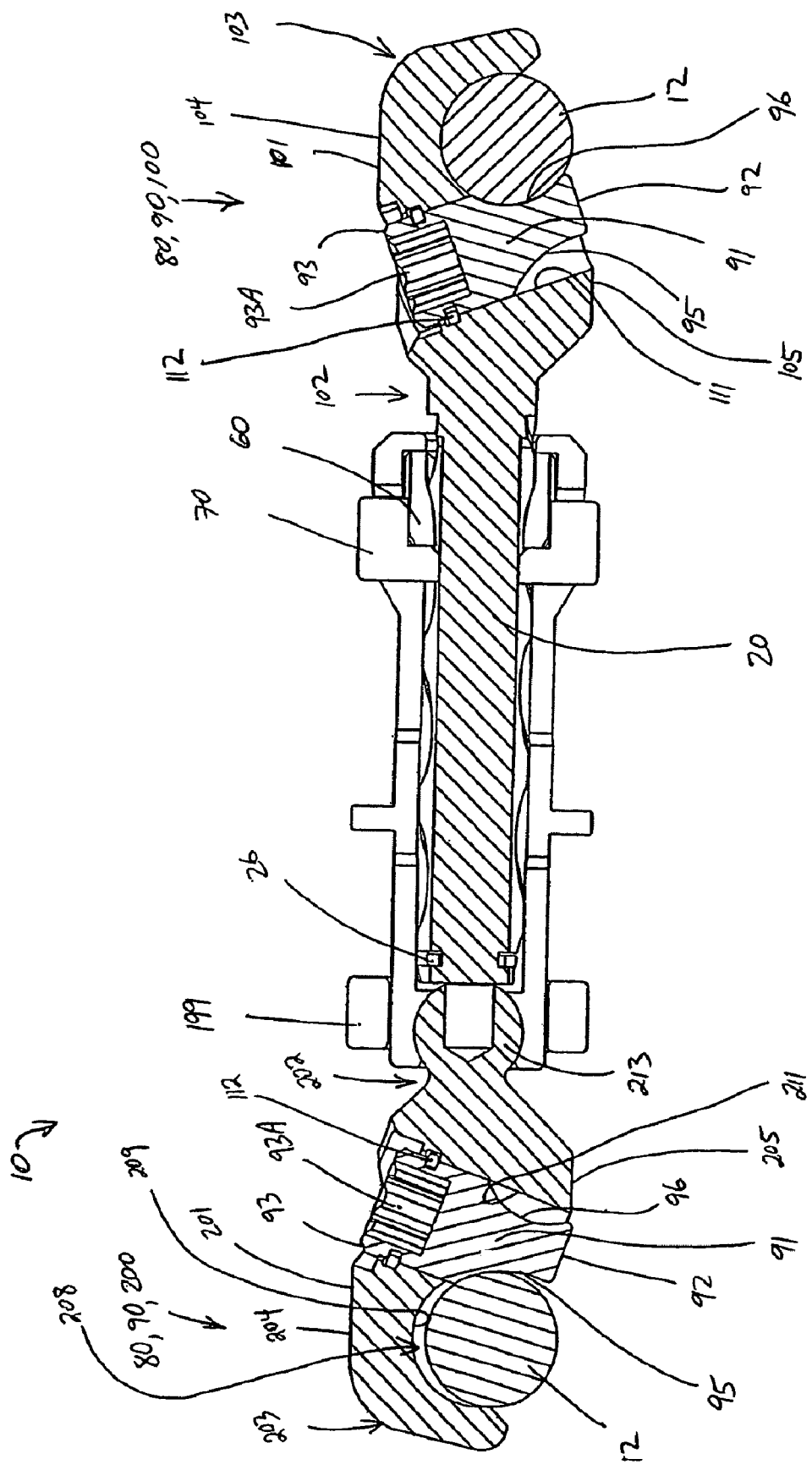
FIG. 15 is a sectional elevation view of a connector according to the invention having a fixed jaw (shown with a rod in the jaw and the cam in a locked position) and an articulating jaw (shown with the rod in the jaw and the cam in an unlocked position).
Figure 19:
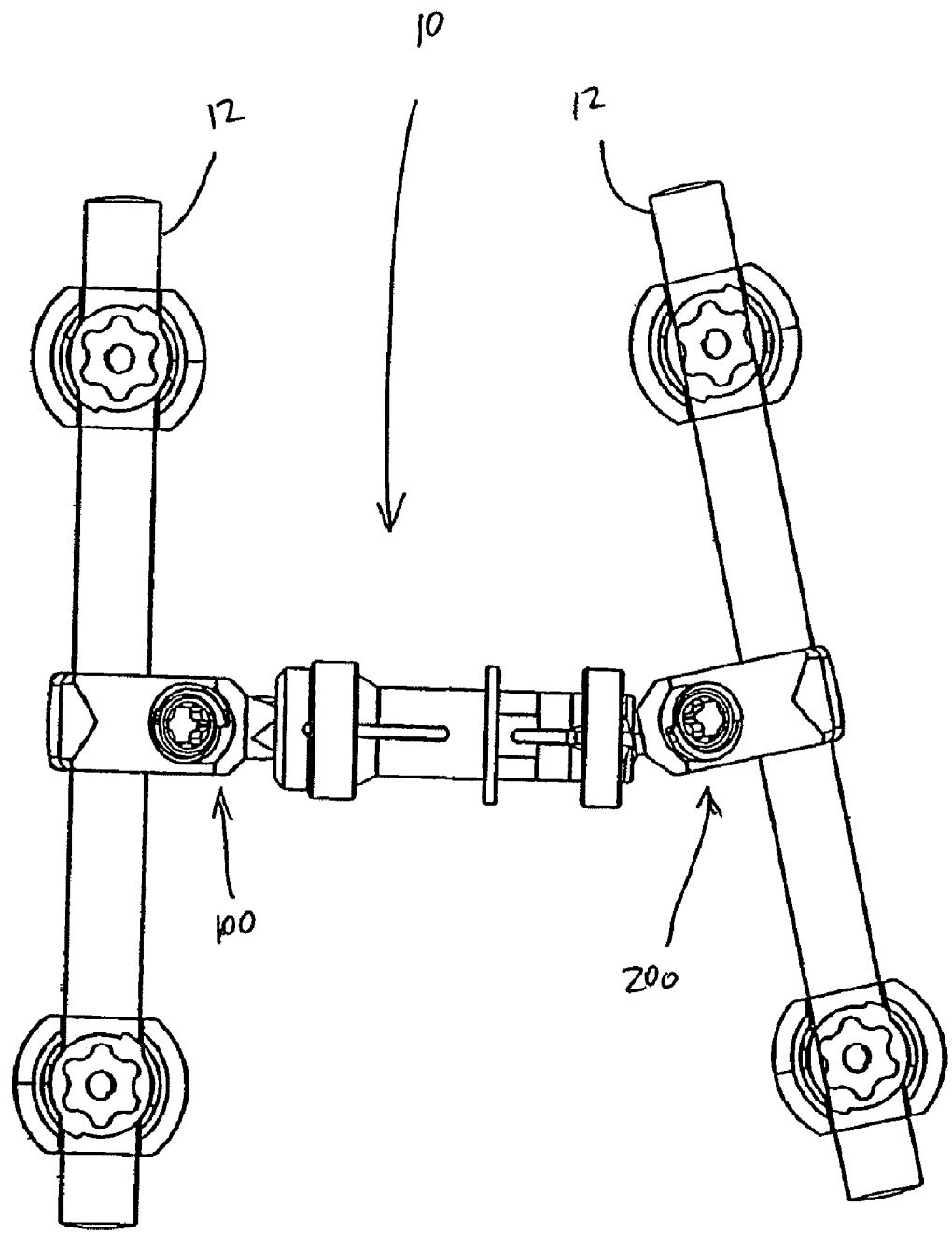
FIG. 19 is a top plan view of the connector shown in FIG. 2.
Figure 20:
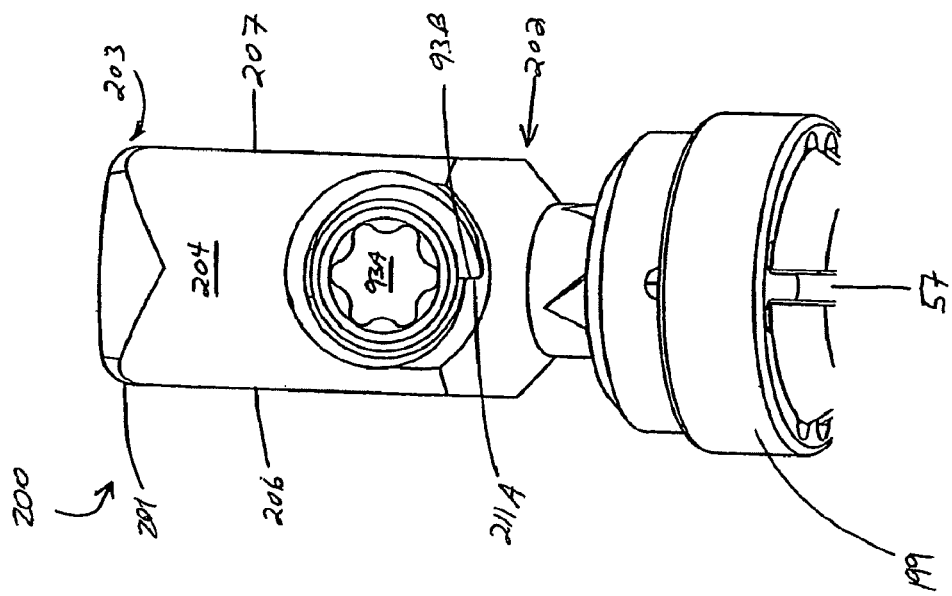
FIG. 20 is a partial top plan view of an articulating jaw of a connector according to one embodiment of the invention showing the locking cam in a locked position and the articulating jaw in an unlocked position.
Figure 21:
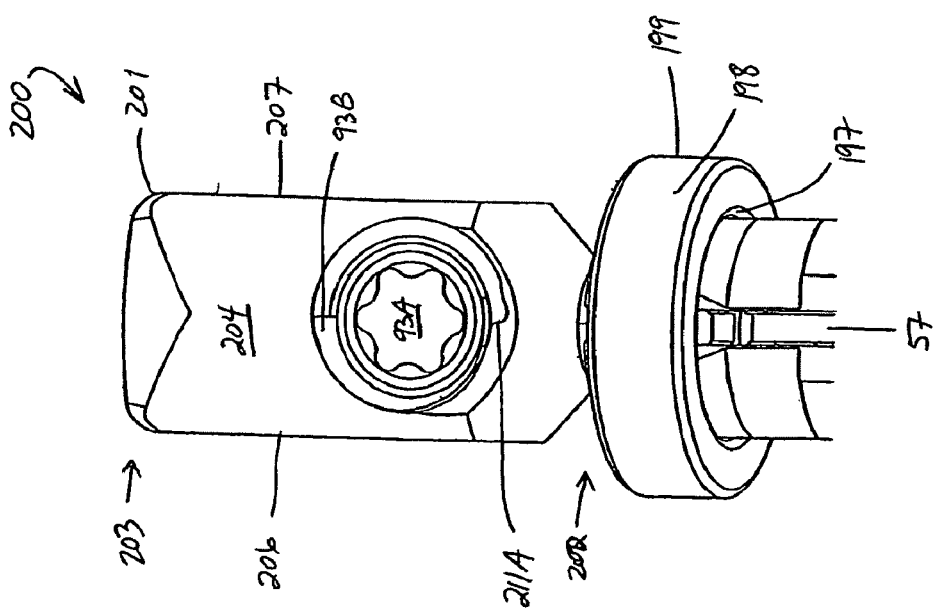
FIG. 21 is partial top plan view of the articulating jaw shown in FIG. 20 showing the locking cam in an unlocked position and the articulating jaw in a locked position.
Figure 31:
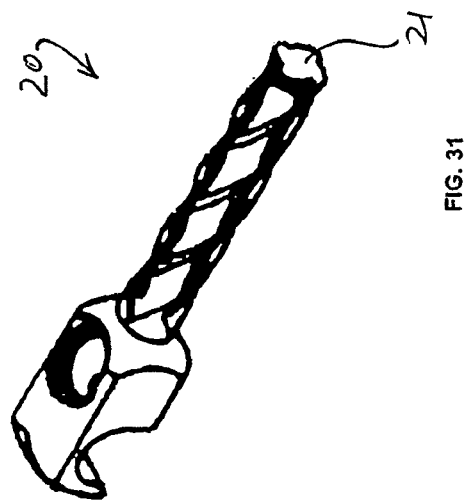
FIG. 31 is a perspective view of an extending shaft according to an embodiment of the invention shown with a fixed jaw fitting.
Figure 34:
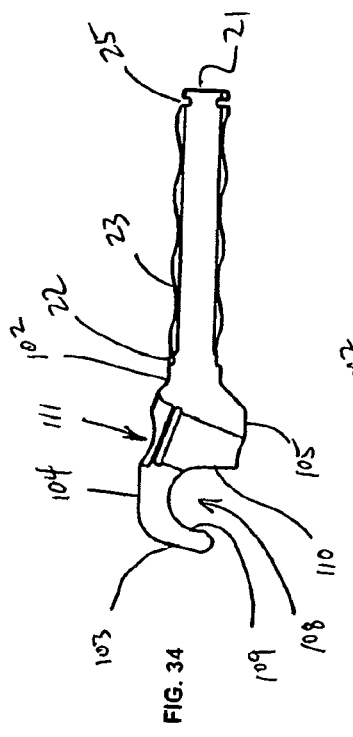
FIG. 34 is a side elevation cutaway view of the extending shaft shown in FIG. 32.
Figure 33:
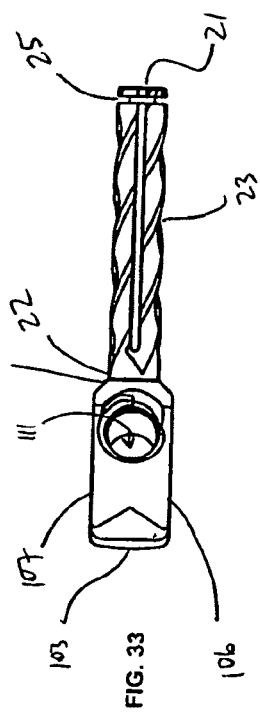
FIG. 33 is a top view of the extending shaft of FIG. 31.
Figure 32:
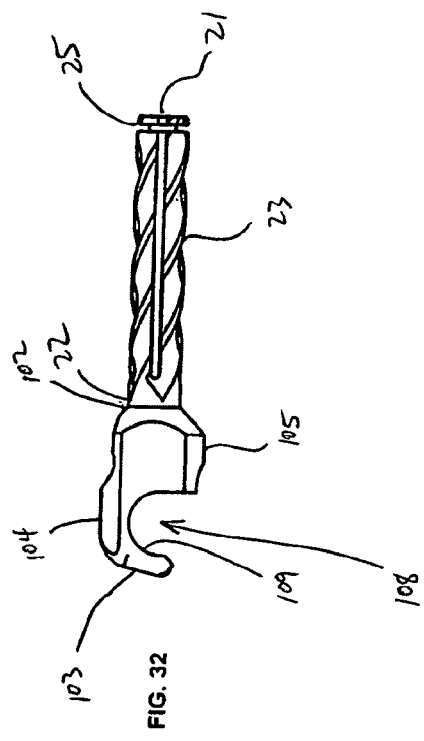
FIG. 32 is a side elevation view of the extending shaft of FIG. 31.
Figure 35:
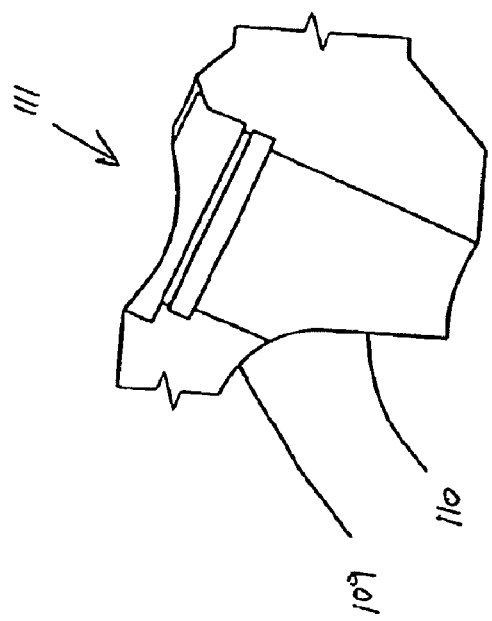
FIG. 35 is an enlarged cutaway view of the radial opening and the axial opening of the body of a fixed jaw shown in FIG. 34.
Figure 36:
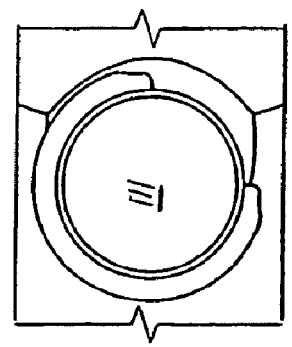
FIG. 36 is a top view of the radial opening shown in FIG. 35.
Figure 38:
FIG. 38 is a side elevation view of the articulating jaw shown in FIG. 37.
Figure 39:
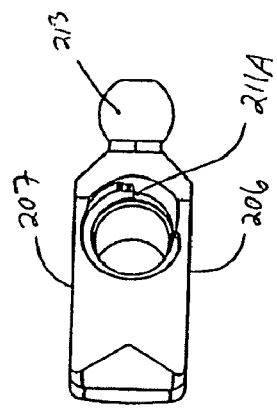
FIG. 39 is a top view of the articulating jaw shown in FIG. 37.
Figure 40:
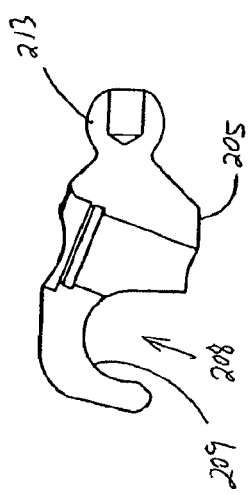
FIG. 40 is a side elevation cutaway view of the articulating jaw shown in FIG. 38.
Figure 41:
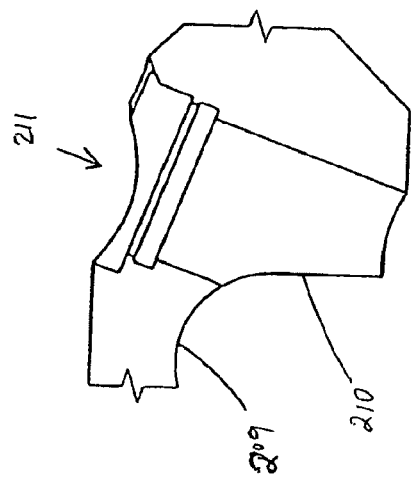
FIG. 41 is an enlarged cutaway view of the radial opening and the axial opening of the body of the articulating jaw shown in FIG. 40.
Figure 42:
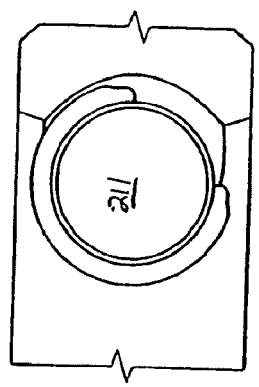
FIG. 42 is a top view of the radial opening shown in FIG. 41.
Figure 37:
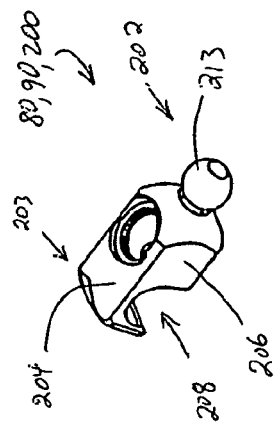
FIG. 37 is a perspective view of an articulating jaw according to an embodiment of the invention.

FIGS. 1, 2, and 19 show connectors 10 according to an embodiment of the invention in use as connectors to secure and connect two spinal rods 12. The connectors 10 can have fixed jaws 100, articulating jaws 200, or a combination of fixed and articulating jaws. The connectors 10 can thus accommodate rods 12 in any orientation and spatial arrangement.

FIGS. 3-6 show additional views of a connector 10 according to an embodiment of the invention. The connector 10 generally comprises a two-piece body having an extending shaft 20 and a housing 40; a rotor 60; and a locking collar 70. Each end of the connector 10 has a fitting 80 for engaging a structure (e.g., a rod 12, a vertebral body, and the like). In embodiments wherein the connector 10 is used to connect rods 12, the preferable fittings 80 comprise jaws 90 for engaging the rod 12. The jaws 90 can be in the form of a fixed jaw 100 or an articulating jaw 200, depending on the needs of the surgeon. Each fitting 80 includes a proximal end 81 and a distal end 82. The proximal end 81 preferably engages the connector 10 while the distal end 82 preferably engages other structures (for example, rods 12 in some embodiments or vertebral bodies in other embodiments, to name just a couple).

FIGS. 7-10 show a housing 40 of an adjustable embodiment for use with an articulating jaw 200. The housing 40 has a first portion 41 and a second portion 42 and preferably comprises two parts: a body 43 and a rotor 60. The first portion 41 preferably is attachable to an articulating jaw 200 (described below). The second portion 42 receives the extending shaft 20 (described below). The housing 40 is generally cylindrical with a first axial opening 44 therein for receiving the articulating jaw 200 and a second axial opening 45 therein for receiving the extending shaft 20. The rotor 60 is located in the second axial opening 45. The rotor 60 is generally cylindrical having an outer surface 61 and an inner surface 62. The inner surface 62 preferably contains one or more helical grooves 63 thereon so as to mate with corresponding helical grooves of the extending shaft 20. The outer surface 61 preferably contains circumferential grooves 64.

The second portion 42 preferably has a generally stepped cylindrical shape with a proximal end 46 having a first outer surface 48 and a distal end 47 having a second outer surface 49, wherein the second outer surface 49 has a diameter greater than that of the first outer surface 48. One or more slots 50 are formed in the first and second outer surfaces 48, 49. A ramping surface 51 provides a transition between the first outer surface 48 and the second outer surface 49. A lip 52 preferably is provided at the distal end of the ramping surface 51.

Figure 43:
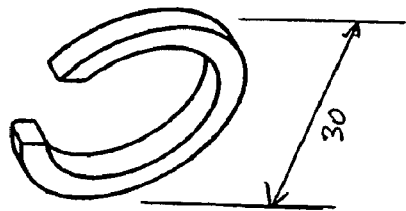
FIG. 43 is a perspective view of a retaining ring according to an embodiment of the invention.
Figure 44:
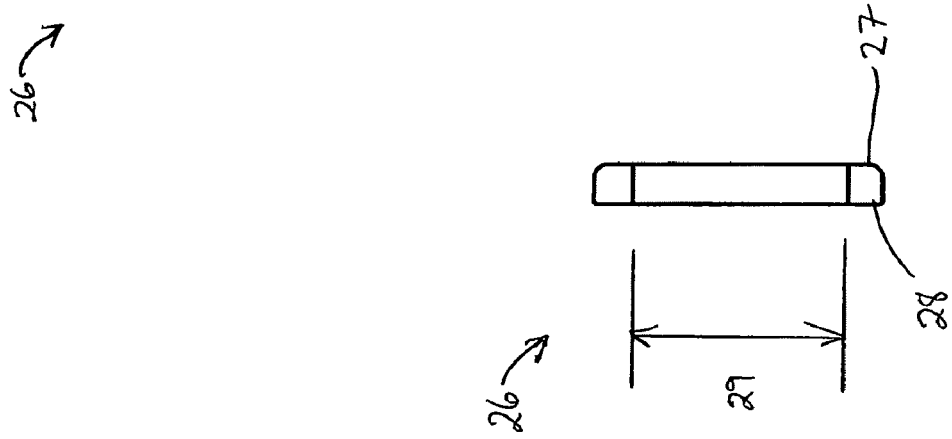
FIG. 44 is an end elevation view of the retaining ring shown in FIG. 43.

Referring to FIGS. 31-36, a typical extending shaft 20 is depicted. These Figures show a fixed jaw 100 attached as the fitting 80, but recall that many types of fittings 80 are possible, including articulating jaws 200 (when used to connect rods 12) or other forms of endplates and so forth (when used as a corpectomy device). The extending shaft 20 has a first end 21 and a second end 22 wherein the first end 21 is insertable into the second axial opening 45 of the second portion 42 and wherein the second end 22 is typically fitted with fitting 80. The extending shaft 20 has one or more helical grooves 23 disposed about its outer surface 24. A groove 25 is preferably located near the first end 21. This groove 25 will receive a retaining ring 26 (see FIGS. 43-44) which has a leading surface 27 and a trailing surface 28 and an inner diameter 29 and an outer diameter 30. As with many retaining rings, retaining ring 26 is resiliently expandable (such that inner diameter 29 and outer diameter 30 increase) so as to be fitted over the extending shaft 20 and moved to its residence in the groove 25, whereupon it contracts to its equilibrium dimensions. Similarly, the retaining ring 26 is resiliently contractible (such that inner diameter 29 and outer diameter 30 decrease) so as to be forcibly inserted into the second axial opening 45 past a structure that has an opening smaller than the outer diameter 30 (which could be a structure within the second portion 42 or which could be the inner surface 72 of the locking collar 70 (described below), as but two examples).

Figure 16:
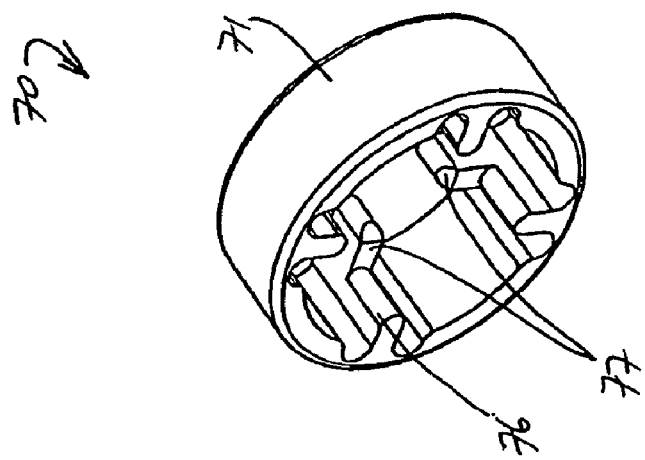
FIG. 16 is a perspective view of a locking collar according to an embodiment of the invention.
Figure 18:
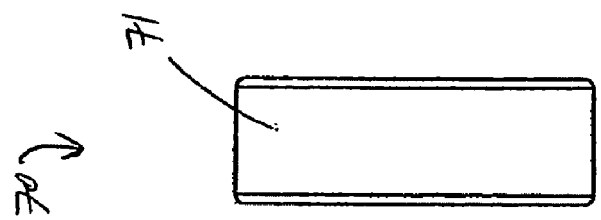
FIG. 18 is a side elevation view of the locking collar shown in FIG. 16.
Figure 17:
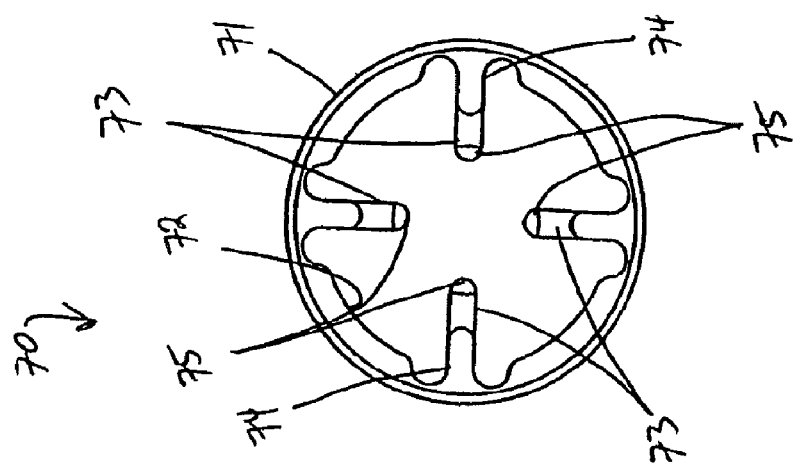
FIG. 17 is an end view of the locking collar shown in FIG. 16.

Referring to FIGS. 16-18, surrounding the body 43 is preferably a locking collar 70. The locking collar 70 is generally cylindrical in shape and comprises an outer surface 71 and an inner surface 72 and a proximal end 74 and a distal end 75. One or more protrusions 73 extend inwardly from the inner surface 72. The protrusions 73 are preferably stepped such that they have a first height 76 at the proximal end 74 and a second height 77 at the distal end 75, wherein the second height 77 is greater than the first height 76. The protrusions 73 reside in the slots 50, thus locating the locking collar 70 on the second portion 42 of the body 43. The locking collar 70 is slideable between a first unlocked position and a second locked position. In the first unlocked position, the locking collar 70 is located toward the proximal end 46 on the first outer surface 48 and the protrusions 73 do not engage the circumferential grooves 64 of the rotor 60. As the locking collar 70 is slid toward the distal end 47, the inner surface 72 of the locking collar 70 begins contacting the ramping surface 51. In the lock position the locking collar 70 passes over lip 52 and the inner surface 72 contacts the second outer surface 49. In this position, the second height 77 of the protrusions 73 engages one or more circumferential grooves 64 on the outer surface 61 of the rotor 60. In this position, the protrusions 73 prevent the rotor 60 from rotating about its axis.

With continuing reference to FIGS. 31-36, the fitting 80 is shown in this embodiment as a fixed jaw 100. The fixed jaw 100 shown here comprises a body 101 having a proximal end 102 and a distal end 103; an upper surface 104 and a lower surface 105; and a first side surface 106 and a second side surface 107. In the embodiment shown for connecting rods 12, a rod opening 108 extends through the first and second side surfaces 106, 107 and is preferably open at the lower surface 105. The rod opening 108 forms an inner surface 109 that forms a partial cylindrical shape. The inner surface 109 has an axial opening 110 near the proximal end 102 for communication with a locking cam 90 (described below). The locking cam 90 is insertable in a radial opening 111 preferably located in the upper surface 104. The locking cam 90 is preferably retained in the radial opening 111 by a retaining ring 112 with structure and function similar to that of retaining ring 26.

Referring now to FIGS. 7-10 and 15, the first portion 41 is shown as attachable to a fitting 80 that takes the form of an articulating jaw 200. The first portion 41 preferably has a generally stepped open cylindrical shape with a proximal end 53 having a first outer surface 55 and a distal end 54 having a second outer surface 56, wherein the second outer surface 56 has a diameter greater than that of the first outer surface 55. Grooves 57 are formed in the distal end 54 at the first axial opening 44 so as to create resilient fingers 58. The resilient fingers 58 have an entrance diameter 58A and an internal opening 58B having a diameter 58C located a distance within the first portion 41, wherein the diameter 58C is greater than the entrance diameter 58A. A ramping surface 59 provides a transition between the first outer surface 55 and the second outer surface 56. A collar 199 having a generally open cylindrical shape has an outer surface 198 and an inner surface 197 and is assembled first to reside about the first outer surface 55 in an unlocked position. The collar 199 is slideable distally from the unlocked position to a locked position wherein the inner surface 197 surrounds the second outer surface 56. In this position, since the second outer surface 56 has a diameter greater than the first outer surface 55, the inner surface 197 of the locking collar 199, as it moves along ramping surface 59 and into the locking position, forces resilient fingers 58 to deflect inwardly. When a ball 213 (described below) is present within the internal opening 58B, this deflection locks the fingers 58 onto the outer surface of the ball 213, thus maintaining the articulating jaw 200 in a desired orientation.

Referring to FIGS. 37-42, a particular articulating jaw 200 is shown. The articulating jaw 200 has many of the same structures as that of the fixed jaw 100, and so the similar features will not be further described. These similar features include a body 201 having a proximal end 202 and a distal end 203; an upper surface 204 and a lower surface 205; a first side surface 206 and a second side surface 207; a rod opening 208; inner surface 209; axial opening 210; radial opening 211; and retaining ring 212. Additionally, however, the articulating jaw 200 further comprises a ball 213 located at the proximal end 202. The ball 213 can take several shapes, including spherical and ovoidal, but is preferably spherical. The ball 213 has a diameter 214 that is preferably larger than the entrance diameter 58A and less than or equal to the diameter 58C.

Referring now to FIGS. 3, 4, 6, and 22-26, each jaw 90, whether fixed or articulating, preferably has a locking cam 91 for alternately engaging or disengaging a rod 12 therein. A particularly useful embodiment of a locking cam 91 is shown in FIGS. 22-26, though many other types of connectors or cams can be used. The locking cam 91 generally comprises an engaging end 92 and a driving end 93, wherein the engaging end 92 is fitted with a complex curvate surface 94 having at least a first curvate surface 95 and a second curvate surface 96 such that in an unlocked position, the rod 12 can slide freely within the jaw 90, and in a locked position, the rod 12 is securely locked to the jaw 90 of the connector 10. The locking cam 91 can have a retaining mechanism 97 to keep the locking cam 91 in the jaw 90, such as a retaining ring that snaps into an undercut 98 in the jaw 90. Many embodiments of the engaging end of the locking cam 91 are possible to accomplish this. The embodiment shown in FIG. 15 utilizes a complex curvature such that in section view—in an unlocked position (see the left jaw 90)—the first curvate surface 95 is located adjacent the rod 12, and the second curvate surface 96 is located away from the rod 12. The first curvate surface 95 may have a radius of curvature that is greater than that of the second curvate surface 96. Alternatively, the first curvate surface 95 may have the same radius of curvature as that of the second curvate surface 96 but may offset the origin of the curvature farther away from the centerline of the locking cam 91. Upon rotation of the locking cam 91 from the unlocked to the locked position (see the right jaw 91 shown in FIG. 15), gradually the second curvate surface 96 is brought into contact with the rod 12, which wedges the rod 12 against the inner surface 109 within the jaw 90, thereby locking the rod 12 in position. This ability to draw the rod 12 up to the jaw 90 compensates for any misalignment between the opposing rods 12.

FIGS. 20-26 and 37-42 show one example of the visual and tactile feedback provided by the locking cams 91 of the invention on use with an articulating jaw 200. As stated above, the locking cam 91 generally comprises an engaging end 92 and a driving end 93. The driving end 93 is preferably circular in cross section and has a cavity 93A to receive a driving instrument (not shown) and an appurtenant stop 93B disposed at a location along its perimeter. The locking cam 91 is inserted into the radial opening 211 and is secured therein by a retaining mechanism 97. The radial opening 211 preferably comprises a substantially circular opening having a discontinuity 211A disposed out of phase with the appurtenant stop 93B when in the unlocked position. A driving instrument turns the locking cam 91 the desired amount (preferably approximately 180 degrees). This turning rotates the engaging end 92 about the locking cam's 91 axis of rotation, which brings the second curvate surface 96 into contact with the rod 12, which wedges the rod 12 against the inner surface 209. When fully turned, the appurtenant stop 93B engages the discontinuity 211A, which visually and tactily informs the surgeon that the cam is locked.

FIGS. 27-30 show an alternative embodiment of a connector 10 of fixed length. Various sizes of such connectors 10 can be manufactured according to common lengths needed for patients of varying sizes and varying portions of the spine. In this embodiment, although no length adjusting mechanism as described above is present, the novel locking cam 91 structure to secure the rods 12 is present.

FIGS. 45 and 46 show an alternative embodiment of a connector 10 wherein the extending shaft 20 and the housing 40 are pre-bent to account for spinal curvature. Such embodiment can better reduce or eliminate interference of the connector 10 with vertebrae or other structures.

Figure 47:
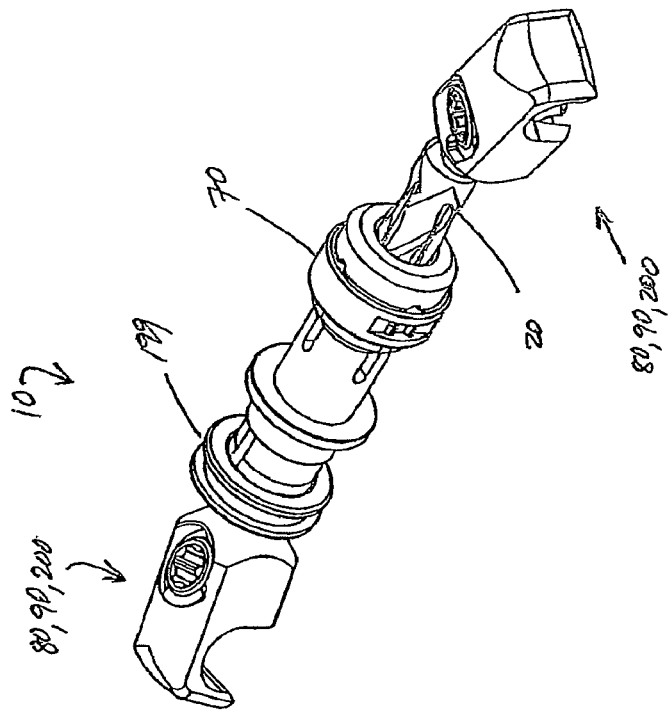
FIG. 47 is a perspective view of a connector according to an alternative embodiment wherein the connector incorporates two articulating jaws.
Figure 49:
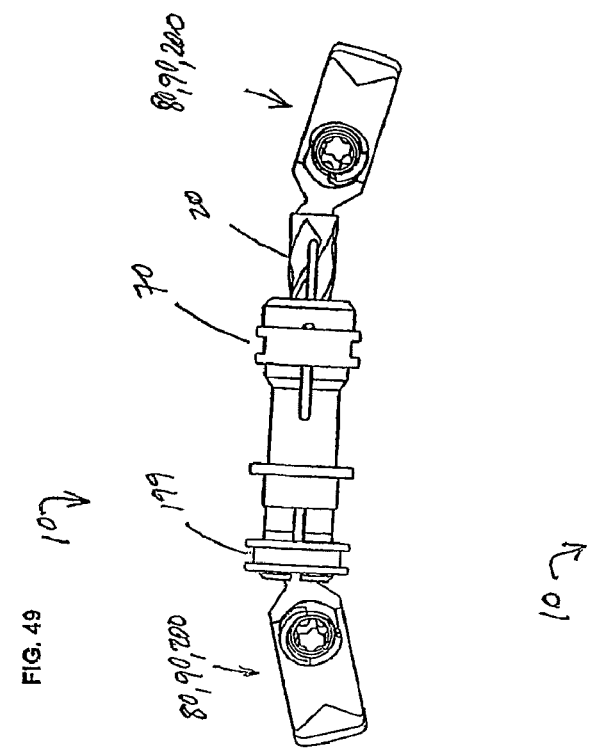
FIG. 49 is a top view of the connector shown in FIG. 47.
Figure 48:
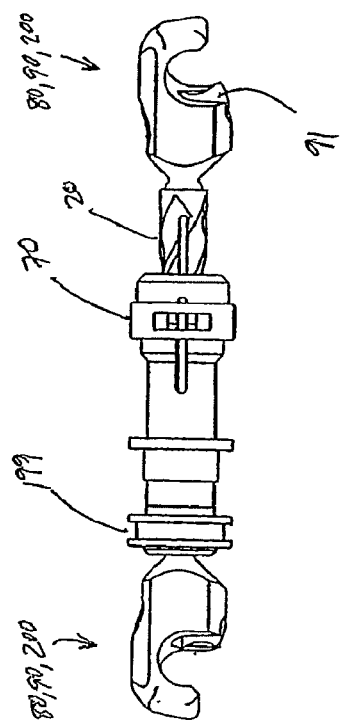
FIG. 48 is a front elevation view of the connector shown in FIG. 47.
Figure 50:
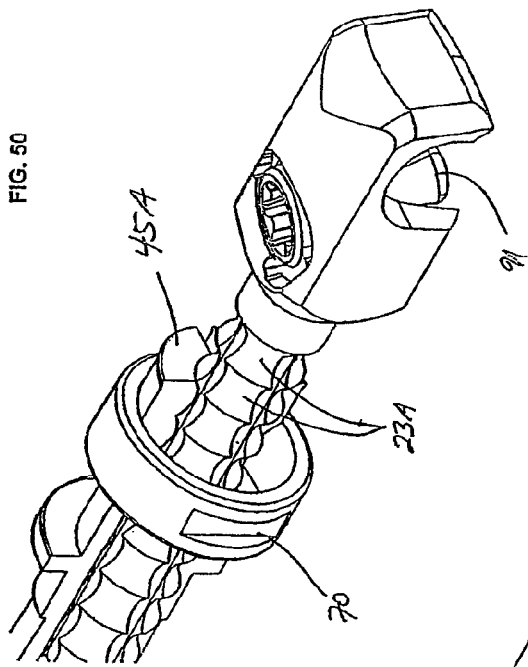
FIG. 50 is a partial perspective view of an alternative embodiment of the invention wherein the extending shaft has circumferential grooves, shown in an unlocked position.
Figure 52:
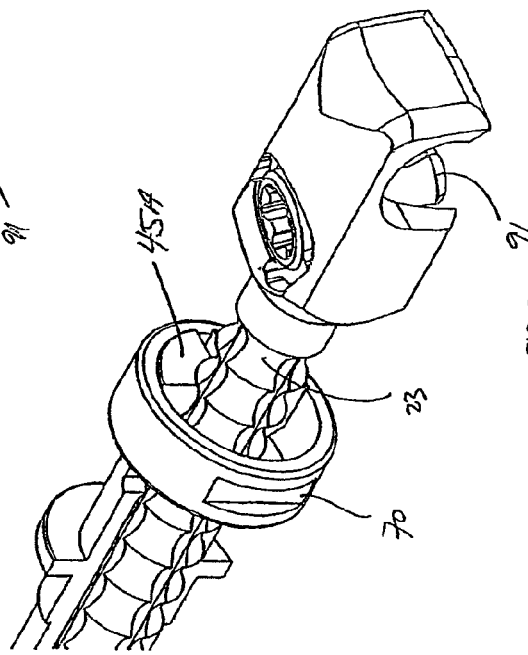
FIG. 52 is a partial perspective view of the connector shown in FIG. 50, shown in a locked position.
Figure 51:
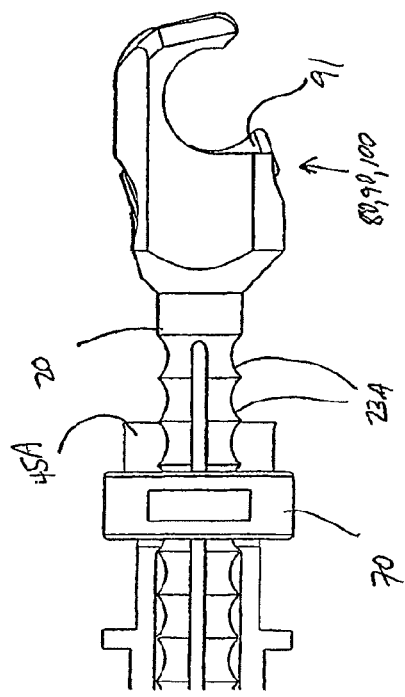
FIG. 51 is a side elevation view of the connector shown in FIG. 50.
Figure 53:
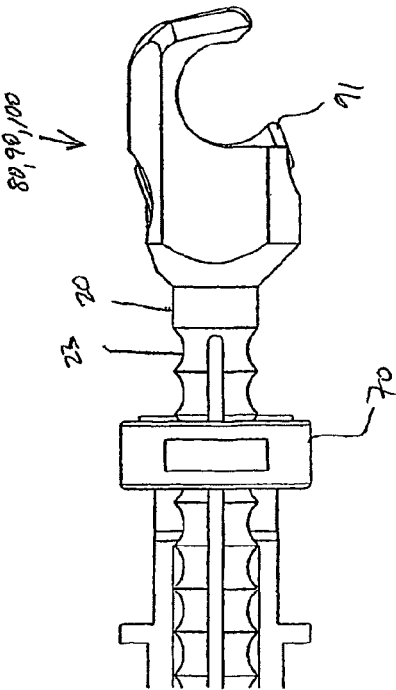
FIG. 53 is a side elevation view of the connector shown in FIG. 52.
Figure 54:
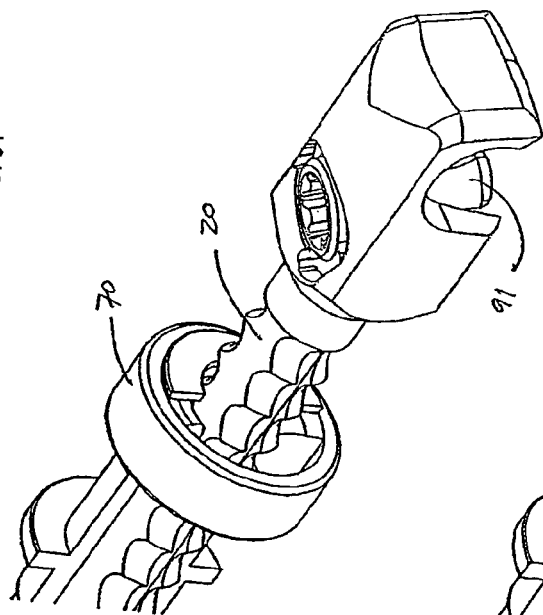
FIG. 54 is a partial perspective view of an alternative embodiment of the invention wherein the extending shaft has circumferential grooves but the shaft directly interfaces the locking collar, shown in an unlocked position.
Figure 56:
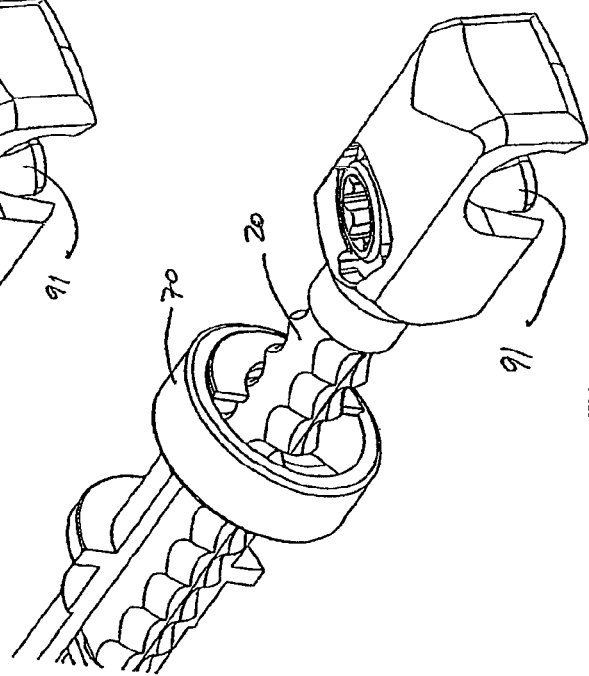
FIG. 56 is a perspective view of the connector shown in FIG. 54, shown in a locked position.
Figure 55:
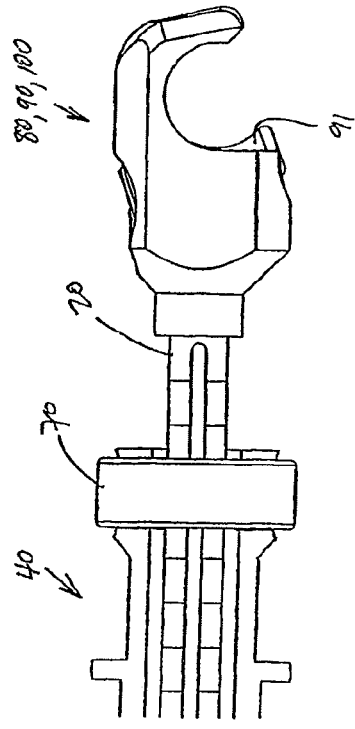
FIG. 55 is a side elevation view of the connector shown in FIG. 54.
Figure 57:
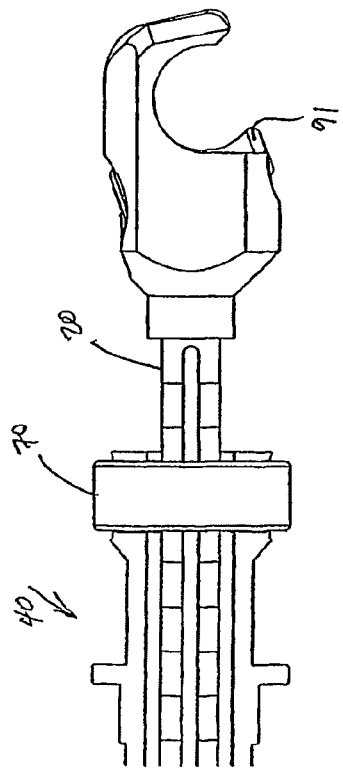
FIG. 57 is a side elevation view of the connector shown in FIG. 56.

FIGS. 47-49 show an alternative embodiment of a connector 10 wherein the connector 10 contains two articulating jaws 200. Such embodiment is useful where the rods 12 are highly divergent. Without multiple articulating jaws 200, bending may be required for some connectors 10. This embodiment employs an articulating jaw 200 on both ends of the connector 10 to eliminate the need for any bending. It also enables better placement of the connector in vivo to avoid any interference from surrounding structures. The articulating jaw in the extending shaft 20 is similar in structure and function to that of the already described articulating jaw 200, providing means for rotating the jaw; locking it to the extending shaft 20; and telescoping the extending shaft 20 out of the housing 40.

FIGS. 50-53 show an alternative embodiment of a connector 10 wherein the extending shaft 20 comprises circumferential grooves 23A along the length thereof. The housing 40 has a corresponding ring 45A with grooves, for example within second axial opening 45 that will mate with the groves 23A on the extending shaft 20. The extending shaft 20 moves relative to the housing 40, thus varying the overall length of the connector 20. The ring 45A is deflectable such that once the extending shaft 20 is in the proper place the housing 40 can be locked down onto the extending shaft 20 via a locking collar 70. The locking collar 70 is located preferably around the end of the housing 40 and locks the housing 40 on the extending shaft 20 by means of a cam feature or similar devices.

FIGS. 54-57 show an alternative embodiment to the circumferential groove device. In this embodiment, the locking collar 70 directly interfaces the extending shaft 20. The locking collar 70 has circumferential grooves 23A on its inner diameter or portions thereof. The locking collar 70 has an internal diameter that provides clearance to enable the extending shaft 20 to move axially relative to the housing 40. Conversely the extending shaft 20 has a portion thereof devoid of grooves to allow it to move freely relative to the locking collar 70. The locking collar 70 will be secured in place axially relative to the housing 40, but will be free to rotate a certain degree in order to interface with the extending shaft 20. When the desired length is reached the locking collar 70 can be turned a predetermined angle to engage the extending shaft 20. Other means of preventing the extending shaft 20 from rotating within the housing 40 are possible, including, but not limited to keys, pins, noncircular shaped second axial opening 45, and the like.

Figure 58:
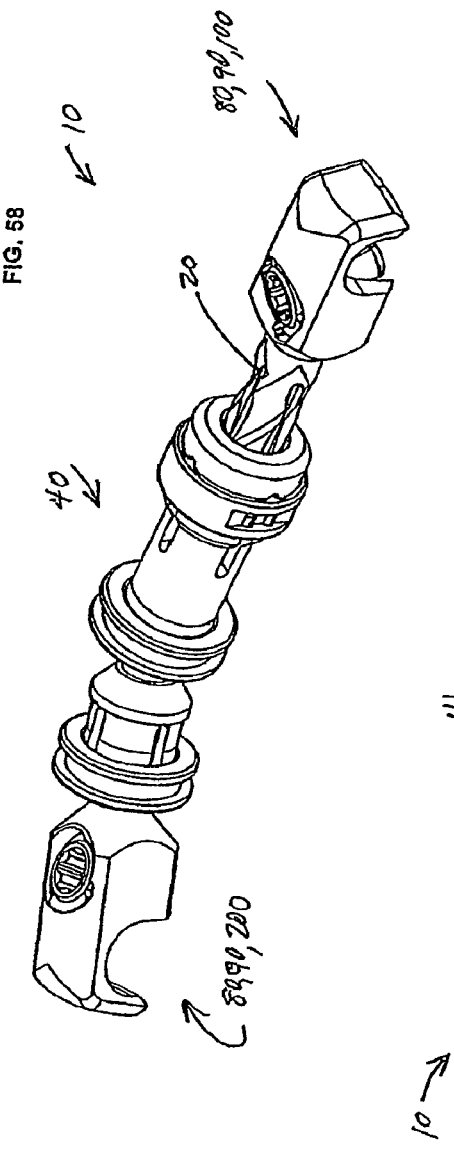
FIG. 58 is a perspective view of an alternative embodiment of the invention utilizing a portion of the housing to articulate.
Figure 60:
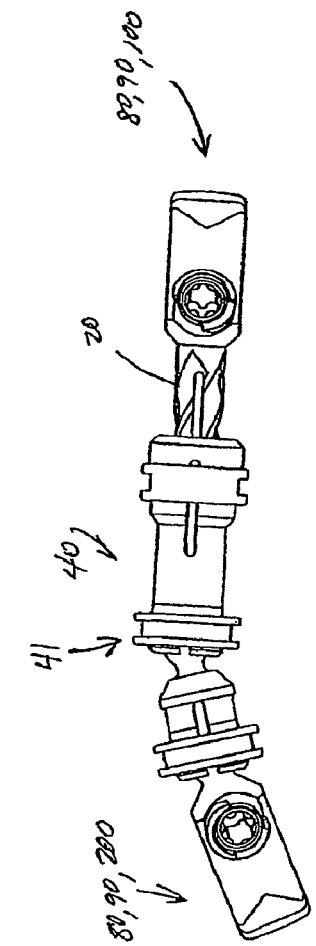
FIG. 60 is a top view of the connector shown in FIG. 58.
Figure 59:
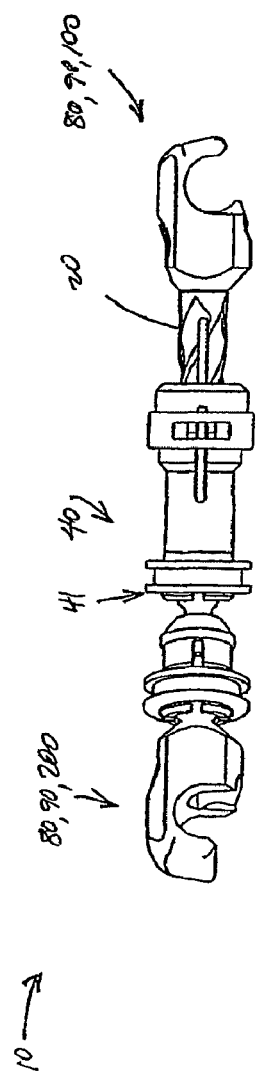
FIG. 59 is a side elevation view of the connector shown in FIG. 58.

FIGS. 58-60 show an alternative embodiment of a connector 10 wherein instead of providing an articulating jaw 200, an articulating housing 40 is provided. Basically instead of employing the first axial opening 44 to receive the ball 213 of the articulating jaw 200, the first portion 41 of the housing 40 receives a ball. A locking mechanism can be incorporated into the connector 10 to permit the housing 40 to be fixed at a desired angle. The housing 40 preferably can pivot in all planes. Articulating jaws 200 as described above can be incorporated into this embodiment to allow for even more capability to interface with diverging rods.

Figure 61:
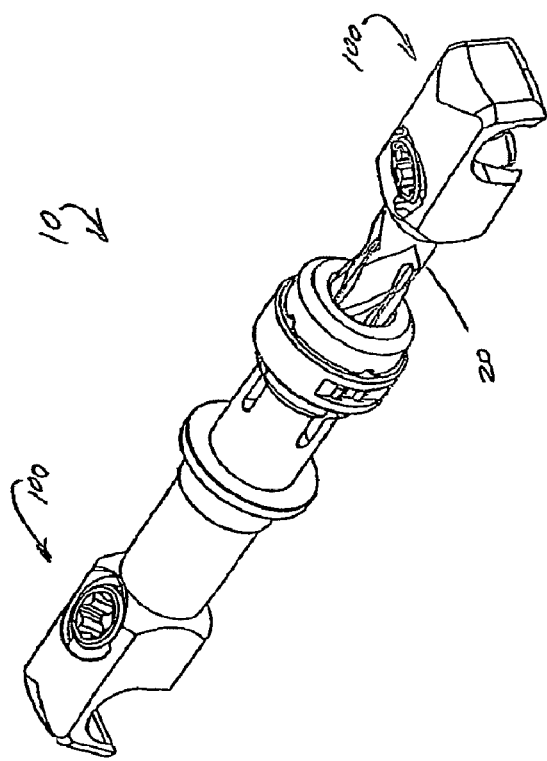
FIG. 61 is a perspective view of an alternative embodiment of the invention having two fixed jaws.
Figure 63:
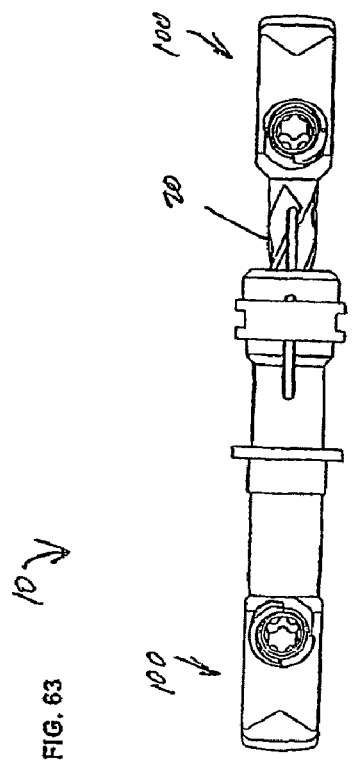
FIG. 63 is a top view of the connector shown in FIG. 61.
Figure 62:
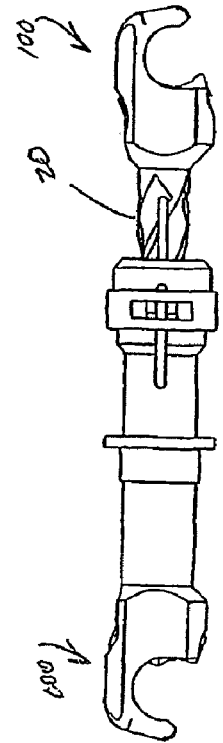
FIG. 62 is a side elevation view of the connector shown in FIG. 61.

FIGS. 61-63 show another alternative embodiment of a connector 10 wherein two fixed jaws 100 are in use. Any adjustments made to the connector to account for diverging rods 12 would have to be made by bending the connector 10 either at the extending shaft 20 or on the housing 40 itself. Bending could be made in any direction and would only be limited by the physical properties of the material.

FIGS. 64-67 show an alternative embodiment of a connector 10 having a ratcheting telescoping shaft 20. The shaft 20 contains helical grooves 23 similar to that previously described. The shaft 20 interfaces a rotor 60 that similarly has internal helical grooves 63 matching the external profile of the shaft 20. The rotor 60 likewise comprises circumferential grooves 64 or other indentations or extrusions on its external surface, again like that described above. A split ring 70A is provided that engages the circumferential grooves 64. The split ring 70A has engaging features on its internal surface which spring open when the circumferential grooves 64 rotate past them. This provides a ratcheting feel to the telescoping of the shaft 20. The advantage is that a shaft 20 can be placed at a predetermined length before implantation and then small adjustments and locking could be made in vivo. Locking is be accomplished by placing a ring, collar, or similar device onto the split ring 70A to prevent it from springing open. This in turn would prevent the rotor 60 from turning and the shaft 20 from translating.

Figure 68:
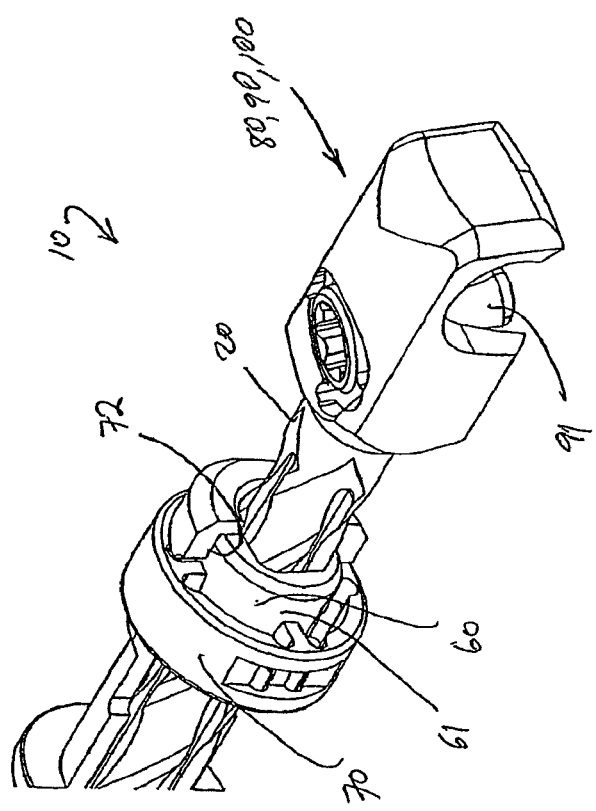
FIG. 68 is a partial perspective view of an alternative embodiment of the invention utilizing a taper lock.
Figure 69:
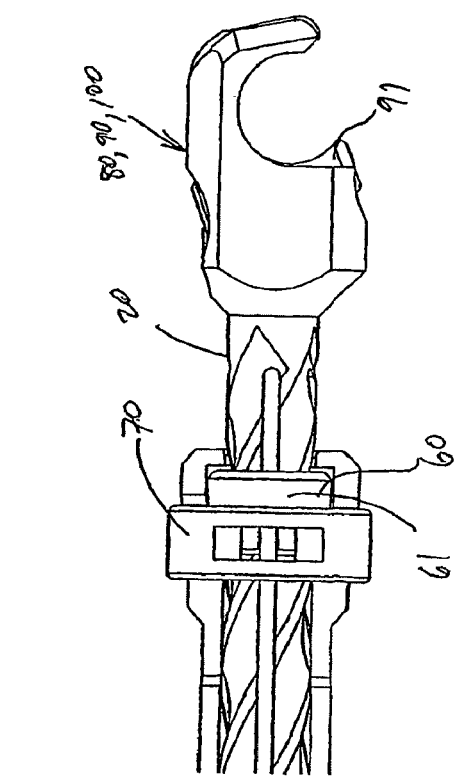
FIG. 69 is a side elevation view of the connector shown in FIG. 68.

FIGS. 68-69 show an alternative embodiment of a connector 10 utilizing a different means to lock the rotor 60. In this embodiment, a taper lock is used in place of the engaging features described above. The rotor 60 is cylindrical in shape but has a taper on the outer surface 61 in the direction of the rotational axis. A locking collar 70 has an inner surface 72 having a taper complementing that of the outer surface 61 of the rotor 60. The locking collar 70 resists rotation relative to the housing 40 thereby. Locking is accomplished by moving the locking collar 70 to interface the rotor 60 via the taper lock, thus preventing the rotor 60 from turning.

FIGS. 70-72 show an alternative embodiment of a connector 10 that is pre-bent in multiple planes. Any combination of bends in planes parallel to the rods 12, perpendicular to the rods 12, or in planes between the two are possible. This would account for any misalignment and divergence of the rods 12. The connector 10 is intended to accommodate rods 12 that are divergent and at different heights. This embodiment is a variation of the embodiment shown in FIGS. 45 and 46.

Referring generally to FIGS. 73-99, an embodiment of an adjustable corpectomy device 300 is provided. The device 300 is intended to be implanted within a spinal column to completely or partially replace a vertebral body 400. The device 300 may also be provided with a supplemental internal fixation system, such as a rod system. The device 300 may also be made to a size and scale so as to be provided as a spinal fusion cage. The device 300 generally comprises a two-piece body having a first cage 320 and a second cage 340; a rotor 360; a locking collar 370 and a bias member 380. The device 300 is configures such that the first cage 320 is adapted to extend into and out of the second cage to extend or contract the overall length of the device 300. The device 300 has a first end 301 and a second end 302. The device 300 is provided with a first endplate 390 at the first end 301, and a second endplate 392 at the second end 302. The endplates 390, 392 are adapted to engage adjacent vertebral bodies 400. The endplates may be provided with vertebral engagement features 394 to better grip the adjacent vertebral bodies. Such engagement features 394 may be provided as, for example, teeth, ridges, a series of peaks and valleys, a roughened or porous surface, or any other means generally known in the art. The endplates 390, 392 may be provided in a variety of shapes. As but a few examples, the first or second endplates 390, 392 may be round, square or rectangular, or have a modified "D" shape that generally mimics the cross-sectional geometry of a vertebral body 400. In addition, the first or second endplates 390, 392 may be provided with a porous central region 395. The porous central region 395 may allow for bone ingrowth. The endplates 390, 392 may also be provided with three dimensional convex surfaces to mimic and conform to a vertebral endplate.

Referring to FIGS. 73-77, and 81-87, the device 300 is provided with a generally cylindrical second cage 340 having a first portion 341 at a first end 346 and a second portion 342 at a second end 347 and preferably comprises two parts: a body 343 and a rotor 360. The first portion 341 may be provided with, or fixedly or selectively attachable to, a first endplate 390 for engaging an adjacent vertebral body. The first endplate 390 may also be rotatable or articulable about one or more axes. The endplate 390 may be articulable such as to tilt with respect to a longitudinal axis of the device. The first portion 341 may be provided with a first circumference or diameter and the second portion 342 may be provided with a second circumference or diameter. As illustrated in this embodiment, the first portion 341 has a larger circumference or diameter than the second portion 342.

The second portion 342 is provided with an axial opening 345 for receiving the first cage 320 in an axial relationship. A rotor 360 (described herein) is located in the axial opening 345. The second portion 342 may be provided with a generally stepped cylindrical shape with a second end having a first outer surface 348 (shown as an edge) and a first end having a second outer surface 349. The first outer surface 348 has a diameter greater than that of the second outer surface 349. One or more slots 350 are formed in the first and second outer surfaces 348, 349. A ramping surface 351 provides a transition between the first outer surface 348 and the second outer surface 349.

A transition surface 352 may be provided between the first and second portions 341, 342 of the second cage 340. The transition surface 352 may be provided as a surface facing the second end 302 of the device 300. The transition surface 352 may be provided as a support for the bias member 380. The bias member 380 may also contact and push against the first surface 375 of the locking collar 370 (described below). Both of the second cage transition surface 352 and the first end of the locking collar may be provided with a groove or grooves, a rib or ribs, a protrusion, or series of protrusions, any combination thereof, or any other means generally known in the art for retaining the bias member 380 in position. In addition, if either the second cage 340 or locking collar 370 is fabricated from a moldable plastic, then the bias member 380 may be molded into that piece.

Referring now to FIGS. 84-87, the rotor 360 is generally cylindrical having an outer surface 361 and an inner surface 362. The inner surface 362 preferably contains one or more helical ribs 363 thereon so as to mate with corresponding mating helical grooves 323 of the first cage 320. The outer surface 361 preferably contains circumferential grooves 364.

Referring to FIGS. 78-80, a typical first cage 320 is depicted. The first cage 320 has one or more helical grooves 323 disposed about its outer surface 324. The first cage 320 has a first end 321 and a second end 322. The first end 321 is insertable into the axial opening 345 of the second cage 340. The second end 322 may be provided with, or fixedly or selectively attachable to, a second endplate 392 for engaging an adjacent vertebral body 400. The second endplate 392 may also be rotatable or articulable about one or more axes. The endplate 392 may be articulable such as to tilt with respect to a longitudinal axis of the device 300. While not shown in FIGS. 78-80, the first cage may be provided with a retaining ring and mating groove as substantially described in relation to FIGS. 31-34, and 43-44.

Referring to FIGS. 73-77, and 88-90, surrounding the second portion 342 of the second cage 340 is preferably a locking collar 370. The locking collar 370 is generally cylindrical in shape and comprises an outer surface 371 and an inner surface 372 and a second end 374 and a first end 375. One or more protrusions 373 extend inwardly from the inner surface 372. The protrusions 373 are preferably stepped such that they have a first height 376 at the second end 374 and a second height 377 at the first end 375, wherein the second height 377 is greater than the first height 376. The protrusions 373 reside in the slots 350, thus locating the locking collar 370 on the second portion 342 of the body 343.

The locking collar 370 is slideable between a first, unlocked position, and a second, locked position. In the first position, the locking collar 370 is located toward the first end 346 on the first outer surface 348 and the protrusions 373 do not engage the circumferential grooves 364 of the rotor 360. As the locking collar 370 is urged toward the second end 347, the inner surface 372 of the locking collar 370 begins contacting the ramping surface 351. In the second position the locking collar 370 passes over and contacts the second outer surface 349 of the second portion 342 of the second cage 340. In this position, the second height 377 of the protrusions 373 engages one or more circumferential grooves 364 on the outer surface 361 of the rotor 360. In this position, the protrusions 373 prevent the rotor 360 from rotating about its axis.

Still referring to FIGS. 73-77, the device 300 is provided with a bias member 380, such as, for example, a spring, a clip, or other means generally known in the art to bias the locking collar 370 in a second position. The bias member 380 may be provided to bias and hold the locking collar 370 in or toward the second position. Keeping the locking collar 370 biased toward the second end of the device 300 keeps it in its second position. To adjust the height of the device 300, a force must be exerted on the locking collar 370 in an axial direction toward the first end and against the bias force to remove the locking collar 370 from its second locking position.

Additionally, one or both of the device's first cage 320 or second cage 340 may contain a bend or curve to mimic the lordosis of spinal column. Alternatively, this lordosis may be achieved simply by offsetting the engaging surface of the first endplate 390, the engaging surface of the second endplate 392, or both, from the longitudinal axis of the device 300. Further, the device 300 may be manufactured in various sizes to accommodate common length ranges, widths, and load capacities as needed for patients of varying sizes and varying portions of the spine.

In use, the vertebral bodies are distracted to a desired distance by means generally known in the art. FIG. 76 depicts the device 300 in a second, locked, position, and FIG. 76 shows the device in a first, unlocked, position. In the first position, and with a force applied to the locking collar 370 in an axial direction and the bias member 380 compressed, the device 300 may be expanded to a length that matches the desired distance between the distracted vertebral bodies 400. As the device 300 expands, helical grooves 323 on the first cage 320 engage mating helical shaped ribs 363 in the rotor 360 that changes the linear motion of the first cage 320 into rotational motion in the rotor 360.

In the second, locked, position, the force is removed from the locking collar 370 and the bias member 380 is allowed to expand, thereby urging the locking collar 370 toward the second end. The rotor 360 is provided with a series of circumferential grooves 364 in the outer surface 361 that engage protrusions 373 in the locking collar 370 to stop the rotation of the rotor 360, thereby stopping the first cage 320 from extending into or out of the second cage 340. The bias member 380 holds the locking collar 370 in position to lightly engage the rotor until the device 300 has been distracted to prevent initial distention. When the device 300 is in the proper position and final distraction has been performed the locking collar 370 is then biased into its final second, locked, position.

With respect to FIGS. 91-99, several embodiments of the device 300 are depicted that provide varying degrees of articulation for the endplates.

With respect to FIGS. 91-93, the device 300 is provided with endplates 390, 392 that each angulate about a single axis 501. The first and second cages 320, 340 are each provided with a protrusion 500. Each protrusion 500 is provided with a surface about the axis 501. Each surface 501 is also provided with a first set of teeth 502. This first set of teeth 502 corresponds to a second set of teeth 504 located on the endplates 390, 392. When assembled, the first set of teeth 502 meshes with the second set of teeth 504 thereby providing a locking means to fix the first endplate 390 or second endplate 392 at an angle relative to a longitudinal angle of the device 300. A pin 506 is provided to secure the endplates 390, 392 from moving relative to a protrusion 500 along a longitudinal axis of the device 300.

Referring now to another embodiment shown in FIGS. 94-96, the device 300 is provided with endplates 390, 392 that may angulate and rotate about multiple axes by a ball and socket connection. The first and second cages 320, 340 are each provided with a protrusion 500. Each protrusion 500 is provided with a ball or spherical surface 508. The endplates 390, 392 are provided with a corresponding socket 510 that mates with the ball 508, thereby creating a ball and socket fitting. A set screw 512 is provided through an opening 514 through the endplates. The set screw is threadedly accepted through the opening 514, thereby creating a friction fit between the ball and socket, locking the ball and socket in place.

Referring now the FIGS. 97-99, a further embodiment of device 300 is provided with endplates 390, 392 that may rotate about a single axis that coincides with the longitudinal axis of the device 300. The first and second cages 320, 340 are each provided with a protrusion 500 that is generally cylindrical with respect to the longitudinal axis of the device 300. The endplates 390, 392 are provided with an opening that corresponds with the cylindrical protrusion thereby providing and axis of rotation. The protrusion 500 and endplate may be provided with a snap fit such that the endplate does not move in a longitudinal direction with respect to the device 300. However this snap fit may allow rotational axis about the longitudinal axis of the device.

The embodiments of the device 300 may be provided with bone graft material. The bone graft material may be packed inside the first and/or second cages 320, 340 and may also be packed around the device 300.

While there has been described and illustrated particular embodiments of a novel adjustable implant device, it will be apparent to those skilled in the art that variations and modifications may be possible without deviating from the broad spirit and principle of the present invention, which shall be limited solely by the scope of the claims appended hereto.

The invention claimed is:

1. An adjustable corpectomy implant comprising:
   a first cage having a first end and a second end and having at least one helical profile on an external surface thereof;
   a second cage having a second end with a first axial opening therein and a first end and an inner surface and an outer surface, wherein said first axial opening receives therewithin said first end of said first cage;
   a first endplate attached to said second end of said first cage for engaging a first vertebral body;
   a second endplate attached to said first end of said second cage for engaging a second vertebral body;
   a rotor disposed within said first axial opening having an inner surface and an outer surface, wherein said inner surface has a profile that matingly engages said at least one helical profile on said external surface of said first cage, wherein said rotor spins about a cylindrical axis in response to axial movement imparted to said first cage within said second cage;
   a locking collar engageable with said rotor, wherein said locking collar is moveable from a first, unlocked position wherein said rotor is free to rotate about said cylindrical axis to a second, locked position wherein said rotor is prevented from rotating about said cylindrical axis; and
   a bias member, wherein said bias member is adapted to bias said locking collar in said locking position.

2. The adjustable corpectomy implant of claim 1, wherein said rotor further comprises grooves on said outer surface.

3. The adjustable corpectomy implant of claim 2, wherein said locking collar further comprises at least one protrusion directed radially inwardly for engagement with said grooves of said outer surface of said rotor.

4. The adjustable corpectomy implant of claim 3 wherein said first endplate is fixedly attached to said second end of said first cage.

5. The adjustable corpectomy implant of claim 4 wherein said second endplate is fixedly attached to said first end of said second cage.

6. The adjustable corpectomy implant of claim 4 wherein said second endplate is articulatably attached to said first end of said second cage.

7. The adjustable corpectomy implant of claim 3 wherein said first endplate is articulatably attached to said second end of said first cage.

8. The adjustable corpectomy implant of claim 7 wherein said second endplate is fixedly attached to said first end of said second cage.

9. The adjustable corpectomy implant of claim 7 wherein said second endplate is articulatably attached to said first end of said second cage.

10. The adjustable corpectomy implant of claim 1, wherein said bias member is a spring.

11. A bi-directional adjustable corpectomy implant comprising:
    a first cage having a first end and a second end and having at least one helical profile disposed on an outer surface thereof;
    a second cage having a first end for receiving said first end of said first cage in an axial relationship and also having a second end;
    a first endplate attached to said second end of said first cage for engaging a first vertebral body;
    a second endplate attached to said second end of said second cage for engaging a second vertebral body;
    an annular rotor disposed within said second cage having a cylindrical axis and an outer surface and an inner surface, wherein said inner surface has a profile that intimately engages said at least one helical profile of said first cage;
    a locking collar coupled to said second cage and moveable from a first position wherein said rotor is free to spin about its cylindrical axis, to a second position wherein said rotor is prevented from spinning about its cylindrical axis;
    wherein when said locking collar is in said first position said at least one helical profile on said first cage and said profile of said rotor provide bi-directional adjustability for said implant, said first cage being freely extendable within said second cage in response to an applied tension force on said first and second endplates, and said first cage being freely retractable within said second cage in response to an applied compression force on said first and second endplates; and
    a bias member.

12. The bi-directional adjustable corpectomy implant of claim 11, wherein said outer surface of said annular rotor further comprises grooves.

13. The bi-directional adjustable corpectomy implant of claim 12, wherein said locking collar further comprises at least one protrusion directed radially inwardly for engagement with said outer surface of said rotor.

14. The bi-directional adjustable corpectomy implant of claim 13, wherein said first endplate is fixedly attached to said second end of said first cage.

15. The bi-directional adjustable corpectomy implant of claim 14, wherein said second endplate is fixedly attached to said second end of said second cage.

16. The bi-directional adjustable corpectomy implant of claim 14, wherein said second endplate is articulatably attached to said second end of said second cage.

17. The bi-directional adjustable corpectomy implant of claim 13, wherein said first endplate is articulatably attached to said second end of said first cage.

18. The bi-directional adjustable corpectomy implant of claim 17, wherein said second endplate is fixedly attached to said second end of said second cage.

19. The bi-directional adjustable corpectomy implant of claim 17, wherein said second endplate is articulatably attached to said second end of said second cage.

20. The bi-directional adjustable corpectomy implant of claim 11, wherein said bias member is a spring.

* * * * *